(12) United States Patent
Olsen et al.

(10) Patent No.: US 6,632,920 B1
(45) Date of Patent: Oct. 14, 2003

(54) 36 HUMAN SECRETED PROTEINS

(75) Inventors: Henrik S. Olsen, Gaithersburg, MD (US); Steven M. Ruben, Olney, MD (US); Craig A. Rosen, Laytonsville, MD (US); Laurie A. Brewer, St. Paul, MN (US); Reinhard Ebner, Gaithersburg, MD (US); Roxanne Duan, Bethesda, MD (US); Kimberly Florence, Rockville, MD (US)

(73) Assignee: Human Genome Sciences, Inc., Rockville, MD (US)

(*) Notice: Subject to any disclaimer, the term of this patent is extended or adjusted under 35 U.S.C. 154(b) by 102 days.

(21) Appl. No.: 09/716,129

(22) Filed: Nov. 17, 2000

Related U.S. Application Data

(63) Continuation of application No. 09/382,572, filed on Aug. 25, 1999, now abandoned, which is a continuation-in-part of application No. PCT/US99/03939, filed on Feb. 24, 1999.
(60) Provisional application No. 60/076,053, filed on Feb. 26, 1998, provisional application No. 60/076,051, filed on Feb. 26, 1998, provisional application No. 60/076,054, filed on Feb. 26, 1998, provisional application No. 60/076,052, filed on Feb. 26, 1998, and provisional application No. 60/076,057, filed on Feb. 26, 1998.

(51) Int. Cl.$^7$ .......................... A61K 38/00; C12P 21/06
(52) U.S. Cl. ....................... 530/300; 530/324; 435/69.1
(58) Field of Search ................................. 530/300, 324; 435/69.1

(56) References Cited

FOREIGN PATENT DOCUMENTS

| EP | 0 599 077 A2 | 6/1994 |
|---|---|---|
| WO | WO96/17925 A1 | 6/1996 |
| WO | WO97/04097 A2 | 2/1997 |
| WO | WO98/54963 A2 | 12/1998 |
| WO | WO99/43693 A1 | 9/1999 |

OTHER PUBLICATIONS

Attwood (Science, 290:471–473, 2000).*
Gerhold et al. (BioEssays, 18(12):973–981, 1996).*
Wells et al. (Journal of Leukocyte Biology, 61(5):545–550, 1997).*
Russell et al. (Journal of Molecular Biology, 244:332–350, 1994).*
Bioconjugate Chemistry (1994) vol.5:333–338.*
GenBank Accession No. W32308, Hillier et al., The WashU–Merck EST Project (Oct.–11–1996).
GenBank Accession No. AA774284, Hillier et al., WashU–NCI Human EST Project (Jan.–29–1998).
GenBank Accession No. AA613279, NCI–CGAP, Tumor Gene Index (Oct.–16–1997).
GenBank Accession No. AA643974, NCI–CGAP, Tumor Gene Index (Oct.–27–1997).
GenBank Accession No. T85021, Hillier et al., WashU–Merck EST Project, (Mar.–17–1995).
GenBank Accession No. AA427866, Hillier et al., WashU–Merck EST Project, (Oct.–16–1997).
GenBank Accession No. AA446322, Hillier et al, WashU–Merck EST Project, (Jun.–3–1997).
GenBank Accession No. A001029, Hillier et al, WashU–Merck EST Nov.–29–1996.
GenBank Accession No. T70779, Hillier et al, WashU–Merck EST (Mar.–15–1995).
GenBank Accession No. AA496985, Hillier et al, WashU–Merck EST Aug.–12–1997.
Jacobs et al., "A Novel Method for Isolating Eukaryotic cDNA Clones Encoding Secreted Proteins," J. Cell. Biochem.–Suppl. 21A:19.
EMBL Accession No. AL008725, Clark, G., "Human DNA sequence from clone RP1–148E22 on chromosome 20q12–13.12 Contains the YWHAB gene encoding tyrosine 3–monooxygenase/ntryptophan 5–monooxygenase activation protein, beta polypeptide, a novel gene similar to PABPC1 (poly (A)–binding protein, cytoplasmic 1), 2 CpG islands, ESTs, STSs and GSSs," (Nov.–7–1997).
EMBL Accession No. AC002310, Loftus et al., "Human Chromosome 16 BAC clone CIT987SK–A–635H12, complete sequence," (Jul.–19–1997).
EMBL Accession No. W27084, Macke et al., "20a9 Human retina cDNA randomly primed sublibrary Homo sapiens cDNA, mRNA sequence," (May–14–1996).

\* cited by examiner

*Primary Examiner*—Marianne P. Allen
*Assistant Examiner*—Lori A. Clow
(74) *Attorney, Agent, or Firm*—Human Genome Sciences, Inc.

(57) ABSTRACT

The present invention relates to 36 novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

42 Claims, No Drawings

SEQUENCE LISTING

<160> NUMBER OF SEQ ID NOS: 186

<210> SEQ ID NO 1
<211> LENGTH: 733
<212> TYPE: DNA
<213> ORGANISM: Homo sapiens

<400> SEQUENCE: 1

| | | |
|---|---|---|
| gggatccgga gcccaaatct tctgacaaaa ctcacacatg cccaccgtgc ccagcacctg | 60 |
| aattcgaggg tgcaccgtca gtcttcctct tcccccaaa acccaaggac accctcatga | 120 |
| tctcccggac tcctgaggtc acatgcgtgg tggtggacgt aagccacgaa gaccctgagg | 180 |
| tcaagttcaa ctggtacgtg gacggcgtgg aggtgcataa tgccaagaca aagccgcggg | 240 |
| aggagcagta caacagcacg taccgtgtgg tcagcgtcct caccgtcctg caccaggact | 300 |
| ggctgaatgg caaggagtac aagtgcaagg tctccaacaa agccctccca accccatcg | 360 |
| agaaaaccat ctccaaagcc aaagggcagc ccgagaacc acaggtgtac accctgcccc | 420 |
| catcccggga tgagctgacc aagaaccagg tcagcctgac ctgcctggtc aaaggcttct | 480 |
| atccaagcga catcgccgtg gagtgggaga gcaatgggca gccggagaac aactacaaga | 540 |
| ccacgcctcc cgtgctggac tccgacggct ccttcttcct ctacagcaag ctcaccgtgg | 600 |
| acaagagcag gtggcagcag gggaacgtct tctcatgctc cgtgatgcat gaggctctgc | 660 |
| acaaccacta cacgcagaag agcctctccc tgtctccggg taaatgagtg cgacggccgc | 720 |
| gactctagag gat | 733 |

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
      L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

| | | |
|---|---|---|
| gcgcctcgag atttccccga aatctagatt tccccgaaat gatttccccg aaatgatttc | 60 |
| cccgaaatat ctgccatctc aattag | 86 |

<210> SEQ ID NO 4
<211> LENGTH: 27
<212> TYPE: DNA
<213> ORGANISM: Homo sapiens

<400> SEQUENCE: 4

| | |
|---|---|
| gcggcaagct ttttgcaaag cctaggc | 27 |

<210> SEQ ID NO 5
<211> LENGTH: 271

```
<212> TYPE: DNA
<213> ORGANISM: Homo sapiens

<400> SEQUENCE: 5
ctcgagattt ccccgaaatc tagatttccc cgaaatgatt tccccgaaat gatttccccg        60
aaatatctgc catctcaatt agtcagcaac catagtcccg cccctaactc cgcccatccc       120
gcccctaact ccgcccagtt ccgcccattc tccgccccat ggctgactaa ttttttttat       180
ttatgcagag gccgaggccg cctcggcctc tgagctattc cagaagtagt gaggaggctt       240
ttttggaggc ctaggctttt gcaaaaagct t                                      271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaaccccc gg                                    32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                      31

<210> SEQ ID NO 8
<211> LENGTH: 12
<212> TYPE: DNA
<213> ORGANISM: Homo sapiens

<400> SEQUENCE: 8
ggggactttc cc                                                           12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccggggact ttccgggact ttccatcctg        60
ccatctcaat tag                                                          73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct        60
caattagtca gcaaccatag tcccgcccct aactccgccc atcccgcccc taactccgcc       120
cagttccgcc cattctccgc cccatggctg actaatttt tttatttatg cagaggccga       180
ggccgcctcg gcctctgagc tattccagaa gtagtgagga gctttttttg gaggcctagg       240
cttttgcaaa aagctt                                                      256

<210> SEQ ID NO 11
<211> LENGTH: 1441
<212> TYPE: DNA
```

<210> ORGANISM: Homo sapiens

<400> SEQUENCE: 11

```
ggcacgagtt ttatttatct tgcctagggt gtgttgggct tcataaatct gtggattggt      60
atctttcgtc agttctgtaa aagtctcagg tactctttgt taacattcgt ctctgcccca     120
tttttcttct agaattatga tcaaacatgc actaattaga cctttattg tattctcttt     180
gcttcttagg ctatgctctg aaaatttatt ttgtcctaat actcagttta tagttctgtc     240
ttgtttccaa tctgttgtta aatccctcct ttcaatttta aatctcagtt actgtatttt     300
ttaattctag aaggtcgttt ggttctttca aatccactag atcaagtcac tctctgtgac     360
ttcctacgac ctatattcta gcctttgcct tttattattt tttaacattg taagcaaagt     420
tgttttatag ttgataattc ttgtatctgt ggtctttgtc tcttcatact agctgttatt     480
tcttaacagt tttccctgat cccaccttac ttcctcatag atttgattat ctttgattat     540
gtgctgctta ttttttttaa agataattat ctgtattaat atgagaccta gattttaaga     600
tacttcccct caggattgtg ctgtgtgcct gggcacattg caagtccaaa ttactttaaa     660
gtatcctaga acaccagagg tgaaaattca tgccattctc gtgcatcttt accttatggg     720
tatagcccat tgggaatcct tagtgtcggg agggagttct attacacctt ccacttcggg     780
cagatcctgg gctttgacat tcgtcctctt catcataacc aaatatcaga cttgcctaat     840
gcgtaaatgc ccttggggta aagcatctgt gttctgctta cctctcaggg ttcctgcttt     900
tccctttagc tttggttcca tcacttgtgt gttcaaccag tatgggaaac tgcctctaga     960
agcagtgttt taaaatttta gtctaaccat aaaaatagag aatgcttacc ctctggatat    1020
aaatgccata gcgataactt tgaactccta cattacatgc cttttatgta aggcaaacct    1080
cagtacacat tgagagacag tgtcatatac ttattaagat cacaggctct aaaatcagac    1140
tgccttgttt aaatcctggc cctgccatgt agtagtaacc tgtgttaatt tatgcaagat    1200
acgtaatctc tctgtgcctt ggtttcttcg tttaaaaagc agaataatag cttgcctcat    1260
gtggtcatta tgaaaaacaa acaaggccgg gcaccgtggc ttacgcctgt agtctcagca    1320
ctttgggagg ctgaggtggg cagatgacct gaggtcggga gtttgagacc agcctgccca    1380
acatggagga accccgtctc tactgaaaaa aaaaaaagag agagagagag agagaactag    1440
t                                                                   1441
```

<210> SEQ ID NO 12
<211> LENGTH: 2160
<212> TYPE: DNA
<213> ORGANISM: Homo sapiens

<400> SEQUENCE: 12

```
ttttgaattc tatagattgt cttggaagga tactgtgtga tgggtcaggc acacagtaat      60
tggagacttt taatgtatgt aatatttcat agattgcatg ctattaatca tctgtgaggg     120
tagtatttt tgttttattg taagtttccc tctttttta taaattaaaa gatggttggt     180
attaggaatt tcaaatgaat gcagaaaatc ttacatgctg tgtactatta atattataac     240
agacgatcca agtccaaaat ctgaccaata aagcaaccat tttatcaaga tagagggatt     300
ctaatgggag agggattct tccctcctga gtttgtgtg tccagtcccc ttaaaaaaaa     360
tgaatagttg tcttttcttg tgcatattaa tactcgaaag tgccatggtg gtattaatga     420
aagtacactt tattgttgcc tttgaactta cggccaaggc aataaatcag aaacaaaat     480
agtgccaatg tgtcaaaatc gacatctgag agattcagcc tcccatttgg aataaatatg     540
```

```
aatcttctaa gctatcttgt ttaatatttt ccatcattta gctacttcct atctccctca      600
gaggcgcctg ctgttcccat tttagagttg acagtggcct gctaattttg ctatgttcct      660
aaaagttact gggtgtgaga cattttcatc ccctcctttt tcctactgct ggtgtttatt      720
atccagctag acaatatttt atgcatattt accgtgatgt ctggaccgta cctgtgctcc      780
ttggcagttt atgttgaaga taactaaaga ttttctctt tgggaggcat caaaatgatg       840
gtagtttgct tttatctttt tatgttcatt ttcttttagt aggtgacctt tctgcattaa      900
gaactgtttt tatcttttac tacctttct tttctccttt gtggagacag catgacatgt       960
cctgaaggtc acctttgcct ttgaaaaagg tttgatggag gaattcacag gtgactgaca     1020
agtctttgaa aagaatggga tctgctcact tctggtctt ttggccggga actcctgatt     1080
ggtgttaagg tggtaatttc ccccatataa gatttagaat cactgagttt gagctagatg    1140
aaatttttaa aatttctggt tgtctcatta gactgatgag gtgagttttc ttcttcatat    1200
gaacagctag ttaataacag cagagttctc actcagtgct cagtacttaa ttttccactg    1260
caccacaact gtcttaacta aatgtgctgt atttttctt aaaagttaag agttctattt     1320
ggtgttttca ggaatatacg tgaaaagaca tgccatgttt tggtaaatac catcagagtt    1380
gtgtaaaggc gtgtactaag tgcaatctta atttgtggaa ataatcttca tttacccctc    1440
ctaaaactac actcagtata aacactttcc cataaggtgt gtgcagtaaa aatgttatat    1500
tactccaaca ctggcaggag cacagcacag cagccttatt ggagagagcc ttataaaagt    1560
gattaaatgg aggcattgag ctcattacct ttaagtttac tttgtgctga cctttgttcc    1620
tgttttgaga atctcatata attattaaaa aaaaaaaca attaaaacga aacggcgggg     1680
cctagctgtg tataaatgat ccttgctgaa tatcttaagg ttttttgtaa gaaaaaagaa    1740
aaaccaacaa aaaaagctta ttttcacatt aaaatgaaac ctcttttgca acttaagaat    1800
tctatggaaa agcagttttt atcatatttt gtgtccatgc accattttc ttaaaatggc     1860 ttacaaaaaa gaatgtaaac aatttgtgat ctggccagtt gtacttttag ctcccagagg    1920
gagagttggt ggtattatga gttgagtaaa aaccatccag gggaacttga gggagcagtc    1980
tgttgccagt aatgttcctt gtgtgccatt aaaccacctc cagatgagtg gaggaacatc    2040 acttttttaat ttttaattg tatttggaat tgttgccgtg tactaagaac ttgacctaaa    2100
taaaatccca caaagtataa aaaaaaaaa aaaaaaaaa aagggcggcc gctcgcgatc      2160
```

<210> SEQ ID NO 13
<211> LENGTH: 1202
<212> TYPE: DNA
<213> ORGANISM: Homo sapiens

<400> SEQUENCE: 13

```
gggtcgaccc acgcgtccgg ttttttaga aatagaagtg cttacagatt tgtttgagca       60
gaatagatac ccatgttcag agagagagag agagagccat tgagaggcas agagtgccga     120
atgtgaattc tgtgtaaatt gaaaagttac ggtccccgtc cataaggaga tggctctggt     180
tgtcttgaat ttagacagct ttccagagga ggaggttctc tcctgcagca gtgtgggaaa     240
aaaatctacc agatttggac cagaatgact gcaatttagg tcagaacatg atacttagag     300 ggaaaaagt aatcatggct tgaatagctg ccctaaggcc agctacaggg ctgcagggtc      360
tgtggacctt tcttgtcaga actcaggatc cttaggagtc cccacaaggg catggaggct    420
gtggccatca tgagtggaag aaccagcttc caaaggaacc taggattgtt ctggccctgg    480
```

-continued

```
ctccaggtgc atatctctgc tttccgtgag cattgaatgg gaaatcacgt gttagcagaa    540
taaatcccag aatacacatt caggaggaga tggttccaca tggcacgtaa gtcctttgcc    600
ttattgatgt ttgtctggca gatgtcctta agccttccca tcaagggctt tattctaagg    660
gtggctaact ggctatttaa acctcatctc aatagtgtct gtctaggatg caaaatcac     720 accaggttct gctgggcaaa tctcccaggt ggcgtattgc tagaggagag cgccactgca    780
gaggacacac tgtcttggcc actggctttg caaaccatag tggaggaggg agtctggggt    840
caccaaccac ttcctggctg actgcctgag ccacattata caagactgtt tgttgactta    900
gtaatactga agccagagct caccaagatt ctgacatcaa gcatgaaagt gactaattct    960
ttcawttccc agcactttga caaggggac tctcttaaaa ctcctcatcg dacgttagtg    1020
gaagtcgact catgtatcta aacatgtagc cagcgtaagt tcttggtcag attgatctaa   1080
tgactttttt agcgtgtgtg tgtgtgtgtg tgtgtgtgtt taatctttt aagtttgggt    1140 gaagtttgac cttctagaat cctgtttat tcctgagcaa aaaaaaaaaa aaaaactcg     1200 ag                                                                  1202
```

<210> SEQ ID NO 14
<211> LENGTH: 1554
<212> TYPE: DNA
<213> ORGANISM: Homo sapiens
<220> FEATURE:
<221> NAME/KEY: SITE
<222> LOCATION: (695)
<223> OTHER INFORMATION: n equals a,t,g, or c
<221> NAME/KEY: SITE
<222> LOCATION: (874)
<223> OTHER INFORMATION: n equals a,t,g, or c
<221> NAME/KEY: SITE
<222> LOCATION: (1190)
<223> OTHER INFORMATION: n equals a,t,g, or c

<400> SEQUENCE: 14

```
gctttaatag tgtacactta cacatctgga aggaagagag ttccatatgg cagggatgat     60
tgggacagga gggatctttt gataactttg tgtgagcatg aaaatcgaat ggggaaggga    120
gagctgtgaa aaaaaaatgt tatctctttt tttttgcttc tggaaaccca gcttttttggt   180 cagccgtctt gtgatttggc tgggcctggt ttgtgggggt cgctctctga gttgggtagc    240
tcttggagaa gattatctgg gaactcccat ccttatccca aacatacacc aaacctgccc    300
ccatccacca ttatgggaat tagtaccaga gcatccttgc agattagttc tcattttctc    360
tctttgtgag cacacacaca tcaggtagag ttccagaaac ccagctttag gacactgttc    420
acatatcaca ggaggagcaa ggacatgaat acaagagagc tctttcctga ccagcagtgg    480
gargtggttg tactatctat ttawttgttt attwatttat ttatttttg agatggartc     540 tccttctgtc acccaggctg gagtgcagtg gcatgatctc ggctcactgc aatctctgcc    600
tcctgggttc aagcagtcct cctgcctcag cccccaagt agctgsgatt acaggctgca     660
ccaccatgcc ccgctaattt ttgtattttt agtanagatg gggtttcacc atgttggcca    720
ggctggtctg taactcctga mctcaggtga tccacctgcc ttagcctccc aaggtgctgg    780
gattacaggt gtgagccacc gtgcccggsc tggttccact atttattaaa atgtatatat    840
gtgttttyca cttttttggt aggcatttta ttgntaataa tttggaaatt aaaaaaattt    900
ctccacaagc ttatttttg tggagacaag gtctccctgt gttgcctagg ctggtcttga    960
attcctgggc taagtgattg gtctgccttg gcctctcaaa gtgctgggga ttacaggcat   1020
aagtcaccat gccctgtttg scagcaagkt ttawackgct cttttttggta gggawwtkct   1080
```
maggtwcagt gatagagaac atgkagttgt ggtgggawac agtggctyat gactgtatcc    1140
gcactttggg aggctgaggc aggaggattg cttgaggctg agagttgagn acaggcctgg    1200
gcaacatagc aagacacctt ctctaaaatg aaaaaaatta gctggatgtg gtgtcatgta    1260
cctgtagtcc cagttgcttg ggaggctgag gcaggaggat cacttgagcc tgggtgttca    1320
agataggcct ggtcaacaca gcaagacccc ttctctaaaa atgaaaataa aaaaattagc    1380
tggttgtggt ggcatgtacc tgtagtccca gttacttggg aggctgagac aggaggattg    1440
cttgagccag gggtttgagg ctgcagtgag ctatgactgc tcccctgcac cccaggctgg    1500
gtgacagagt gagacccagt ctctaaaata aaaaaaaaa aaaaaaact cgta    1554

<210> SEQ ID NO 15
<211> LENGTH: 1540
<212> TYPE: DNA
<213> ORGANISM: Homo sapiens
<220> FEATURE:
<221> NAME/KEY: SITE
<222> LOCATION: (651)
<223> OTHER INFORMATION: n equals a,t,g, or c
<221> NAME/KEY: SITE
<222> LOCATION: (1124)
<223> OTHER INFORMATION: n equals a,t,g, or c

<400> SEQUENCE: 15
agaattcggc acgagggcat attactttcc taggactgcc acaacaaact attaccaact     60
agcggcttaa acaacaaga gcttattcct cacagttctg gaggcagaa gtccaaaacc      120 aaggtgtcag gaaggtcatg ctctctccaa agtctccaag gatgctcctt ccttgcctcc    180
tccagcctct ggtcgtggcc aacatcccga gggttccttg gcttgcagat gaatcactta    240
atcccacccc catcatcaca tggcagtccc cctgtgtagc tcagctctgt ccaaatttcc    300
cctttcctac aaggacatta gtcactggat tatgacacag ctcatcttaa ctggattata    360
tctgcaaaga ccctgttata tctgcaaaga cgagttaaca ttcacatgtt ccaggggaga    420
tatgaatttt aagggacag tattggaccc agtataggag ggcaggcagc agcgagggag    480
ccagggaggg ctggcctgac ttgagcctgt ttgaaaagca tcatcctcct accaagactg    540
ggggctgctg gttctgacaa ggtttgcagg atcagctggg atgatgggtt scamccaytc    600
cttcgagyta cgttggaccc ctgggcccac ttacagcaag gagcttgccc ntycgtgtag    660
ctctycgtca gtgtgggaaa atctgartga gccagagaag ggtgagattc cccctgcaga    720
gcaggcagta ctgagcaaat ccaggatcca gaactccagt tctaatcctg gctcttgcct    780
gctttcctgt gtgaccctgg ggaagtggtt ttccctctct gagactctcc ttccccatgt    840
gagtcacaag ggctgggcct agctgacccc caaggccctt acatgagtgg atagttgcat    900
tttaaacctg gtgctcccca ggataaggga gtcaacccca aggagactgg ggtttctcct    960
gagcctggcc cctggggatg agcactcact gtggaaaaag ctggccactt cttagccctt    1020
gtcatgggca gaaacatgc ccctccagcc ccaccagcac caacacacag ccaagctcac    1080
tgtttcattt ttagagagaa atcagggctt tcggtgcagc tgantgacac agacaagggg    1140 cgggggggaca tgaaagggag cgggcaagga cggaaattac acttctccta gcaacctggt    1200
tctgcagctc ctaggcctgg ggccgcgtga tacatgccat tcccaattaa cgggatgtta    1260 aatataccccc ggctcagcct gccccatgct gagccccgcc tggggcagtg cagggagcca    1320
tgtgatggtg tagagcactc tgcaacaccc catattcatg ttcccactcc tagggccccg    1380
ctcggtcccc aggaggccag agcggtcctg ccctctgcct gagcatggct cagctccagc    1440

```
ctccacttgc cctcccctat gctggccagc tcggggggtct gcaggcagcc tgtggggcag     1500
ggccagttgg ccaaactctc caagccagaa gcccctcgag                             1540
```

<210> SEQ ID NO 16
<211> LENGTH: 1057
<212> TYPE: DNA
<213> ORGANISM: Homo sapiens

<400> SEQUENCE: 16

```
tcgacccacg cgtccgctga gattacaggt gtgagccacc aggctcagcc ccctaagatt      60
tgaaacactt taaatggccc atggtagggt tcctgctagg ataaaacatt aagcggctgt     120
taaaagaaat aaaaggagga cacgtctctg tgcactggtg tggacaaatc tccaagtcac     180
tgcaaaatgg aaaagtata agatgctctt tccctgaacc tcaagggtcc cgcccctctc     240
actttcaggt ctctggacct ctgactgaca ctgtgcctgc ccaggtccct gtatgcactg     300
ccacagtgcc ctgggcccca tgtccacccc tgtcctgccc ttctctggga tagggctggc     360
cttcctctgc ctctgcctgg ctgcatccat ggtcgatctc aagtgccttg gcatgaactc     420
cactctcctg cagccttcaa tcaaggaatg atggggatgt gtacataccc caccccaccc     480
cttggcaggg tgatgctgag gtgtggattt ttaacagttc ccagactttc ccaggaggct     540
tgggtttggg tgcccacagt gggagctggt gtgatatcat accttcgccg ccgccttttc     600
cttcctgttc tctgtgcccc tactcccact ctagagctgc cccgtttctc tgttttcgtg     660
aaagagctga ccctgtgctg cctcccactc tcccaatgcc cctgccactc ctgtgagcct     720
gctgctggtg aggtcggtgc tgacctctgt gttgctggat aatgagtcat ctatctctgg     780
aggagaagaa aggcaggtcc tccacagccc tgataaaatc tccaagtctc ccagtttcgg     840
gtccctctcc tgggatgcag acccactgcc tgcccagctg gtacgatcca catgccctct     900
tcttgggaat aggggcatgg gaaagtgact aaagatactg ttctggctgc tgtgttcact     960
gtgagtaata aactgtccat ttctccgaaa aaaaaaaaaa aaaaaaaaaa aaaaaaaaa      1020
aaaaaaaaaa aaaaaaaaaa aaaaaaggg cggccgc                               1057
```

<210> SEQ ID NO 17
<211> LENGTH: 2080
<212> TYPE: DNA
<213> ORGANISM: Homo sapiens
<220> FEATURE:
<221> NAME/KEY: SITE
<222> LOCATION: (145)
<223> OTHER INFORMATION: n equals a,t,g, or c

<400> SEQUENCE: 17

```
aattcggcac gagacctta gggtgcgcgg gtgcagtata tctcgcgctc tctcccttt        60
ccccctcccc tttccccacc ccgggcgctc aggttggtct ggaccggaag cgaagatggc     120
gacttctggc gcggcctcgg cgganctggt gatcggctgg tgcatattcg gcctcttact     180
actggctatt ttggcattct gctggatata tgttcgtaaa taccaaagtc ggcgggaaag     240
tgaagttgtc tccaccataa cagcaatttt ttctctagca attgcactta tcacatcagc     300
acttctacca gtggatatat ttttggtttc ttacatgaaa aatcaaaatg gtacatttaa     360
ggactgggct aatgctaatg tcagcagaca gattgaggac actgtattat acggttacta     420
tactttatat tctgttatat tgttctgtgt gttcttctgg atcccttttg tctacttcta     480
ttatgaagaa aaggatgatg atgatactag taaatgtact caaattaaaa cggcactcaa     540
```

```
gtatactttg ggatttgttg tgatttgtgc actgcttctt ttagttggtg cctttgttcc    600
attgaatgtt cccaataaca aaattctac agagtgggaa aaagtgaagt ccctatttga     660
agaacttgga agtagtcatg gtttagctgc attgtcattt tctatcagtt ctctgacctt    720
gattggaatg ttggcagcta taacttacac agcctatggc atgtctgcgt tacctttaaa    780
tctgataaaa ggcactagaa gcgctgctta tgaacgtttg gaaaacactg aagacattga    840
agaagtagaa caacacattc aaacgattaa atcaaaaagc aaagatggtc gacctttgcc    900
agcaagggat aaacgcgcct taaacaatt tgaagaaagg ttacgaacac ttaagaagag     960
agagaggcat ttagaattca ttgaaaacag ctggtggaca aaattttgtg gcgctctgcg   1020
tccctgaag atcgtctggg gaatattttt catcttagtt gcattgctgt ttgtaatttc    1080
tctcttcttg tcaaatttag ataaagctct tcattcagct ggaatagatt ctggtttcat   1140
aattttggga gctaacctga gtaatccact gaatatgctt tgcctttac tacaaacagt    1200
tttccctctt gattatattc ttataacaat tattattatg tactttattt ttacttcaat   1260
ggcaggaatt cgaaatattg gcatatggtt cttttggatt agattatata aaatcagaag   1320
aggtagaacc aggccccaag cactccttt tctctgcatg atacttctgc ttattgtcct    1380
tcacactagc tacatgattt atagtcttgc tccccaatat gttatgtatg aagccaaaa    1440
ttacttaata gagactaata taacttctga taatcataaa ggcaattcaa ccctttctgt   1500
gccaaagaga tgtgatgcag awgctcctga agatcagtgt actgttaccc ggacatacct   1560
attccttcac aagttctggt tcttcagtgc tgcttactat tttggtaact gggccttct    1620
tggggtattt ttgattggat taattgtatc ctgttgtaaa gggaagaaat cggttattga   1680
aggagtagat gaagattcag acataagtga tgatgagccc tctgtctatt ctgcttgaca   1740
gccttctgtc ttaaaggttt tataatgctg actgaatatc tgttatgcat ttttaaagta   1800
ttaaactaac attaggattt gctaactagc tttcatcaaa aatgggagca tggctataag   1860
acaactatat tttattatat gttttctgaa gtaacattgt atcatagatt aacattttaa   1920
attaccataa tcatgctatg taaatataag actactggct ttgtgaggga atgtttgtgc   1980
aaaatttttt cctctaatgt ataatagtgt taaattgatt aaaaatcttc cagaattaaa   2040
aaaaaaaaaa aaaaaaaaaa aaaaaaaaaa gggcggccgc                         2080
```

```
<210> SEQ ID NO 18
<211> LENGTH: 602
<212> TYPE: DNA
<213> ORGANISM: Homo sapiens
<400> SEQUENCE: 18
aattcggcac agkttgtgtt tctmatgttc caggtccggc caggctggca gctcctgctg     60
gtcatgttt cctcatgtgc tgtttccaac cagctcttgg tctggtaccc agcaactgcc    120
ttagcagaca acaaacctgt agcacctgac cgacgaatca gtgggcatgt gggcatcatc    180
ttcagcatgt catacctgga aagcaaggga ttgctggcta cagyttcaga agaccgaagc    240
gttcgtatct ggaaggtggg cgacctgcga gtgcctgggg gtcgggtgca gaatattggg    300
cactgctttg ggcacagcgc ccgtgtgtgg caggtcaagc ttctagagaa ttaccttatc    360
agtgcaggag aggattgtgt ctgcttggtg tggagccatg aaggtgagat cctccaggcc    420
tttcggggac accaggatgt gtaccccggtt gtagtaggag ctgaaatcca tgctgagctg    480
taccaggaac ttgcatatct agagacagag actgagtcac tggcccatct cttgctctct    540
gtccccaggc cagaataaag aatagagtgt aaaaaaaaaa aaaaaaaaa aaaaactcg     600
``` ag    602

<210> SEQ ID NO 19
<211> LENGTH: 629
<212> TYPE: DNA
<213> ORGANISM: Homo sapiens
<220> FEATURE:
<221> NAME/KEY: SITE
<222> LOCATION: (533)
<223> OTHER INFORMATION: n equals a,t,g, or c

<400> SEQUENCE: 19

| | | | | | |
|---|---|---|---|---|---|
| gcacactttg | accacttgtg | atgagcctta | tttgggagca | aggtcttcaa | ctttgtggtt | 60 |
| tttgtttgtt | ttatttggtt | ttctgcttct | gcattagttc | acttagggtg | atggctttca | 120 |
| gctgctycca | tgttgcttgc | tgcaaaggat | atgattttgt | ycttttttat | ggctgtgtag | 180 |
| tattccatgg | tgtatatgga | ccacattttc | tttatccaat | ccaccatata | tgggcaccta | 240 |
| ggttgattcc | atgtctttgc | tattgtgaat | agcactgtga | tgaacataga | agtggattaa | 300 |
| atttctttt | cttgacagtc | tcctaattta | tgcttgtaca | tatattttc | tctcatgcct | 360 |
| tgaggttttt | aaaagtcctc | tcctctttct | catggcaata | cttttactaa | agtacatttc | 420 |
| ctgggaatcc | ttagggttcc | ccttattttg | aataggctga | atattttcat | atgtttggtg | 480 |
| attttatct | tttaatcctt | taataggttt | gaaagtctct | cttgatatgg | gtngctcaga | 540 |
| taggctccat | cgtagagtct | agaaatcatc | ctatgatttt | tttttgccca | ttcctaggtt | 600 |
| aaaaaaaaaa | aaaaaaaaa | aaactcgag | | | | 629 |

<210> SEQ ID NO 20
<211> LENGTH: 2067
<212> TYPE: DNA
<213> ORGANISM: Homo sapiens

<400> SEQUENCE: 20

| | | | | | |
|---|---|---|---|---|---|
| aattcggcac | gaggaaaaac | aaaagttttt | taaaacaata | aaagttaaca | gtcaataatg | 60 |
| tgtttgtcgg | caagaagccc | tctgttaata | atggtctaaa | caaataagac | attgttttc | 120 |
| tccaataaag | aaatccagag | gcaggcagta | gctggctttg | attcagcctc | tgactgtcac | 180 |
| tgtcagggcc | ccaggcccca | tgagcctttc | gtctttcctg | catgttggct | tatcttctca | 240 |
| tgcttgtgac | ttcctggttg | caacacggct | gctgcaacac | cagacatctt | gcctgtcttc | 300 |
| aaggcaggaa | ggaggggggaa | actatcgcct | accagctatt | tttcttacct | tagctcctcc | 360 |
| atgtcttgga | tcaaaagcat | ctctttgaac | ctctccctca | ggcatacccct | gaaatgctgt | 420 |
| ggactttaac | cttttttctg | ttgcaaaggt | cgctcacatc | tccctggttg | tttggtcttc | 480 |
| tcttccttgg | ctctagtaac | acagcagtct | gttgcttcct | aggacaactt | ataatgggac | 540 |
| ccaaaggggaa | aagaggattt | cccgggcctc | caggaagatg | tctttgtgga | cccactatga | 600 |
| atgtgaataa | cccttcctac | ggggaatctg | tgtatgggcc | cagttccccg | cgagttcctg | 660 |
| tggtaaggct | ttctgggaga | agtctggggt | ggttatccgt | gaggacctct | cacctgatcc | 720 |
| ttatggggct | ttgtaaaatc | ctttcagtaa | aactaacttt | ttttcacgac | tctgagtaca | 780 |
| ccctcattat | aggaaattgg | aaaatatgag | aaaatcaaga | ggaaaaccaa | attgtccatt | 840 |
| tgattgtgag | tccattttgg | ggtattttct | ttgtcttatt | aaaatctaac | tttatatgg | 900 |
| ttgagattat | attgtataaa | aatgtacttt | tggccgggca | tggtggctta | tgcctgtaat | 960 |
| cccagcactt | tgggaggcca | aggtgggtgg | attataaggt | caggagttcg | agatcagcct | 1020 |

```
ggccgataca gtgaaacccc atctctacta aaaatatat ttaaaaaatt agccgggcgc    1080
ggtggtgcac gcctgttgtc tcagctactt gggaggctga ggtgggagaa tcgcttgaac   1140
ccaggaggcg gagattgcag tgagctgaga tagcaccact gcactccagc ctgggcaaca   1200
gagcgagact ccgtctcaaa aaagttata ctttgktatc ttagttgaaa tcctgccatg    1260
tttccacact ctataaataa catttttaaac ttttttattag ggaaaatttc aaatacatat  1320
aaaagcagaa caaatagtgt aatgaacccc tgtgtaccct tcacccaact ttaataatga   1380
tcaactcatg gcgagcctgt gtccttgttt tctctttatg cctactcact cctgcccatt   1440
ctctgttgta ttattttgaa gtaaaccttg acatctgtt catcataatc atccatctag    1500
tgtggctgtg ctacaattta cttaaccagt gttggtgttt aaccaaccta ttgcttattg   1560 gccacccca agcttttttac taatgtaaat aatgctgtaa agaatatctt tgagtaggat   1620
aattttaaga atcacttcca gatgtcaaat tacttgacta tatgacattg cctttttaact  1680 taagtcttgg gaacgtttta aatatttaaa aatgttaaat ccgaggccgg gcgcggtggc   1740
tcatgcctgt aatcccagaa ctttgggagg ccgaggtggg tggatcacct tgaggtcagg   1800
agctcgcaac cagcctggcc aacatggcga acccatatct ctactaaaaaa tacaaaagtt  1860 agccaggcat tgtggtgcac acctgtaatc ccacctactc gagaggctga ggcaggagaa   1920
ttgcttgaac ccgggaggca gaggttgcaa tgagccgaga tcacgctact tcactccagc   1980
ctgggcaacc gcgtgagact ccatctcaaa aacaaaagaa aaaaaaaaw aaaaaaaccg    2040 gcacgagggg gggcccgtac ccaatcg                                       2067

<210> SEQ ID NO 21
<211> LENGTH: 997
<212> TYPE: DNA
<213> ORGANISM: Homo sapiens
<220> FEATURE:
<221> NAME/KEY: SITE
<222> LOCATION: (963)
<223> OTHER INFORMATION: n equals a,t,g, or c

<400> SEQUENCE: 21
cccgactcta ggccggaagc gcgcggagac catgtagtga gaccctcgcg aggtctgaga     60
gtcactggag ctaccagaag catcatgggg ccctggggag agccagagct cctggtgtgg    120
cgccccgagg cggtagcttc agagcctcca gtgcctgtgg ggctggaggt gaagttgggg    180
gccctggtgc tgctgctggt gctcaccctc tctgcagcc tggtgcccat ctgtgtgctg    240
cgccggccag gagctaacca tgaaggctca gcttcccgcc agaaagccct gagcctagta    300
agctgtttcg cgggggggcgt cttttttggcc acttgtctcc tggacctgct gcctgactac   360
ctggctgcca tagatgaggc cctggcagcc ttgcacgtga cgctccagtt cccactgcaa    420
gagttcatcc tggccatggg cttcttcctg gtcctggtga tggagcagat cacactggct   480
tacaaggagc agtcagggcc gtcacctctg gaggaaacaa gggctctgct gggaacagtg   540
aatggtgggc cgcagcattg gcatgatggg ccagggtcc cacaggcgag tggagccca   600 gcaacccct cagccttgcg tgcctgtgta ctggtgttct ccctggccct ccactccgtg    660
ttcgaggggc tggcggtagg gctgcagcga gaccgggctc gggccatgga gctgtgcctg   720
gctttgctgc tccacaaggg catcctggct gtcagcctgt ccctgcggct gttgcagagc   780 cacccttaggg cacaggtggt ggctggctgt gggatcctct tctcatgcat gacacctcta    840
ggcatcgggc tgggtgcagc tctggcagag tcggcaggac ctctgcacca gctggcccag   900
tctgtgctag agggcatggc agctggcacc ttttytytata tcacctttyt ggaaatcctg   960
```

```
ctntttcatc ccaaatttaa gggggtttca agaagaa                                  997
```

<210> SEQ ID NO 22
<211> LENGTH: 1383
<212> TYPE: DNA
<213> ORGANISM: Homo sapiens
<220> FEATURE:
<221> NAME/KEY: SITE
<222> LOCATION: (556)
<223> OTHER INFORMATION: n equals a,t,g, or c
<221> NAME/KEY: SITE
<222> LOCATION: (562)
<223> OTHER INFORMATION: n equals a,t,g, or c

<400> SEQUENCE: 22

```
ggtgcaaaga acatagaata ttttgaaaaa cataagactg aaaatacatt ctgagctcac    60
ctttgcttga tagtttggct gaacataaaa atctagtttg gaaatctttt ttgcctagaa   120
attttatgac attttcccca ttgtcttcta ccttctggtg gtcttccaga tttcactgtg   180
aaatgctgtg gtttgtatct ttacttgtca cttttactgc acactcagtt gaatactctc   240
aatattaaag ctcatgccct ccagtttggg catattttga tgaatatttt gtgaaaattc   300
cttgcctttt ccaacttcta gaagctgcct ctacactttg attctttggg ctctttcttt   360
ttttctccac cttcaaagcc agcagcatag cacttccaaa tttctctctg cttctgccct   420
agtactaata ttaagtgagg tctccttgtt tcaaagaaaa tggatgtcaa taaagcactg   480
atgcatcagc aaatagtttt aaactccctg gakgwatatc tagtcttcca gaatacctct   540
cttctctact agagtntaga tntattcatt tactcatcay tcmatcattt aamaaacatt   600
ttctaagaaa ctgctttgcc tttgggactg ccctaggywc tggaatataa tagtgagcat   660
gacattgttt gaacttttaa agcagcttac agttaaatag gtgaaacaaa ccaatataca   720
aggacttgcc atatataaca aatacttttg tagagctaag tatagaatgt aaaagaaagg   780
aaatagctca gtcttggagg gggaaaggag atttctcagt gacctgggac acttgaagaa   840
taagtaggag tcatccaaac aaagaacagg caaagctatt gatatagcat gtacaaagac   900
ccagaagtga aagaaggtat agtattttca gagaaattac tcatgtaatc tgagacttag   960
acaagtagag acagagatga atctggagag gcaaagtaat gaaggacctt atgaattggg  1020
tgaccataga atatactatc caaacctata cacttttgaa aatgaaagag atacccgggt  1080
gcagtggctc atgcctgtaa tcccagcact ttgggaggcc aagcaagaca ggccgatcat  1140
ctgaggtcag gagtttgaga ccagcctgac caacatggtg aaaccccatc actactaaca  1200
ttacaaaatt agccaggcat ggtagctcac acctgtattc ccagctactc aggaggctga  1260
ggtagtagaa tcgcttgaac ccgggaagtg gaagttgtca gtgagccaag attgtgccat  1320
tgcactctag cctgggtggc agagcgaaac tctgtctcaa aaaaaaaaaa aaaagggcg   1380
gcc                                                                1383
```

<210> SEQ ID NO 23
<211> LENGTH: 1513
<212> TYPE: DNA
<213> ORGANISM: Homo sapiens
<220> FEATURE:
<221> NAME/KEY: SITE
<222> LOCATION: (1502)
<223> OTHER INFORMATION: n equals a,t,g, or c
<221> NAME/KEY: SITE
<222> LOCATION: (1512)
<223> OTHER INFORMATION: n equals a,t,g, or c

<400> SEQUENCE: 23

```
gcagaatgtt taaaggcctt aggtatatgg agcgagctgc tgaaastatg gcaaggtggt      60
tgatctggcc ccactccatt tggatgcaag gatttcactt tctacccttc agcagcagct     120
gggccagcct gagaaagctc tggaagctct ggaaccaatg tatgatccag atactttagc     180
acaggatgca aatgctgcac agcrggaact gaagttattg cttcatcgtt ctactctgtt     240
gttttcacaa ggcaaaatgt atggttatgt ggataccta cttactatgt tagccatgct     300
tttaaaggta gcaatgaatc gagcccaagt ttgtttgata tccagttcca agtctggaga     360
gaggcatctt tatcttatta agtatcgag agacaaaata tcagacagca atgaccaaga     420
gtcagcaaat tgtgatgcaa aagcaatatt tgctgtgctc acaagcgtct tgacaaagga     480
tgactggtgg aatcttctgt tgaaggccat atactcctta tgtgacctat cccgatttca     540
agaggctgag ttgcttgtag attcctcatt ggaatattac tcattttatg atgcaggca     600
aaacgcaaa gaactagaat actttggtct gtctgctgca attctggaca aaaatttcag     660
aaaggcatac aactatatca ggataatggt aatggaaaat gtcaataaac ccagctctg     720
gaacatttc aatcaagta ccatgcactc ccaagatgta cgacatcatc gcttctgtct     780
ccgttgatg ctgaaaaacc cagaaaatca tgccctatgt gtcttaaatg acacaatgc     840
atttgtatct ggtagtttta agcatgcgct tggacagtat gtgcaagcct tcgcactca     900
ccctgacgaa cctctctata gcttctgtat aggcctaacc tttattcata tggcatctca     960
gaagtatgtg ttacggagac atgctcttat tgtacagggc ttttcctttc ttaatcgata    1020
cctcagttta cgtgggccct gccaggaatc attctacaat ttgggccgtg gccttcatca    1080
gttgggggctg attcatcttg caatccacta ttatcagaag gccctggagc tccctccact    1140
tgtggtagag ggtatagaac ttgaccagtt agacttacga agagatattg cctacaactt    1200
gtctctcatc tatcagagca gtgggaatac cggaatggct caaacgcttt tgtataccta    1260
ttgttctata taaagcaccg caactgagaa cagagcaatg gcagctgctg tgtgaggacc    1320
agtgtcttct gtctcagggc ttattatttg taactccaaa atagaaatga caatttcaga    1380
attacctaac aaacagtgta tttattttta atatgtgata atgatcttgt ggtatatatg    1440
caaaattatt cctacaaaaa aaaaaaaaa aaactcgtag ggggggcccg gtacccaatc    1500
cnaattttc cnc                                                       1513
```

<210> SEQ ID NO 24
<211> LENGTH: 1044
<212> TYPE: DNA
<213> ORGANISM: Homo sapiens

<400> SEQUENCE: 24

```
ggattttcag agacaaaggt ccaagttagg agacgtaatt actcagtgct ttgaagggac      60
atccaaggtg ctcactctta gccatagccg ttggtttcct ggatgctgac tgtgaagatt     120
ctaaagtgct tcctagggtg ggcggtggtg gcaggaggcc ttggacgag tcaggccaga     180
cccagcctcc tgtttaatag gctgagccca agcgtccctc agatgcgaat ccaacagcct     240
tggtgagttg taagatttca tggaaacttt ccctgacttc tgtctcccc ttgctcccca     300
ttacctggga aaggcagctt tgtgggccat gtgtcccgga agggcctggg ctggctgtgg     360
cccagtgctc aggaccagcc atcttggccc tcacagcgcc ctgccagtt ggtgtaatat     420
ttgtyttcaa gccattgttg gagcaggcag gcaaggggg ctttctgagg atccaacgtg     480
tgccagccac tgggatacaa agacaggcct ggttcctagc tgtggggctg ggaagggtat     540
```

```
ctgacatcaa tggtggcacc tggcagagga cacacagaca acagcaggca gcatggactt    600
ttatgtttgt agcttgagct ggttttaatt ggaagctctg tgatttacat aatcacttac    660
aatctctgta aataaggaac tatttatgag gaattgtaaa tttcctctct cccccttctt    720
accctgtctg tgatcttgtc tgtgatgcag taatgatatt ccactctagg ttcccatgat    780
cagtggtgaa atatagtgat tttcacctgt gcttccattc tgaagttctg gaaagaagta    840
ctggatggac tgaagtccag gacaacgtyc caaagaaagg cagagtccag gtaggcttgg    900
aggaccaagc cctggatgag cactggaggg cagaggcctc agtgtccagc actgtgccct    960
gcacatggaa agcccctacg tttgtggaat gaatgaataa taaaaatgtt ttcataagtg   1020
aaaaaaaaaa aaaaaaaact cgag                                         1044
```

<210> SEQ ID NO 25
<211> LENGTH: 2575
<212> TYPE: DNA
<213> ORGANISM: Homo sapiens

<400> SEQUENCE: 25

```
ccacgcgtcc gcgggcaccg gccgacatgg cggcagcggt ggcggctgcg ctggcgcggc     60
ttttggcggc ctttctgctc ctcgcggccc aggtggcctg tgagtacggc atggtgcacg    120
tggtctccca ggccgggggc cccgaaggca agactactg catcctctac aacccgcagt    180
gggcccatct tccgcacgac ctcagcaagg catctttcct gcagctgcgc aactggacgg    240
cctccctgct ctgctccgca gccgacctcc ccgcccgtgg cttcagcaac cagatcccgc    300
tggtggcgcg ggggaactgc accttctatg agaaagtgag gctggcccag ggcagcggag    360
cacgcgggct gctcatcgtc agcagggaga ggctggtccc ccgggggggt aataagacgc    420
agtatgatga gattggcatt cccgtggccc tgctcagcta caagacatg ctggacatct    480 tcacgcgttt cggccgcacg gtgagggcgg cgctgtatgc gcctaaggag ccggtgctgg    540
actacaacat ggtcatcatc ttcatcatgg ctgtgggcac cgtcgccatc ggcggctact    600
gggccgggag tcgggacgtg aagaaaaggt acatgaagca caagcgcgac gatgggcccg    660
agaagcagga ggacgaggcg gtggacgtga cgccggtgat gacctgcgtg tttgtggtga    720
tgtgctgctc catgctggtg ctgctctact acttctacga cctcctcgtg tgcgtggtca    780
tcgggatctt ctgcctggcc tccgccaccg gcctctacag ctgcctggcg ccctgtgtgc    840
ggcggctgcc cttcggcaag tgcaggatcc ccaacaacag cctgccctac ttccacaagc    900
gcccgcaggc ccgtatgctg ctcctggcgc tcttctgcgt ggccgtcagc gtggtgtggg    960
gcgtcttccg caacgaggac agtgggcctg gtcctccag gatgccctgg gcatcgcctt   1020
ctgcctctac atgctgaaga ccatccgtct gcccaccttc aaggcctgca cgctgctgct   1080
gctggtgctg ttcctctacg acatcttctt cgtgttcatc acgcccttcc tgaccaagag   1140
tgggagcagc atcatggtgg aggtggccac tgggccctcg gactcagcca cccgtgagaa   1200 gctgccccatg tcctgaagg tgcccaggct gaactcctca cctctggccc tgtgtgaccg   1260
gcccttctcc ctcctgggtt tcggagacat tttggtgcca gggctgctgg tggcctactg   1320
ccacaggttt gacatccagg tacagtcctc caggtgtatac ttcgtggcct gcaccatcgc   1380
ctatggcgtt ggcctccttg tgacattcgt ggcactggcc ctgatgcagc gtggccagcc   1440
cgctctcctc tacctggtgc cctgcacgct ggtgacgagc tgcgctgtgg cgctctggcg   1500
ccgggagctg ggcgtgttct ggacgggcag cggctttgcg aaagtcctac ctccatctcc   1560
```

```
gtgggcccca gcaccagccg acggcccgca gcctcccaaa gactctgcca cgccactctc      1620
cccgcagccg cccagcgaag aaccagccac atcccctgg  cctgctgagc agtccccaaa      1680
atcacgcacg tccgaggaga tgggggctgg agccccatg  cgggagcctg ggagcccagc      1740
tgaatccgag ggccgggacc aggcccagcc gtcccggta  acccagcctg gcgcctcggc      1800
ctaggggagg ggtgagacgc tcgctgccgt gcccgccaca ccaagatgtt ggggctgcct      1860
ggcgcccatg gagacagaca gacagacgct tgtccccgg  gaccgaggcc tgtgccgtcc      1920
ccacccgccc caacatggtg cttatccttg ccgagacccc tgcagtcgtg cccgcgccca      1980
gcccagctgc cccggctgca cgcctgctgc tcccagctcg cccggctgcc acaagctttc      2040
tgcgggtcca tcctccccgc aggaggaggg gtccgtcctt cgcaggcctt gcccggcctc      2100
tctgcagacc ctcaagcgtc gtctgcatga gtgagcaggc gtgggtggac tttggccgcg      2160
gccacacttg gtgctcacca gctgcttcgg ccttcaggtg acctcctcc  ccacggcatc      2220 ctgctctccg ggtggaagag cagcttttg  tctcccagaa ggcatcgctt ttccctcttg      2280
agcagatcgg agcccctggg aggtttggaa gctgcctcca agcctaggac acggaccggt      2340
ggccggggcg gcctctggcc cctgacgctg gctgagacag gcccgtgggg cggggttttg      2400
gggcgtgaac aaggctggca gtaagtggac aagctgctcc cctggctaag gccctgccct      2460
gccctcagcc agaggtgcct ggccatgcct gcacactcct ccccatttta ataaatggtc      2520
gcaacttcaa aaaaaaaaaa aaaaaaaaaa aaaaaaaaaa aaaaaaaaaa aaaaa           2575

<210> SEQ ID NO 26
<211> LENGTH: 718
<212> TYPE: DNA
<213> ORGANISM: Homo sapiens
<220> FEATURE:
<221> NAME/KEY: SITE
<222> LOCATION: (21)
<223> OTHER INFORMATION: n equals a,t,g, or c

<400> SEQUENCE: 26
aactagggat cccccgggct ncaggaattc gccactggrg ccaaagtgag agtccagcgg        60
tcttccagcg cttgggccac ggcggcggcc ctgggagcag aggtggagcg accccattac       120
gctaaagatg aaaggctggg gttggctggc cctgcttctg ggggccctgc tgggaaccgc       180
ctgggctcgg aggagccagg atctccactg tggagcatgc agggctctgg tggatgaact       240
agaatgggaa attgcccagg tggaccccaa gaagaccatt cagatgggat ctttccggat       300
caatccagat ggcagccagt cagtggtgga ggtaactgtt actgttcccc caaacaaagt       360
agctcactct ggctttggat gaaattcgac tgcttaaaaa ggaccttggt ttaatagaaa       420
tgaagaaaac agactcagaa aaaagatttg gctctgtctc atttggaaga agctgcaggc       480
ttattcccca tgcacttgct tcctggctgc aaaccttaat actttgtttc tgctgtagaa       540
tttgttagca aacagggagt cctgatcagc acccttctcc acatccacat gactggtttt       600
taatgtagca ctgtggtata catgcaaaca tccgttcaaa atctgagtcg gagctaaaaa       660
aaaaaaaaaa aaaactcrag gggggcccg  agtacccaat tsgccctaga agaggcga       718

<210> SEQ ID NO 27
<211> LENGTH: 654
<212> TYPE: DNA
<213> ORGANISM: Homo sapiens
<220> FEATURE:
<221> NAME/KEY: SITE
<222> LOCATION: (613)
<223> OTHER INFORMATION: n equals a,t,g, or c
```

<221> NAME/KEY: SITE
<222> LOCATION: (623)
<223> OTHER INFORMATION: n equals a,t,g, or c

<400> SEQUENCE: 27

| | | | | | |
|---|---|---|---|---|---|
| ggtcgaccca | cgcgtccggt | catggccatc | cagagcctgc | acccttgccc | ctcagagctc | 60 |
| tgctgcaggg | cctgcgtgas | yttttaccac | tgggcgatgg | tggctgtgac | gggcggcgtg | 120 |
| ggcgtggccg | ctgccctgtg | tctctgtagc | ctcctgctgt | ggccgacccg | cctgcgacgc | 180 |
| tcccgaggcg | gagaacaccg | aacacccagt | gaaggtgagg | ggatcagcac | ggcgccgcca | 240 |
| ccgtgctgga | acgagactca | gccacaagga | ggtgcgaagc | tctgacccag | gccacagtgc | 300 |
| ggatgcacct | tgaggatgtc | acgctcagtg | agagacacca | gacacagaag | ggtacgctgt | 360 |
| gatcccactt | ctatgaaatg | tccaggacag | accaatccac | agaatcaggg | agaggattcg | 420 |
| tgggtgccgg | gactggggag | ggggacctgg | gggtgactag | gtgacataat | ggggacaggg | 480 |
| ctgccttctg | ggtgatgaga | atgttctgga | atcagatggg | atggctgcac | ggcgtggtga | 540 |
| aggtactgaa | cgccacctca | ctgtaagacg | gtagattttg | tattttacca | caataaacaa | 600 |
| aacaaaacaa | aanmaaaaaa | aanaaaaaaa | aaaaaaaaaa | aaaaaaaaaa | aaaa | 654 |

<210> SEQ ID NO 28
<211> LENGTH: 1445
<212> TYPE: DNA
<213> ORGANISM: Homo sapiens

<400> SEQUENCE: 28

| | | | | | |
|---|---|---|---|---|---|
| ggcacgaggg | atttgaacaa | gatcattaga | attcaaaaaa | caccagaaat | gaaagatctt | 60 |
| tcctgaagct | gtttaggaat | attcatgata | taccottaac | tgttctagag | aacaaaatgc | 120 |
| gtctgtgctc | cttcacaaaa | gtccctatga | atttgtttct | caatgtgatc | cttcttaagt | 180 |
| tctataactt | tttgttttca | ttaattttag | gaaaatcctg | ccttgcttcg | ttgggcctat | 240 |
| gcaagaacaa | taaatgtcta | tcctaatttc | agcccactc | ctaaaaactc | actcatggga | 300 |
| gctctgtgtg | gatttgggcc | cctcatcttc | atttattata | ttatcaaaac | tgagagggta | 360 |
| agtattcaga | ccagatgttt | agtatttgag | tgataggttc | actttctagg | gaccagctgc | 420 |
| agctccttct | cttgaagatt | gccaccagtg | ccctcccac | cttggggctg | tcctctgcct | 480 |
| tcccttcctc | tcttcttta | tctttattcc | tttccagcag | gagttaaaac | agaaagtttt | 540 |
| cagtcacctt | tgtctatttt | tgttagttca | tttgttttt | aaaaagatga | tgtttattgg | 600 |
| gttaagtatt | agcagaatac | ataaatcatt | tagtacgttt | cctgtttgcg | tgaattctat | 660 |
| ttatgttggt | cacattttgc | aaattaatgt | taaaacctat | taatactcta | cgggacagag | 720 |
| aagcacaagc | tgcctgtgtg | gggaatagct | gccgtcagca | gcctgggtat | atgattggag | 780 |
| agaaagtcaa | gctgatcttt | ggcaccaaac | cattccacat | ctggtactaa | accctgagct | 840 |
| gcagccccca | ggcttgtgtt | gccactggag | cccactcgtc | tagctttgtc | tttaactggc | 900 |
| ccatctgcat | tccattaga | gttcgtgtat | tttgattatc | tggtgaatga | tctacttaac | 960 |
| agaaaggtag | tccacattt | cccagaaagt | gttttgcattt | tgctttcaat | atatggtttt | 1020 |
| atgggataat | atatttctaa | tgactaaaat | gtgagtaaga | tgtttttgaa | taggagcatt | 1080 |
| ttcttactgt | gtctttagtt | cctcggatta | ctgtttcttc | gcacactccc | tgggctttag | 1140 |
| acagtgggat | tgcaattagg | tttggagtgt | tcattctgt | ttgtcagttg | tacggtgggt | 1200 |
| tgtgccaaaa | tgcagttttt | cttaccttt | ttattttattt | atttttatct | aatatagcca | 1260 |
| actggcagaa | tatattgtct | ttaatgtact | ttttttctgt | ctttacagga | taggaaagaa | 1320 |

-continued

| | |
|---|---|
| aaacttatcc aggaaggaaa attggatcga acatttcacc tctcatatta agtctggcaa | 1380 |
| tgatgactat atgtattcct gcctaaataa atcatctatt aatcattaaa aaaaaaaaaa | 1440 |
| aaaaa | 1445 |

<210> SEQ ID NO 29
<211> LENGTH: 2020
<212> TYPE: DNA
<213> ORGANISM: Homo sapiens

<400> SEQUENCE: 29

| | |
|---|---|
| ccacgcgtcc ggggtgaggg caacagatgc tggacccagg gagctctctg ccacaggatg | 60 |
| atggtggccc ttcgaggagc ttctgcattg ctggttctgt tccttgcagc ttttctgccc | 120 |
| ccgccgcagt gtacccagga cccagccatg gtgcattaca tctaccagcg ctttcgagtc | 180 |
| ttggagcaag ggctggaaaa atgtacccaa gcaacgaggg catacattca agaattccaa | 240 |
| gagttctcaa aaatatatc tgtcatgctg ggaagatgtc agacctacac aagtgagtac | 300 |
| aagagtgcag tgggtaactt ggcactgaga gttaacgtg cccaacggga gattgactac | 360 |
| atacaatacc ttcgagaggc tgacgagtgc atcgaatcag aggacaagac actggcagaa | 420 |
| atgttgctcc aagaagctga agaagagaaa agatccgga ctctgctgaa tgcaagctgt | 480 |
| gacaacatgc tgatgggcat aaagtctttg aaaatagtga agaagatgat ggacacacat | 540 |
| ggctcttgga tgaaagatgc tgtctataac tctccaaagg tgtacttatt aattggatcc | 600 |
| agaaacaaca ctgtttggga atttgcaaac atacgggcat tcatggagga taacaccaag | 660 |
| ccagctcccc ggaagcaaat cctaacactt tcctggcagg gaacaggcca agtgatctac | 720 |
| aaaggttttc tattttttca taccaagca acttctaatg agataatcaa atataacctg | 780 |
| cagaagagga ctgtggaaga tcgaatgctg ctcccaggag gggtaggccg agcattggtt | 840 |
| taccagcact cccctcaac ttacattgac ctggctgtgg atgagcatgg gctctgggcc | 900 |
| atccactctg ggccaggcac ccatagccat ttggttctca caaagattga gccgggcaca | 960 |
| ctgggagtgg agcattcatg ggatacccca tgcagaagcc aggatgctga gcctcattc | 1020 |
| ctcttgtgtg gggttctcta tgtggtctac agtactgggg gccagggccc tcatcgcatc | 1080 |
| acctgcatct atgatccact gggcactatc agtgaggagg acttgcccaa cttgttcttc | 1140 |
| cccaagagac caagaagtca ctccatgatc cattacaacc ccagagataa gcagctctat | 1200 |
| gcctggaatg aaggaaacca gatcatttac aaactacaga caaagagaaa gctgactctg | 1260 |
| aagtaatgca ttcagctgt gagaaagagc actgtggctt tggcagctgt tctacaggac | 1320 |
| agtgaggcta tagccccttc acaatatagt atccctctaa tcacacacag gaagagtgtg | 1380 |
| tagaagtgga aatacgtatg cctcctttcc caaatgtcac tgccttaggt atcttccaag | 1440 |
| agcttagatg agagcatatc atcaggaaag tttcaacaat gtccattact cccccaaacc | 1500 |
| tcctggctct caaggatgac cacattctga tacagcctac ttcaagcctt tgtttact | 1560 |
| gctccccagc atttactgta actctgccat cttccctccc acaattagag ttgtatgcca | 1620 |
| gcccctaata ttcaccactg gctttctct cccctggcct ttgctgaagc tcttccctct | 1680 |
| ttttcaaatg tctattgata ttctcccatt ttcactgccc aactaaaata ctattaatat | 1740 |
| ttctttcttt tctttccttt tttttgagac aaggtctcac tatgttgccc aggctggtct | 1800 |
| caaactccag agctcaagag atcctcctgc ctcagcctcc taagtacctg ggattacagg | 1860 |
| catgtgccac cacacctggc ttaaaatact atttcttatt gaggtttaac ctctatttcc | 1920 |

-continued

| | |
|---|---|
| cctagccctg tccttccact aagcttggta gatgtaataa taaagtgaaa atattaacat | 1980 |
| ttgaaaaaaa aaaaaaaaaa aaaaaaaaaa aaaaaaaaaa | 2020 |

<210> SEQ ID NO 30
<211> LENGTH: 1083
<212> TYPE: DNA
<213> ORGANISM: Homo sapiens

<400> SEQUENCE: 30

| | |
|---|---|
| aattcggcag agccctgaac cccgcacccc accctcgagg ccagaaatcg gttgcctctg | 60 |
| gggacctgag aagcgagacc actcggcgcc ctgacttgca aagttggggt ctttattggc | 120 |
| ctccgggatt ctgctcctgg cggtttctcc aggctggtga tgggcaagcc gggtgtacca | 180 |
| agtccaggat gcacatgagg agcgtttgta gcagtcactg aatcacctca tgactagcgg | 240 |
| ggcaggcctc taattcaccg caggatttcc ggtaggttgg attgtggggt tggtgtttgc | 300 |
| actccaaaga gktgctgtga tttccctgta tctgtctttc tggcttgtta gatcttctca | 360 |
| tttggcgtcc tttctccgaa gagttaacca agacgtttgg catggtttcc ttgctttcct | 420 |
| cctatctttt gctgctagag ctgctttcga aaagaagtct tttcttgcag tggtatcttt | 480 |
| tctttgggtt acagtgttgt tcatcctttc tttgccgaaa gaatgaatcc cagtgcttca | 540 |
| caaggttaaa ggaaagatct gctggtagtg tttagtcttt gttctgagct gatatgtgtt | 600 |
| agtagctttt tgttttttaaa ttttattagt aaaatttcac cagtgaacca gaagctcttt | 660 |
| ttttctgttg tgaaatgcta gctttaagat ttctgagaac tttgtgtcaa agaaatcttt | 720 |
| gaaaagttac tgaagtatac agagaggttc acaattttaa atgtgcaggt ggtccgggcg | 780 |
| cggtagatca cacctgtaat cccagcactt tgggacgcca aggtgggcgg atcacttgag | 840 |
| cccaggattt ccagaccagc ctgggcaacg tgccaaaacc ctatctctac taaaattaca | 900 |
| aaagttagct gtgtgtggtg gtgtgtgcct gtagtcccag ctacctggta ggctgaggtg | 960 |
| ggaggatcac cagagcccag gaggttgaga ttgcagtgag ccgtgatcat ggcagtgcac | 1020 |
| tcccgcctgg gtggcagagt gagaccctgt ctccaaaaaa aaaaaaaaaa aaaaaactc | 1080 |
| gag | 1083 |

<210> SEQ ID NO 31
<211> LENGTH: 1580
<212> TYPE: DNA
<213> ORGANISM: Homo sapiens
<220> FEATURE:
<221> NAME/KEY: SITE
<222> LOCATION: (1513)
<223> OTHER INFORMATION: n equals a,t,g, or c
<221> NAME/KEY: SITE
<222> LOCATION: (1542)
<223> OTHER INFORMATION: n equals a,t,g, or c

<400> SEQUENCE: 31

| | |
|---|---|
| gctggggaag atgctgcgtc cagcgttacc gtggctgtac cttggcctct gcagcctcct | 60 |
| ggtgggggag gcagaggccc cgagcccgt ggatccgctg agcggagcc ggccgtacgc | 120 |
| ggtgctgcga gggcagaacc tggtgttgat gggaaccatt tcagcatcc tgctggtgac | 180 |
| tgtcatcctt atggcatttt gtgtctacaa gcccattcgg cgtcggtgac agccagacaa | 240 |
| gttcttcaat gagtatttgg gaataggata agttgtgttg cacacaggcc agtggagaag | 300 |
| ttggaaccaa aactttccta cttggaaatg acctttggtc tggacagttg gtaaatgcta | 360 |
| aatgaattag aagaaaacat gtactagaca ttattttttc ctaacactgt agcgcaaata | 420 |

-continued

```
attggcccct gagtccgctt ctcagtgttt ctgactgtac ttgttaaaag taagacctga      480
aagctccaaa ggtcagtgta aagatggagt gttcatgaga aagaaaacat ggtaaccttg      540
tgagtgcctg taagaaccac actgtaaaga actcatcatt aatgcttgaa atgttatta      600 agaaggagac ttaccatgca gacattccct atttaagaac catttggtta cagtgggtta      660
agaatcacag attttttttt ttaatctcac ctgagttagc ctagaatgcg ctggttgcaa      720
agtggtgtca gctgtgggga tcttgggccc tcgttcctca cctgcatcct gccctgcact      780
caggtgctcc ccctgaagtc aggtcacat caggtagacc tgttactata tgcacctttg       840
gcctggaatg ctctgaagtt ggactggaaa tgttactagg ttggcctgtt acaaaaagga     900
ccccatcctg cttaaacaca ttgatctccc ttgccctgca tttgagtctt tctagcccac     960
ggtctgaaac ttgaggcagc tttccagatt tggaatgtaa aaggctcagt gggcactctg    1020
ttcatccctg ggtggggagg gcccagccaa cagaagtgca tgtccactgt gcgggccagt    1080
gtgtgtttac acaaatttca tctcagcttt gaaaatgctg ctattagttt ccactgttgg    1140
tgaactggat tttttcctcc tattgaaatg atactttcat acttataaag ctgtcgtcaa    1200
tatttatttc aaggtgctag atttaatttt gttattaaat tgaaatgctt atcttgtgtt    1260
caagcacagc actgatttta acaacctgca tttaatgtga agtaaccgaa gtaggatact    1320
gtaactgtgt aaggattttg tttgtaatct tgtaacattg aaccattgaa atgttcagtt    1380
ctttgctttt gagcaaaacg tcaattaaaa ctaaagtaaa atcctatata ttgttttact    1440
ccaccagtta tttcccaagt gtttgaaatg caggtgtgtg tctgaatttg gatctaatcc    1500
acttaaagga ggnctgtgga ggggaaattc cttttttgag gncgggtttt gggtcccctt    1560
gcccggggaa agggttcccg                                                1580
```

<210> SEQ ID NO 32
<211> LENGTH: 796
<212> TYPE: DNA
<213> ORGANISM: Homo sapiens
<220> FEATURE:
<221> NAME/KEY: SITE
<222> LOCATION: (748)
<223> OTHER INFORMATION: n equals a,t,g, or c

<400> SEQUENCE: 32

```
tcggcccgag aagaaatgtg acgcactctc accaagatgc tgaagctgac attcatcaat       60
aagcagctgt gcatccacta ggcatttggt aaatgttaac ttatctaccg aggtggtgtt      120
ttcttagcct cccacctcct tgctgtggag cagcttcatg taccatgatg catattcaga      180
tcattcttaa tactcatatt ttgatagaga ggttttttagg ttttcttta aaccaagttt      240 attgagataa actactttgg taggatatgg aacttaggaa taatggtatg aaactagaca      300 gcttttttt ttttattaca ctttaagttc tgggatatgt gttcagaaca tgcaggtttg      360
ttacataggt atacacgtgc catggtggtt tgctgcaccc atcaacctgt catctgtatt      420
cggtgtttct cctaattcta tcccwcccct acccccctgc cccaaaaag gccccagtgt      480 gtgatggtcc cctccctgtg tccatgtgtt ctcattgttc aactcccact tatgagtgag      540
aacatgaggt gtttggtttt tcttcctgt gttagtttgc tgagaatgat ggcttccagc      600
ttcatccatg tccctkcaaa ggacatgaac tcagtccttt tttatggctg catagtattt      660
cgtggtatat aagtgccaca ttttctttat ycagtctayc attgggttg gttccaaatc      720 tttgctattg tgaatagtgc cgcaatanac atacgtgtgc atgtgtcttt aaaaaaaaaa      780
aaaaaaaaaa ctcgag                                                     796
```

<210> SEQ ID NO 33
<211> LENGTH: 1256
<212> TYPE: DNA
<213> ORGANISM: Homo sapiens

<400> SEQUENCE: 33

| | | | | | |
|---|---|---|---|---|---|
| ctatgttcca | tcattccttc | ccaaagccac | cggaagcatt | ccttctagga | aaggtggagt | 60 |
| cggtagtgag | aagccggagg | tgccctaca | gacatacaag | gagattgttc | actgctgyga | 120 |
| ggagcaggtc | ttaactctgg | ccactgaaca | gacctatgct | gtggagggtg | agacaccat | 180 |
| caaccgcctg | tccctgctgc | tctctggccg | ggttcgtgtg | agccaggatg | ggcagtttct | 240 |
| gcactacatc | tttccatacc | agttcatgga | ctctcctgag | tgggaatcac | tacagccttc | 300 |
| tgaggagggg | gtgttccagg | tcactctgac | tgctgagacc | tcatgtagct | acatttcctg | 360 |
| gccccggaaa | agtctccatc | ttcttctgac | caaagagcga | tacatctcct | gcctcttctc | 420 |
| ggctctgctg | ggatatgaca | tctcggagaa | gctctacact | ctcaatgaca | agctctttgc | 480 |
| taagtttggg | ctgcgctttg | acatccgcct | tcccagcctc | taccatgtcc | tgggtcccac | 540 |
| tgctgcagat | gctggaccag | agtccgagaa | gggtgatgag | gaagtctgtg | agccagctgt | 600 |
| gtcccctcct | caggccacac | ccacctctct | ccagcaaaca | ccccttgtt | ctacccctcc | 660 |
| agctaccacc | aactttcctg | cacctcctac | ccgggccagg | ttgtccaggc | cagacagtgg | 720 |
| catactggct | tctagaattc | ctctccagag | ctactctcaa | gttatatcca | ggggacaggc | 780 |
| cccttttggct | ccaacccaca | cgcctgaact | ttaaggatca | ttggactatc | ttctctgtgg | 840 |
| ccagcgcagc | tctcttctgt | gttcacagaa | tggccactga | taggcaygcc | tcttttccca | 900 |
| cccactggaa | ggctcacagg | caaggtgaga | gaggacacag | aaggtgccaa | cactgtcgct | 960 |
| acagtaagga | cctgaagtga | ctttgagaaa | ttcaccctca | caaaccttcc | ttcaggagca | 1020 |
| ggcattggta | gtgcagaggc | acagattccg | tcctttacca | gctgcagaat | cttgggcaag | 1080 |
| ttacatagcc | tctgtgagcc | tcatcggtaa | acagtgggg | ttatgaaacc | cacctcacag | 1140 |
| ggttgttgtg | aggatccaat | gagttgattt | aggtaagcac | ctagcacatg | ccgtggcacc | 1200 |
| aagtaagcac | tcaataaatc | actcaactcc | ttaaaaaaaa | aaaaaaaaaa | ctcgag | 1256 |

<210> SEQ ID NO 34
<211> LENGTH: 1064
<212> TYPE: DNA
<213> ORGANISM: Homo sapiens
<220> FEATURE:
<221> NAME/KEY: SITE
<222> LOCATION: (462)
<223> OTHER INFORMATION: n equals a,t,g, or c
<221> NAME/KEY: SITE
<222> LOCATION: (1047)
<223> OTHER INFORMATION: n equals a,t,g, or c
<221> NAME/KEY: SITE
<222> LOCATION: (1048)
<223> OTHER INFORMATION: n equals a,t,g, or c
<221> NAME/KEY: SITE
<222> LOCATION: (1050)
<223> OTHER INFORMATION: n equals a,t,g, or c

<400> SEQUENCE: 34

| | | | | | |
|---|---|---|---|---|---|
| cttcagcctg | ggcaacagag | caagaacctg | tctcagtcaa | tcaataaatg | tatgtatata | 60 |
| tatatatgta | tatatgtcag | accaccgtct | gaaattgctg | ttcatgattg | gaaatcgaac | 120 |
| tggaaacccg | aaggcaggag | atgtgtgctc | ccttgggatg | tatggggaaa | tcacacagag | 180 |
| ctgttagtac | ttcagtcatg | ggatttgctc | tcatgctatg | catatgggcc | tcacaacttg | 240 |

```
taaatgccac tggaagatgg cttatctaag gttccttatt ttgtggtctt tcccccttag    300
ttctgcagtg agtggggcaa agcgtgtcac tgaccttttg aatggaaaac actggaagcc    360
ttagcgttct taattcctga aatgttcatt tttwcttcta agcaactggg cttcasagga    420
gattagggca ggcaataaca gtgttgacac cagggcaact gntttcycct gttatgggat    480
tatwcaacat ctgctttctg ctaagctcca tggaaggcac agaggaaaca cagcagagtc    540
catgccttag agactttgta cctgatgaat tgagtggtat caggacaatg ctatttaatg    600
tttgatccat cccttctcta agcacatctc agatttctgt gctacctgat ttaacccttt    660
cagttcatag aacccagaag gataaggtga aagatagac cgggaaaagt aatgcaagtg    720
gccaagagta gcttccactt caaagttcct catgtgtgtg tgctaacatt gtgacttctg    780
ttcagtcatt gtcagtataa actgtacatt ggaatcattt gtagcttttt aaaaaatgcc    840
tatgcctcac cctagaccta ccacatcaaa atctcaggat agagtctcaa gctaaaaagc    900
ctctatttga gccaggctta ttggcacctg cctgtagtcc cgtactcaga aggctgaagt    960
gagaggatcg cttgaactca ggagtttaac gccagcagag gcaataggc aaaatagcga    1020 gatctcatct ctttaaaaaa aaaaaanntn aaaagggcgg ccgc    1064
```

<210> SEQ ID NO 35
<211> LENGTH: 755
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<221> NAME/KEY: SITE
<222> LOCATION: (733)
<223> OTHER INFORMATION: n equals a,t,g, or c
<221> NAME/KEY: SITE
<222> LOCATION: (734)
<223> OTHER INFORMATION: n equals a,t,g, or c

<400> SEQUENCE: 35

```
natttcccgt tcagttattc cggtgacact atagaaggta cgcctgcagg taccggtccg    60
gaattcccgg gtcgacccac gcgtccgaac tcctgaaaca gtgaggacat ctcacagacc    120
agacaggagc tggggctctg catctcacag cggtgcctgt cagacaggaa gaagtcccgc    180
agaagtggcg tgtgggtcag ggcctgcacg atgcagttca tgaagcatgt gttcccaagg    240
ttgatcagcc cacgcagacc tatggtgcag ttcgaggtga tctttctcct tttcgggttg    300
tgcttcagca gttcaagctc ccgtttggtt ggttcccaag ttgaaaactt ctctccaacg    360
ccttgcattt tccaagcttt tcgctgctcc tccttggcga ttatttccat gtctttgtca    420
tagatgtagt cctggcacag aaaacagtag atgcctccgt acatcagatc aatggccagg    480
ttgtgccgct tcgccttcgc atgctcgtga atatgcttct ttgtgaaaca gccgaagaag    540
acacagtaga ggcaggaatg cagcctgttg aggtggacgc cacagacatg gcagatacag    600
gacttggcct tgcgcttgcg ggcctcagcc gtgccgctcc acacgaagca ctggtagatg    660
gcccgcaggt tctgcttcca gttgtccacc ttgaagctgc ccaggtgcga gcagcccggc    720
ggcgctaccg ccnnctcggc gtccatggcc tcgcc    755
```

<210> SEQ ID NO 36
<211> LENGTH: 604
<212> TYPE: DNA
<213> ORGANISM: Homo sapiens

```
<400> SEQUENCE: 36
ggcctcccaa agtgctggga ttacaggcgt gagcaagatt atatttcttt aataaagaat      60
acgtgacttt tatttaagtt gtcagattta ttggaaatgt tgttcgtaat atcttttgat     120
gtctgtggta cctgtaatga ttcctttttt actactactg ttttttttct ctctctcttc     180
cacccaccat ccccatttac tttattttc catctttata ttttcaggct ctttattggt      240
cagaattctt agttgtagaa aagagagttc acaccaggta ctcttaagca gaaaatgttt     300
tattaagggg cacagacagc acagacagct tacaaaagtg taggggaccc aaacagaaac     360
cctttaattt tactgattag aatggggagc tcaacagagg caactattaa aatgtgcaga     420
aggtattcag aagattgtga gcaggcatat atgagagatt tcattacaag ctctctacag     480
taaccaacca taatgcagaa tagaaattca ttattttgga cttttgctac ctgtcaattt     540
aactgttacg ttttacgga cttgttaaaa agtgattag atagactgtt ttagattttc       600
ctta                                                                   604

<210> SEQ ID NO 37
<211> LENGTH: 812
<212> TYPE: DNA
<213> ORGANISM: Homo sapiens
<220> FEATURE:
<221> NAME/KEY: SITE
<222> LOCATION: (17)
<223> OTHER INFORMATION: n equals a,t,g, or c
<221> NAME/KEY: SITE
<222> LOCATION: (108)
<223> OTHER INFORMATION: n equals a,t,g, or c

<400> SEQUENCE: 37
gaccattttt agccaanctt ggaattaacc ctcacttaag ggaacaaaag ctggagcttc      60
caccgcgttg gcggccgctc tagaactagt ggatccccccg ggctgcanga attcggccac    120
gagaggactt ccccacctca tgcagctatt tgggccgtgg cgtctgaaat ttattatttc     180
agagtcaccc cttratgac cttggcagtg ractgcagtc atctgtttag gcctttccat      240
ggcccacgtc aatgccgtta tttctgtttg ttgcacattt gatttccttg ttgttggcat     300
ttagaaggcc ccctgcttcc cagatcacac cacgggcatg gaccacagag attgcatctt     360
gtgagtctgt agaaatggtc aaggccttgt cctctcttag gtccagagct caggtgaatg     420
cagattttcc cggccatctg tgctgaagtc cctgtgggga ggctcctggc tggtttcctg     480
taggtagaca gctacacgtc ctgcccttca ttggcttctt ttcatgaagc tcctgccatc     540
tacaaaacat gtctcccttc ttgaatcaca tctctgttat tgaagctctg gaagtcaacc     600
gggcgtggtg gctatgccta taatcccagc attttggat gccggggcgg gtggatcacc      660
tgaggtcagg agttcgggac cagcctggcc aacatggcga aaccccgtct ctaatacaag     720
tgcaaaaatt ggccaggcgt ggtggtcact gtgctccagc ctgggtgaca gagcgagctc     780
cgtctcaaaa aaaaaaaaaa aaaaaactcg ag                                   812

<210> SEQ ID NO 38
<211> LENGTH: 1149
<212> TYPE: DNA
<213> ORGANISM: Homo sapiens

<400> SEQUENCE: 38
gtaaaagtta aaaatgtttg cctttatgt tcaggtttta aatcaatcta aaagtatttt      60
tgtatacagt aggaatctaa tttttttttat ccatatgata gtcagttggc cctcctttct    120
```

```
tcagttacct gcagtgcatc aatgtcatca gtcaagtgtc catatatgtg gtgtttctgg      180
gcttttcccc tcttccaatt atcagtgttt atccctgtgt caaaatcaca cagtattaat      240
tattacaact ttatagtaag tcttaatatt tagtagggca agtcttttta tttgataaga      300
gtatctttgc tattcttta cttttactct tctgcatata ttttagaatc agcctgtcaa       360
attcctcaaa agactgtttg gataaatttg gaattacatt caatatagat caatttggga      420
ataaccaaga gttttgggat attgagtctt cattcattaa catagctttt ctcttcattt      480
atttaggtct tattttttca tagagcttta aaaggtttac tataaaatct ttaaggggta      540
aactcttgaa taaggtccag agttaaatag tggagagtta caggtgtctg tttgcccaa       600 acagactgat ggtatttcag ccatctcagg atttggggaa gtcagcacaa ggatcaaaag      660
actgagaaag tttaacttct cctctaggat gttttagta cacacattat atttataagg       720
aaacatattg taaataatag agtgataatg gccacttacc tgagccttat tataaacaga      780
aacaaatatc caaccaatgc catagagcag aagtacagcc tgaaaccaag aagaaaaaga     840
gcaattaaat caggatctca tctaggccaa gcttgaaaag gaagcttatt tcctatttgt      900
cttctgccta atgaatgtgt cattactggg gaccttacca ataaaggtgc ttggatacat      960
tttccagcac agaaacttaa tttgcaggaa catgatcttt acttgtaaaa ggatacattc     1020
ttaattcggg atggttattt gagctgattt tcaaggcatt tatttttaat ttatttgtca     1080
gatgggaata aaggtggttt ataattaaat ttaaaagata gtttaaaaaa aaaaaaaaa     1140 aaactcgag                                                            1149

<210> SEQ ID NO 39
<211> LENGTH: 1087
<212> TYPE: DNA
<213> ORGANISM: Homo sapiens

<400> SEQUENCE: 39
gcccactgga aatgatcttg tttatgtgtt tccttgttta ctgtctgtct tcagtagaat       60
ggaagagcca tcggtatttt gtcttttttt ccccttgtcc attcttatat cctcagcttc      120
tagaacattc cctggaacac agcaagtgtt cagtattgtt catggagtga cagatgtctc      180
agccaagaag gtacaatcac agggaagaat gacttcaact ggtcttgact tcaacctgct      240
tccagcctgg ttcccttctc ccacctccct acagcccaca gaagatcttt ccaaactgg       300 aagtctgtcc aggtcattct tctgctctaa ggctttcagt agctcccct tatccccagg       360 aggaagtcca aatgccttaa caagtgtcaa ggaacacttg gtgagccctg cttttccttgc     420 tagtcactcg tgcacagctg agtctttccc cagagtggat gtcattcatg ctgttcccat      480
tgcctggatt cctgctcctc tccaccccat tcaactgata aactcgtggt tttttttttt     540
tttttttttt ttttgagack gagtctcgat ctatcaccca cgctggagyg cagaggttgc     600
tgtgagctga ggtggtgcta gtgccctcca gcctggatga cagagtgaga ctcggtctca     660
ataaataaat aaataataaa gaagaaacca acccttttga ccccggggtc tcagactttt     720
agccaccaca tcagcgagtt atggtgtttg ttatagcagc tctgggaaac taatgcatgt     780
tttcagtgac atttagccc cttctgaatg gtctggatgg ctggttgaca gctaagttca      840
gacccgatgc aaaagcgcag tctatgtagg aatgtcccct gtggacagct gctgtgtagc     900
caaggtgggt tacatactag gaagggccc tgggggcccc cacagggagc taactctatt     960
gacgggggac ccaggtaaca gatgcaggca tttgctgtga gtcacaagac actgatgtgt     1020
gtttgcttgc ctgggcaaca tagtgagacc ccgtctctat taaaaaaaaa aaaaaaaaa     1080
``` actcgag 1087

<210> SEQ ID NO 40
<211> LENGTH: 1276
<212> TYPE: DNA
<213> ORGANISM: Homo sapiens

<400> SEQUENCE: 40

| gtgagtgtgt | ggcactggtg | gcctggagcc | aaatttagct | tgggtgagag | ttgacaatgg | 60 |
| tagttttcct | tcctcaagcc | cctctgtgcc | cctagagcac | cctggctgtg | gctgcctcct | 120 |
| tcatccaaga | gcagagtcca | tgttgggcca | ggagacttca | gatccatgtc | ctggtgctgc | 180 |
| ctctggcttt | gtctttcctc | agtgggcagg | actgggtctg | ctggtccatc | tttacccttc | 240 |
| tctgagctat | gcagccttgg | cctgctgcgt | ctccggcctg | tattctctcc | ccttcactca | 300 |
| ggccctggga | aaccagccca | gtttctkgca | ggagaggcag | aggaggtcaa | tgcctttgct | 360 |
| ctgggcttcc | tgagcaccag | cagtggtgtc | tctggagaag | atgaagtaga | gcccttacac | 420 |
| gatggagttg | aagaggcaga | gaaaaagatg | aagaagaag | gtgtgagtgt | gagtgaaatg | 480 |
| gaggcaacag | gagcacaagg | acccagcagg | gtagaagagg | ctgagggaca | cacagaggtg | 540 |
| acagaagcag | agggatccca | ggggactgct | gaggctgacg | ggccaggagc | atcttcaggg | 600 |
| gatgaggatg | cctctggcag | ggcagcaagt | ccagagtcgg | cctccagcac | ccctgagtct | 660 |
| ctccaggcca | ggcgacatca | tcagtttctt | gagccagccc | cagcgcctgg | tgctgcagtc | 720 |
| ttatcttcag | agcctgcaga | gcctctgttg | gtcaggcatc | ccctaggcc | ccggaccacc | 780 |
| ggccccaggc | cccggcaaga | tccccacaag | gctggactga | gccactatgt | gaaactcttt | 840 |
| agcttctatg | ccaagatgcc | catggagagg | aaggctcttg | agatggtgga | gaagtgccta | 900 |
| gataaatatt | tccagcatct | ttgtgatgat | ctggaggtat | ttgctgctca | tgctggccgc | 960 |
| aagactgtga | agccagagga | cctggagctg | ctgatgcggc | ggcagggcct | ggtcactgac | 1020 |
| caagtctcac | tgcacgtgct | agtggagcgg | cacctgcccc | tggagtaccg | gcagctgctc | 1080 |
| atcccctgtg | catacagtgg | caactctgtc | ttccctgccc | agtagtggcc | aggcttcaac | 1140 |
| actttccctg | tcccacctgg | ggactcttgc | ccccacatat | ttctccaggt | ctcctcccca | 1200 |
| ccccccagc | atcaataaag | tgtcataaac | agaaaaaaaa | aaaaaaaaaa | aaaaaaaaa | 1260 |
| attgggggg | ggcccc | | | | | 1276 |

<210> SEQ ID NO 41
<211> LENGTH: 2083
<212> TYPE: DNA
<213> ORGANISM: Homo sapiens

<400> SEQUENCE: 41

| gcccttacc | cccaacccca | ggccactggg | cccttcccac | accacttggg | gagctgagaa | 60 |
| gaggaggctg | gagtaaggga | ggacttgatc | atccaagaaa | tacttttat | tgctgggagt | 120 |
| cttctgaacc | tcaccaaact | gaggccagag | ctgagctcct | ggggagtta | attcagaggg | 180 |
| gagaggccag | cacctccctc | ctccatygct | cgctgtgtgc | cttaaactcc | atctcatgtc | 240 |
| cctccccatc | ccctggcttt | ccctcccctcc | ttgccccatc | ctgggccagc | cagcagggct | 300 |
| cctcctctgg | ctcttcagac | ctttcagcca | gtgctgtcag | tgccctgggg | agggaagggc | 360 |
| atccctgagg | cacccgaatg | gtccctcagg | gtgcaggggag | gcagaagcct | ggccacagag | 420 |
| gagcctccta | aggcagcagc | tgcagcaagc | gcaccctctc | cccactctcc | ccacgccaga | 480 |

```
gcggcttcca gagcagatgc tgtttccatc ctcctcgtca aaaccattct cgctgctgag    540
cttgacaatc tgggcaaggc ttgtggggcg cttgacaaac agaatctgcc ctgtgccgcc    600
tggttccgtg gcctccagca tgagcctgca ggcaggcgc tgcgggaacc cagttgtgct     660
gccccagccc atgcctccgg gtctgctgtg catgaatgag tgctcacttg tcccgggttt    720
aggacgtggt caagtgaaca gcaggtctca actgtgctta cttagcccag ttcaaacaga    780
acaaaggaaa aatatagaaa gcaacatctg ttgatcattt aggtttttt  ttaaaccacc    840 atgtcacttt gagtccttca tgggtttttg aacagcattt atcaagaaga aaatgtgggc    900
ttttccccct ctcccgtgtt ttgtttgtcc tgtagataga gggaggaaag ccgtgcagtg    960
gcaggcggga ccccctctgg tggcgggacc ccctcttgcg gtggtcttgc ggggccagcc   1020
gggacctgtc actttattat ttaaggagtg tgtgtgtaga gtcgctggct tattaacagt   1080
attgtgtgtg ggttgggttt ttagtttgtt ccttcttttt gaagtcccct catttcaatc   1140
cttgactctc tctcccctct ccttgcccag ctctgttgaa tgctgctgtg cgcgtgtgag   1200
ggccgctctg cacacaggc  ccttgggttg tgtgaactga aattctccct gtatttgtga   1260
gactcgcagg agtccccatc tgtagcacag gcaatgccag tgccatgctg cagcctcaga   1320
aaccaggcct ctcactccag cagcaggcag aaccgtgtct gtggtcgggt gctgtccaca   1380
gctctgtctg ccttgttctt gggcttgagc tggatagagt tggggtctct tcaccttccc   1440
tgaattcaga acagaccctg tgcctggccc cagtgtgccc aggcaattcc ccaggccctc   1500
attgggagcc cttggtgttc tgagcagcag ggccaggca gcacatgagc agtgcccagg    1560
ggctccctgc gtgaggacgg caaggtgcga tgtatgtcta acttattgat ggcaggcagc   1620
cccctgtgcc ccctaagcct ggccctggtt attgctgagc tctgtgctca gtgctgcggc   1680
ctggccgtgg ctcgtctgtt cctttggggg gcccgggcgg ttgtgggaa  tcagtcttca   1740 cagacagacg tgagccaggc ggaggactcg ttccttgcag aggtcagtcc tcacctgcag   1800 gtgtcgggt  ggrgggggc  aaggagggc  aggcacacac catgtctgac ctgaacccga   1860
ttctggggag catcttcccg ctccggcccc acgacctcca cagggttaca ttgtaatata   1920
tatgccccag ctaacctgtc tgatggtggc atcttcctgc agacatttca aacatgtaac   1980
ttttatatga aaaaaaataa acacagatga aagctgccca aaaaaaaaaa aaaaaaaaa    2040 aaaaaaaaa  aaaaaaaaa  aaaaaaaaa  aaaaaaaaa  agg                     2083

<210> SEQ ID NO 42
<211> LENGTH: 1016
<212> TYPE: DNA
<213> ORGANISM: Homo sapiens

<400> SEQUENCE: 42
taattcggca gagccagcct gggtgcctgt atgcgctcga ggcgggggcg cgggttgcgg     60
acggaggcgc gggaggcggt tctgcgcggc ggggccgta cccgcggcgg agcgaggagg     120
cgagaatgga tcaatggtgt cacggagcac atcgctgacg ctgattgtgt tccttttcca    180
cagattgtct aaagccccag gaaaaatggt ggaaaattca ccgtcgccat tgccagaaag    240
agcgatttat ggctttgttc ttttcttaag ctcccaattt ggcttcaaaa atctgaaggg    300
atctcgtgtt tgctgagtgt tccgtgtgcc agcactagcc taggaggttt tagtctctac    360
aaatatttat acagcaccag acgcgatggc aaagtggata aagcctggtc cctgcccttca   420 aggaggtcgt ggtcttgtgg aggagacaga tggtacttta cctcgtgtgg gccttttattc   480 ctgaatcttg gctaaactct ttaggtttaa cctattggcc tcaaaaatat tgggcagttg    540
```

```
cattacctgt ctacctcctt attgctatag taattggcta cgtgctcttg tttgggatta    600
acatgatgag tacctctcca ctcgactcca tccatacaat cacagataac tatgcaaaaa    660
atcaacagca gaagaaatac caagaggagg ccattccagc cttaagagat atttctatta    720
gtgaagtaaa ccaaatgttc tttcttgcag ccaaagaact ttacaccaaa aactgaactg    780
tgtgtaacca tagtaacacc aagcacgtat ttatttataa gttttttgcca ttataatttt   840 gaccataaat taatttgacc atctctctta ttaatagaga agtaaaaaat gtaagttgac    900
cttctcttag attatgttca atgaatattg taaatgttca agtattgtta atgaatagaa    960
taaatacaat attgcattcc cataaaaaaa aaaaaaaaa aaaaaaaac tcgtag         1016
```

<210> SEQ ID NO 43
<211> LENGTH: 2197
<212> TYPE: DNA
<213> ORGANISM: Homo sapiens

<400> SEQUENCE: 43

```
ggtttgagaa actgtagtac ctagctttct ccaaggctgt tgatgctgg gatcctcttg     60 tgggggggcgt ctgtcaacgt caccatttgg gaagtgcgca ragctcarag cagcgcttcc   120
atgcttcctt ctgcttgggg gccctccag gtagcttctt tcttcttgct atcttttyct    180
ttctgttttc tctcctcttc cccgcacctt gggaggcagg agacccactt kgtkgtgctk   240
gargatgatg agggcgcccc gtgcccagca gaggatgagc tggccctgca ggacaacggg   300
ttcctgagca agaatgaggt gctgcgcaca aggtgtctcg gctcacggag cggctccgca   360
agcgctaccc caccaacaac ttcgggaact gcacgggctg ctcggccacc ttctcagtgc   420
tgaagaagag gcggagctgc agtaattgtg gaaacagctt ctgctctcga tgctgctcct   480
tcaaggtgcc caagtcctcc atgggggcca cagccctgaa gcccagaggg agactgtgtt   540
tgtgtgtgcc tcgtgtaacc agaccttgag caagtgagaa gagaggccag ggtccaacca   600
ggcacccgtc cttggggcca gcagtagacc ccccactctc cccacccctg cccactgtg    660 gtgtgtgctg ggcaaatgtg gcctgaatgc taggtaggct tccccttcct tcctcactct   720
ctccagctgg attctggagc tgttctccat ccatgagagt ggctggcaat ggctgctctc   780
aatcccttga gggagaagag cccctggagg gcctggcatg tttgccctgc tctgcctggg   840
actgagcgag tggacttagg gctgggcagg cagtagccac cagagggcag cagcgaacta   900
ggccaggcct gactggggtc tgaagatcag ggtcagtgtg gctatgcctg ggaattccag   960
acctgaggtt gggaaaagag gttttttctcc tgcagggtac tgggccaggc cctcagcctc  1020
agagagcctg cagaagggct tgggagtgcc acacccatc tctgctgatt gaatgtccct    1080
ccaggcacca ggatctcatc atttccccat cagagggtgt ggccaggcct aacaagacca   1140
tgggtgcttc tagaaacagg gttgaagttc ccagattccc tgagaggaga atgtgtatag   1200
gagggtttgg ctgagtcctt cagcgttaag tggaggaaag cttggggaag ccccaatagc   1260
tggacagacc tcagcctccc ctcgaagaca cctcaattca cagactctca gcccacacaa   1320
tgccccagtg tccccagctc cgctggagca gctgcagggc acttggatca caacttctgc   1380
accctctgtc cagagtctag ggcagtcctc cactggccca gcactccagt ttcctttccc   1440
tgcctcttgt ccaatggagt gggaggccag gtgagtggag cagaggtcct gaagcccttg   1500
acccctgggg gcctgggtag tgtaggatct cgctgggctg ggtcctggat tccagggcta   1560
ttccctggag gacagtctca gttatgggat aaggcccct gggggtctcc atttctttcc    1620
```

| | |
|---|---|
| aacagtttca tgttcactac tggactctta cgggctcagt atctctccct tagccatgag | 1680 |
| ctggctcagg catcccttcc cttccctgga gctgccctgc ctttctcaag tatttattta | 1740 |
| tttattgcat ggttcctggg aacatgtggc acaagtaatg ggatgaggag gaattggggg | 1800 |
| tgggggtctt ctacctagga ctcttccctg gagtcatggg ctgcctggga cccaggaccc | 1860 |
| atgaggggc tgagaggttt ctacactcga ggagcagggg tccagagagg caggctgggg | 1920 |
| aggcaaggga cccatcctag gcccgctttc ttgccgagcc aagcagctta gctggggctg | 1980 |
| tgcagccagg ggcttaccca ggccagtgga ggtgccacag ccctggggag ccagacaggc | 2040 |
| tttggtatcg tatcgcctct gtgtccttt aagagaggag agttcagtac cccgtgcttt | 2100 |
| ctttacactg gagaggaact aaaaggatct ctgtgtctat ggagaattgt caataaaaag | 2160 |
| gcctcaagct tmaaaaaaaa aaaaaaaaaa ctcgtag | 2197 |

<210> SEQ ID NO 44
<211> LENGTH: 1999
<212> TYPE: DNA
<213> ORGANISM: Homo sapiens
<220> FEATURE:
<221> NAME/KEY: SITE
<222> LOCATION: (965)
<223> OTHER INFORMATION: n equals a,t,g, or c
<221> NAME/KEY: SITE
<222> LOCATION: (973)
<223> OTHER INFORMATION: n equals a,t,g, or c
<221> NAME/KEY: SITE
<222> LOCATION: (1110)
<223> OTHER INFORMATION: n equals a,t,g, or c

<400> SEQUENCE: 44

| | |
|---|---|
| ggcacgagcc caaccacaca cctggggaat tgctggcctg acttctgacc cctgactcct | 60 |
| cataccttc ctccagagca tgacatttga ccaccaactg aaacctgacc tctgacccca | 120 |
| gaccactggc cctccccccg ccctgtggtg acttcataaa ggttactagc ttctcccctg | 180 |
| gccttgagac ccacacgatg gccctgctgg ctctggccag tgccgtcccg tctgccctgc | 240 |
| tggccctggc tgtcttcagg gtgcccgcct gggcctgtct cctctgcttc acaacctact | 300 |
| ctgagcgcct ccgcatctgc cagatgtttg ttgggatgcg gagcccaagc ttgaagagtg | 360 |
| tgaggaggcc ttcacggccg ccttccaggg cctctctgac accgaaatca gtgaggagac | 420 |
| catccacact tcatcagtgt cctggggaag gtgcagaggg agggcaggag aggcccagag | 480 |
| ggtcaggctg agggacagac agagagaaac agtcagagga gaaaggctca agaccatga | 540 |
| gaacaacaga gacttaggga cagagagaca cagacagggg asgacagcag ggcaaagact | 600 |
| cagagagggg aggatggaga gtcagagagg ggaagatgga gactcagaga gggggaggat | 660 |
| ggagactcag agagagagga agatggagac tcggaaagat ggagactcag gagtatggag | 720 |
| agtcagagag gggaggatgg acactcggga ggatggagag tcaggaggat ggagactcat | 780 |
| agaaagggga ggatggagag tcaggagagg ttggagactg gagagggaat agagacccag | 840 |
| agagggagg atggagactc agagggtgga agatggagac tcaaagagga tggaaaccca | 900 |
| ggagagagga ggacagagat gaggcagaga ctaggggaag caggatagcg actggtcggg | 960 |
| ggcanagact canggaggat agagacttgg gagggactca ggaagcatag cgactgtggg | 1020 |
| gcaaagagtc agagagggga ggatacagac ttggagggc agagactcag aaacagaatg | 1080 |
| ttcgcattag ggacatggtg ttgcggggan ctgcctcccc cagcccctgc tccctccctc | 1140 |
| accgccagac tatgatgaga gaagccacct gcatgacacc ttcacccaga tgacccatgc | 1200 |
| cctgcaggag ctggctgctg cccagggatc ctttgaggtt gccttccctg atgctgcgga | 1260 |

| | |
|---|---|
| gaaaatgaag aagtctttta cacagcttaa agaagcccag gcttgcatcc ctccctgcga | 1320 |
| aggtctccag gagttcgccc ggcgtttcct ctgcagcggg tgctactcta ggtctgcga | 1380 |
| cctcccgctg gactgcccag ttcaggatgt gacagtgact cggggcgacc aggctatgtt | 1440 |
| ttcttgcatc gtaaacttcc agctgccaaa ggaggagatc acctattcct ggaagttcgc | 1500 |
| aggaggaggt ctccggactc aggacttgtc ctatttccga gatatgccgc gggccgaagg | 1560 |
| atacctggcg cggatccggc cggctcagct cacgcaccgc gggacgttct cctgcgtgat | 1620 |
| caagcaagac cagcgccccc tggcccggct ctacttcttt cttaacgtga cgggccgccc | 1680 |
| ccgcgggcgg agacagagtt gcaggcctcg ttccgggaag tgctgcgctg ggcgccgcgg | 1740 |
| gatgccgagc tgatcgagcc ctggaggccc agcctgggcg agctgctggc caggcccgag | 1800 |
| gctctgacgc ccagcaatct gttcctgctt gcagtcctcg ggccctcgc atcagcgagt | 1860 |
| gcgacagtgt tggcgtggat gttctttcga tggtactgca gtggcaacta acaaaggtat | 1920 |
| cttttcctcct tccctatcct atttccatcc tgaaaataaa gaatatattt caactctaaa | 1980 |
| aaaaaaaaaa aaaaaaaa | 1999 |

<210> SEQ ID NO 45
<211> LENGTH: 1519
<212> TYPE: DNA
<213> ORGANISM: Homo sapiens

<400> SEQUENCE: 45

| | |
|---|---|
| cggcacgagg taaattctgc cttcacccag tatatctttc caatgtagga tgatttattt | 60 |
| ttcattacat ttgttctaag attttgtagt gattactcta gtgtttgtca tgtaaatgtt | 120 |
| agtttatcaa aatcaggctc agttctccag taatatgtgg ttaaatttca gtgatgtaca | 180 |
| cacatatttg tcctctatag ctctattatg ttttgcctt tctggggtac tttgttgcat | 240 |
| atgtaacaac tcagtgttcc acattcaaca atatattctt ataattatta cttttccact | 300 |
| ggtagtcatt tagttcagtt tttatggtgt tatttataaa tataatacat gtatgttaaa | 360 |
| tttttctatg ttgtaggcct aacaatccat tactacttat tactttacac aattgacttg | 420 |
| taaatccata acaaggagaa aggtgaagaa acacatattc agtttgtctt ttccacttat | 480 |
| atagtcttgc atggtgctct ctgcttttc ctgtggattt tgacagactc aataattttt | 540 |
| tttttttttg agatggagtc ttcctctgtt gtcccaggct ggagtgcggt ggctctatct | 600 |
| tggccactgc agcctccacc tgccgggttc aaatgattgt cctgcctcag ccccccaagt | 660 |
| agctgggact acaggcgtgt gccaccacac ccggctaatt tttgtatttt tttttttttt | 720 |
| tgtagagaca gggttttgcc atgtttgcca gggtgctctc aaactcctga cctctagtga | 780 |
| tccaccagcc tcggcctccc aaagtgctga gattacagac gcgagccacc gcacctggca | 840 |
| ctttggtctt gtagggctgg tgtgccagga aaaattctct caatgttcat atttttaagc | 900 |
| ctaggaaaat atttgttttg tctttcattt tgaacatgaa cattgttgga ttctggttaa | 960 |
| ggtgtgtttt ggagcagagc atgatgaggg actgggtgag gggcttccca gtgaaaggag | 1020 |
| gaacagaacc tagcaaaagc aaatatgtct gtttcactcc aatcacttat tacaataacc | 1080 |
| tctattactt aatatcaaaa aaaaagcaat gatcaatatg ttgaaaggga tggaagaagc | 1140 |
| aagtatgatg tttgaccata atagcattca ttgcttggga aactaaagac aaaacaactg | 1200 |
| gaaaactatt aacactgttg gccaggtgtg gtggctcatg cctgtcatcc cagcactttg | 1260 |
| ggaggctggg gtggatggat cgcttgagcc caggagttcg agaccagcct gggcaacatg | 1320 |

-continued

```
gcgaaacctc atctctacaa aaaatacaaa aaattacccg ggtctggtgg tgtgttcctg   1380
tggtcccagc tactcgggag gctgagatgg aaggattgct tgagcctggg aagtcgatgc   1440
tgcagtgagc caggattgca ccactgcact ctagcctgag tgacagagtg agaccctgtc   1500
taaaaaaaaa aaaaaaaa                                                 1519
```

<210> SEQ ID NO 46
<211> LENGTH: 1189
<212> TYPE: DNA
<213> ORGANISM: Homo sapiens

<400> SEQUENCE: 46

```
ggcacgagat ttaatacaaa gtttgctttg agacttttca gcatatgatc tttttttccat    60 aaacttgtac agtgcaaaag acattttgaa taccatgatc gatgatgtcc catgcttcga   120
ggaaaaccaa acactttccg cctctcttgc aaaatccatt cctcatgctg accctcctca   180
cgatggctgt gtcagcccag ccccttccct tctccaggcc cagataactc ttccacaaac   240
aagatgagag ccactcggga aaagagccat agtcaactgg gagggcctac atctggatgg   300
cggtggaaaa acttgagggt ttggggttca aagtcagccc atcccacctg gcaaaatcct   360
cctggaagga ggaccttcaa gagcgcatca cctgaatgtc atgaagaagt atctctgaat   420
gtatccagga gaggaactgc ataaccaaag gggtgaccag ccctcagatg tgcttattgg   480
attccagtac aaacgccacc aaagccagcc cactgctctc ctacaaggaa ggaaagatct   540
gcacgtgtaa acatgggggc agccttggaa catggtgttt tttggagttt cctttctcac   600
agttttccat ctccccactt ctttgatcag tcatgtgtcc gtgacctcgt tccatgacat   660
caggatagct gtgtttgcac accatgctgc atgttcattt ggagccagga ggggttctca   720
gtggagcctg gcttagggaa cagggagcga tggaagaatg ccaacattag cgttggtctt   780
ctcttgtcag gaatgaagga tgcttgcaca catgcaccccc ctcactctca cacttgcaca   840
catacacaca cacacacacg aaatggttgg tttgtcaaaa ctcactgtag tacataaagc   900
ttgcactctg cgtcctatat ctagcagcat ggggtacgtt tggcagttca ctccattagg   960
gggtaaataa tttatgacca ttcatctgtt tttatgaatt tttttatcta gacaataatt  1020
gtaaataaag aactccaccat ctctgttcat ttaatactat gcaatggtta tgctttcaat  1080
cgctggctct tctgactcgt gcagtgtggt tctgaaatgt ttgtggttta aaaaaaaag   1140 caaaaaacac tcaacagaac atagtaaata taaaaaaaaa aaaaaaaa               1189
```

<210> SEQ ID NO 47
<211> LENGTH: 2584
<212> TYPE: DNA
<213> ORGANISM: Homo sapiens
<220> FEATURE:
<221> NAME/KEY: SITE
<222> LOCATION: (1389)
<223> OTHER INFORMATION: n equals a,t,g, or c

<400> SEQUENCE: 47

```
acccacgcgt ccgcgggcac cggccgacat ggcggcagcg gtggcggctg cgctggcgcg    60
gcttttggcg gcctttctgc tcctcgcggc ccaggtggcc tgtgagtacg catggtgca   120 cgtggtctcc caggccgggg gccccgaagg caaagactac tgcatcctct acaacccgca   180
gtgggcccat cttccgcacg acctcagcaa ggcatctttc ctgcagctgc gcaactggac   240
ggcctccctg ctctgctccg cagccgacct ccccgcccgt ggcttcagca accagatccc   300
gctggtggcg cgggggaact gcaccttcta tgagaaagtg aggctggccc agggcagcgg   360
```

```
acacgcgggc tgctcatcgt cagcagggag argctggtcc ccccgggggg taataagacg      420
catatgatga gattggcatt cccgtggccc tgctcagcta caaagacatg ctggacatct      480
tcacgcgttt cggccgcacg gtgagggcgg cgctgtatgc gcctaaggag ccggtgctgg      540
actacaacat ggtcatcatc ttcatcatgg ctgtgggsac cgtcgccatc ggcggctact      600
gggccgggak tcgggacgtg aagaaaaggt acatgaagca caagcgcgac gatgggcccg      660
agaagcagga ggacgaggcg gtggacgtga cgccggtgat gacctgcgtg tttgtggtga      720
tgtgctgctc catgctggtg ctgctctact ayttctacga cctcctcgtg trcgtggtca      780
tcgggatctt ctgcctggcc tccgccaccg gcctctacag ctgcctggcg ccctgtgtgc      840
ggcggctgcc cttcggcaag tgcaggatcc ccaacaacag cctgccctac ttccacaagc      900
gcccgcaggc ccgtatgctg ctcctggcgc tcttctgcgt ggscgtcagc gtggtgtggg      960
gcgtcttccg caacgargac cagtgggcct gggtcctcca ggatgccctg ggcatcgcct     1020
tctgcctcta catgctgaag accatccgtc tgcccacctt caaggcctgc acgctgctgc     1080
tgctggtgct gttcctctac gacatcttct tcgtgttcat cacgcccttc ctgaccaaga     1140
gtgggagcag catcatggtg gaggtggcca ctgggccctc ggactcagcc acccgtgaga     1200
agctgcccat ggtcctgaag gtgcccaggc tgaactcctc acctctggcc ctgtgtgacc     1260
ggccctttct cctcctgggt tcggagaca ttttggtgcc agggctgctg gtggcctact     1320
gccacaggtt tgacatccag gtacagtcct ccagggtata cttcgtggcc tgcaccatcg     1380
cctatggynt tggcctcctt gtgacattcg tggcactggc cctgatgcag cgtggccagc     1440
ccgctctcct ctacctggtg ccctgcacgc tggtgacgag ctgcgctgtg gcgctctggc     1500
gcygkgagct gggcgtgttc tggacgggca gcggctttgc gaaagtccta cctccatctc     1560
cgtgggcccc agcaccagcc gacggccgcg agcctcccaa agactctgcc acgccactct     1620
ccccgcagcc gcccagcgaa gaaccagcca catcccctg gcctgctgag cagtccccaa     1680
aatcacgcac gtccgaggag atgggggctg gagccatgct gggasgcctgg gagcccagct     1740 gaatccgagg gccgggacca ggccagccgt ccccggtaac ccagcctggc gcctcggcct     1800
aggggagggg tgagacgctc gctgccgtgc ccgccacacc aagatgttgg ggctgcctgg     1860
cgcccactgg agacagacag acagacgcyt gtcccccggg accgaggcct gtgccgtccc     1920
cacccgcccc aacatggtgc ttatccttgc cgagacccct gcagtccgtg cccgcgccca     1980
gcccagctgc cccggctgca cgcctgctgc tcccagctcg cccggctgcc acaagctctc     2040
tgcgggtcca tcctccccgc aggaggaggg gtccgtcctc gcaggccytg cccggcctct     2100
ctgcagaccc tcaagcgtcg tctgcatgag tgagcaggcg tgggtggact ctggccgcgg     2160
ccacacttgg tgctcaccag ctgcttcggc cttcaggtga cctccctccc cacggcatcc     2220
tgctctccgg gtgaagagc agctttctgt ctcccagaag gcatcgcttt ccctcttga     2280 gcagatcgga gcccctggga ggtttggaag ctgcctccaa gcctaggaca cggaccggtg     2340
gccggggcgc cctctggccc ctgacgctgg ctgagacagg cccgtggggc ggggttttgg     2400
ggcgtgaaca aggctggcag taagtggaca agctgctccc ctggctaagg ccctgccctg     2460
ccctcagcca gaggtgcctg gccatgcctg cacactcctc cccattttaa taatggtcg      2520 caacttcaaa aaaaaaaaaa aaaaaaaaaa aaaaaaaaaa aaaaaaaaaa aaaagggcgg     2580
ccgc                                                                  2584
```

<210> SEQ ID NO 48

<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 48

Met Ile Lys His Ala Leu Ile Arg Pro Phe Ile Val Phe Ser Leu Leu
1               5                   10                  15

Leu Arg Leu Cys Ser Glu Asn Leu Phe Cys Pro Asn Thr Gln Phe Ile
            20                  25                  30

Val Leu Ser Cys Phe Gln Ser Val Val Lys Ser Leu Leu Ser Ile Leu
        35                  40                  45

Asn Leu Ser Tyr Cys Ile Phe Xaa
    50                  55

<210> SEQ ID NO 49
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 49

Met Asn Ser Cys Leu Phe Leu Cys Ile Leu Ile Leu Glu Ser Ala Met
1               5                   10                  15

Val Val Leu Met Lys Val His Phe Ile Val Ala Phe Glu Leu Thr Ala
            20                  25                  30

Lys Ala Ile Asn Gln Lys Gln Lys Xaa
        35                  40

<210> SEQ ID NO 50
<211> LENGTH: 94
<212> TYPE: PRT
<213> ORGANISM: Homo sapiens
<220> FEATURE:
<221> NAME/KEY: SITE
<222> LOCATION: (94)
<223> OTHER INFORMATION: Xaa equals stop translation

<400> SEQUENCE: 50

Met Ala Arg Lys Ser Phe Ala Leu Leu Met Phe Val Trp Gln Met Ser
1               5                   10                  15

Leu Ser Leu Pro Ile Lys Gly Phe Ile Leu Arg Val Ala Asn Trp Leu
            20                  25                  30

Phe Lys Pro His Leu Asn Ser Val Cys Leu Gly Trp Gln Asn His Thr
        35                  40                  45

Arg Phe Cys Trp Ala Asn Leu Pro Gly Val Leu Leu Glu Ser
    50                  55                  60

Ala Thr Ala Glu Asp Thr Leu Ser Trp Pro Leu Ala Leu Gln Thr Ile
65                  70                  75                  80

Val Glu Glu Gly Val Trp Gly His Gln Pro Leu Pro Gly Xaa
                85                  90

<210> SEQ ID NO 51
<211> LENGTH: 84
<212> TYPE: PRT
<213> ORGANISM: Homo sapiens
<220> FEATURE:

<221> NAME/KEY: SITE
<222> LOCATION: (84)
<223> OTHER INFORMATION: Xaa equals stop translation

<400> SEQUENCE: 51

Met Leu Ser Leu Phe Phe Cys Phe Trp Lys Pro Ser Phe Leu Val Ser
 1               5                  10                  15

Arg Leu Val Ile Trp Leu Gly Leu Val Cys Gly Gly Arg Ser Leu Ser
             20                  25                  30

Trp Val Ala Leu Gly Glu Asp Tyr Leu Gly Thr Pro Ile Leu Ile Pro
         35                  40                  45

Asn Ile His Gln Thr Cys Pro His Pro Pro Leu Trp Glu Leu Val Pro
     50                  55                  60

Glu His Pro Cys Arg Leu Val Leu Ile Phe Ser Leu Cys Glu His Thr
 65                  70                  75                  80

His Ile Arg Xaa

<210> SEQ ID NO 52
<211> LENGTH: 66
<212> TYPE: PRT
<213> ORGANISM: Homo sapiens
<220> FEATURE:
<221> NAME/KEY: SITE
<222> LOCATION: (66)
<223> OTHER INFORMATION: Xaa equals stop translation

<400> SEQUENCE: 52

Met Leu Ser Pro Lys Ser Pro Arg Met Leu Leu Pro Cys Leu Leu Gln
 1               5                  10                  15

Pro Leu Val Val Ala Asn Ile Pro Arg Val Pro Trp Leu Ala Asp Glu
             20                  25                  30

Ser Leu Asn Pro Thr Pro Ile Ile Thr Trp Gln Ser Pro Cys Val Ala
         35                  40                  45

Gln Leu Cys Pro Asn Phe Pro Phe Pro Thr Arg Thr Leu Val Thr Gly
     50                  55                  60

Leu Xaa
 65

<210> SEQ ID NO 53
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 53

Met His Cys His Ser Ala Leu Gly Pro Met Ser Thr Pro Val Leu Pro
 1               5                  10                  15

Phe Ser Gly Ile Gly Leu Ala Phe Leu Cys Leu Cys Leu Ala Ala Ser
             20                  25                  30

Met Val Asp Leu Lys Cys Leu Gly Met Asn Ser Thr Leu Leu Gln Pro
         35                  40                  45

Ser Ile Lys Glu Xaa
     50

<210> SEQ ID NO 54
<211> LENGTH: 541
<212> TYPE: PRT
<213> ORGANISM: Homo sapiens

```
<220> FEATURE:
<221> NAME/KEY: SITE
<222> LOCATION: (10)
<223> OTHER INFORMATION: Xaa equals any of the naturally occurring
      L-amino acids
<221> NAME/KEY: SITE
<222> LOCATION: (469)
<223> OTHER INFORMATION: Xaa equals any of the naturally occurring
      L-amino acids
<221> NAME/KEY: SITE
<222> LOCATION: (541)
<223> OTHER INFORMATION: Xaa equals stop translation

<400> SEQUENCE: 54

Met Ala Thr Ser Gly Ala Ala Ser Ala Xaa Leu Val Ile Gly Trp Cys
 1               5                  10                  15

Ile Phe Gly Leu Leu Leu Ala Ile Leu Ala Phe Cys Trp Ile Tyr
                20                  25                  30

Val Arg Lys Tyr Gln Ser Arg Arg Glu Ser Glu Val Val Ser Thr Ile
            35                  40                  45

Thr Ala Ile Phe Ser Leu Ala Ile Ala Leu Ile Thr Ser Ala Leu Leu
        50                  55                  60

Pro Val Asp Ile Phe Leu Val Ser Tyr Met Lys Asn Gln Asn Gly Thr
 65                  70                  75                  80

Phe Lys Asp Trp Ala Asn Ala Asn Val Ser Arg Gln Ile Glu Asp Thr
                85                  90                  95

Val Leu Tyr Gly Tyr Tyr Thr Leu Tyr Ser Val Ile Leu Phe Cys Val
            100                 105                 110

Phe Phe Trp Ile Pro Phe Val Tyr Phe Tyr Glu Glu Lys Asp Asp
        115                 120                 125

Asp Asp Thr Ser Lys Cys Thr Gln Ile Lys Thr Ala Leu Lys Tyr Thr
    130                 135                 140

Leu Gly Phe Val Val Ile Cys Ala Leu Leu Leu Val Gly Ala Phe
145                 150                 155                 160

Val Pro Leu Asn Val Pro Asn Asn Lys Asn Ser Thr Glu Trp Glu Lys
                165                 170                 175

Val Lys Ser Leu Phe Glu Glu Leu Gly Ser Ser His Gly Leu Ala Ala
            180                 185                 190

Leu Ser Phe Ser Ile Ser Ser Leu Thr Leu Ile Gly Met Leu Ala Ala
        195                 200                 205

Ile Thr Tyr Thr Ala Tyr Gly Met Ser Ala Leu Pro Leu Asn Leu Ile
    210                 215                 220

Lys Gly Thr Arg Ser Ala Ala Tyr Glu Arg Leu Glu Asn Thr Glu Asp
225                 230                 235                 240

Ile Glu Glu Val Glu Gln His Ile Gln Thr Ile Lys Ser Lys Ser Lys
                245                 250                 255

Asp Gly Arg Pro Leu Pro Ala Arg Asp Lys Arg Ala Leu Lys Gln Phe
            260                 265                 270

Glu Glu Arg Leu Arg Thr Leu Lys Lys Arg Glu Arg His Leu Glu Phe
        275                 280                 285

Ile Glu Asn Ser Trp Trp Thr Lys Phe Cys Gly Ala Leu Arg Pro Leu
    290                 295                 300

Lys Ile Val Trp Gly Ile Phe Ile Leu Val Ala Leu Leu Phe Val
305                 310                 315                 320

Ile Ser Leu Phe Leu Ser Asn Leu Asp Lys Ala Leu His Ser Ala Gly
                325                 330                 335

Ile Asp Ser Gly Phe Ile Ile Phe Gly Ala Asn Leu Ser Asn Pro Leu
```

-continued

```
                            340                 345                 350
Asn Met Leu Leu Pro Leu Leu Gln Thr Val Phe Pro Leu Asp Tyr Ile
            355                 360                 365
Leu Ile Thr Ile Ile Ile Met Tyr Phe Ile Phe Thr Ser Met Ala Gly
        370                 375                 380
Ile Arg Asn Ile Gly Ile Trp Phe Phe Trp Ile Arg Leu Tyr Lys Ile
385                 390                 395                 400
Arg Arg Gly Arg Thr Arg Pro Gln Ala Leu Leu Phe Leu Cys Met Ile
                405                 410                 415
Leu Leu Leu Ile Val Leu His Thr Ser Tyr Met Ile Tyr Ser Leu Ala
            420                 425                 430
Pro Gln Tyr Val Met Tyr Gly Ser Gln Asn Tyr Leu Ile Glu Thr Asn
        435                 440                 445
Ile Thr Ser Asp Asn His Lys Gly Asn Ser Thr Leu Ser Val Pro Lys
    450                 455                 460
Arg Cys Asp Ala Xaa Ala Pro Glu Asp Gln Cys Thr Val Thr Arg Thr
465                 470                 475                 480
Tyr Leu Phe Leu His Lys Phe Trp Phe Ser Ala Ala Tyr Tyr Phe
                485                 490                 495
Gly Asn Trp Ala Phe Leu Gly Val Phe Leu Ile Gly Leu Ile Val Ser
            500                 505                 510
Cys Cys Lys Gly Lys Lys Ser Val Ile Glu Gly Val Asp Glu Asp Ser
        515                 520                 525
Asp Ile Ser Asp Asp Glu Pro Ser Val Tyr Ser Ala Xaa
    530                 535                 540
```

<210> SEQ ID NO 55
<211> LENGTH: 178
<212> TYPE: PRT
<213> ORGANISM: Homo sapiens
<220> FEATURE:
<221> NAME/KEY: SITE
<222> LOCATION: (67)
<223> OTHER INFORMATION: Xaa equals any of the naturally occurring
      L-amino acids
<221> NAME/KEY: SITE
<222> LOCATION: (178)
<223> OTHER INFORMATION: Xaa equals stop translation

<400> SEQUENCE: 55

```
Met Phe Gln Val Arg Pro Gly Trp Gln Leu Leu Leu Val Met Phe Ser
  1               5                  10                  15
Ser Cys Ala Val Ser Asn Gln Leu Leu Val Trp Tyr Pro Ala Thr Ala
                 20                  25                  30
Leu Ala Asp Asn Lys Pro Val Ala Pro Asp Arg Arg Ile Ser Gly His
             35                  40                  45
Val Gly Ile Ile Phe Ser Met Ser Tyr Leu Glu Ser Lys Gly Leu Leu
         50                  55                  60
Ala Thr Xaa Ser Glu Asp Arg Ser Val Arg Ile Trp Lys Val Gly Asp
 65                  70                  75                  80
Leu Arg Val Pro Gly Gly Arg Val Gln Asn Ile Gly His Cys Phe Gly
                 85                  90                  95
His Ser Ala Arg Val Trp Gln Val Lys Leu Leu Glu Asn Tyr Leu Ile
                100                 105                 110
Ser Ala Gly Glu Asp Cys Val Cys Leu Val Trp Ser His Glu Gly Glu
            115                 120                 125
Ile Leu Gln Ala Phe Arg Gly His Gln Asp Val Tyr Pro Val Val Val
```

-continued

```
               130                 135                 140
Gly Ala Glu Ile His Ala Glu Leu Tyr Gln Glu Leu Ala Tyr Leu Glu
145                 150                 155                 160

Thr Glu Thr Glu Ser Leu Ala His Leu Phe Ala Leu Val Pro Arg Pro
                165                 170                 175

Glu Xaa

<210> SEQ ID NO 56
<211> LENGTH: 84
<212> TYPE: PRT
<213> ORGANISM: Homo sapiens
<220> FEATURE:
<221> NAME/KEY: SITE
<222> LOCATION: (36)
<223> OTHER INFORMATION: Xaa equals any of the naturally occurring
      L-amino acids
<221> NAME/KEY: SITE
<222> LOCATION: (84)
<223> OTHER INFORMATION: Xaa equals stop translation

<400> SEQUENCE: 56

Met Ser Leu Ile Trp Glu Gln Gly Leu Gln Leu Cys Gly Phe Cys Leu
  1               5                  10                  15

Phe Tyr Leu Val Phe Cys Phe Cys Ile Ser Ser Leu Arg Val Met Ala
                 20                  25                  30

Phe Ser Cys Xaa His Val Ala Cys Cys Lys Gly Tyr Asp Phe Val Leu
             35                  40                  45

Phe Tyr Gly Cys Val Val Phe His Gly Val Tyr Gly Pro His Phe Leu
         50                  55                  60

Tyr Pro Ile His His Ile Trp Ala Pro Arg Leu Ile Pro Cys Leu Cys
 65                  70                  75                  80

Tyr Cys Glu Xaa

<210> SEQ ID NO 57
<211> LENGTH: 132
<212> TYPE: PRT
<213> ORGANISM: Homo sapiens
<220> FEATURE:
<221> NAME/KEY: SITE
<222> LOCATION: (132)
<223> OTHER INFORMATION: Xaa equals stop translation

<400> SEQUENCE: 57

Met Leu Trp Thr Leu Thr Phe Phe Leu Leu Gln Arg Ser Leu Thr Ser
  1               5                  10                  15

Pro Trp Leu Phe Gly Leu Leu Phe Leu Gly Ser Ser Asn Thr Ala Val
                 20                  25                  30

Cys Cys Phe Leu Gly Gln Leu Ile Met Gly Pro Lys Gly Glu Arg Gly
             35                  40                  45

Phe Pro Gly Pro Pro Gly Arg Cys Leu Cys Gly Pro Thr Met Asn Val
         50                  55                  60

Asn Asn Pro Ser Tyr Gly Glu Ser Val Tyr Gly Pro Ser Ser Pro Arg
 65                  70                  75                  80

Val Pro Val Val Arg Leu Ser Gly Arg Ser Leu Gly Trp Leu Ser Val
                 85                  90                  95

Arg Thr Ser His Leu Ile Leu Met Gly Leu Cys Lys Ile Leu Ser Val
                100                 105                 110

Lys Leu Thr Phe Phe His Asp Ser Glu Tyr Thr Leu Ile Ile Gly Asn
                115                 120                 125
```

```
Trp Lys Ile Xaa
    130
```

<210> SEQ ID NO 58
<211> LENGTH: 187
<212> TYPE: PRT
<213> ORGANISM: Homo sapiens
<220> FEATURE:
<221> NAME/KEY: SITE
<222> LOCATION: (167)
<223> OTHER INFORMATION: Xaa equals any of the naturally occurring
      L-amino acids

<400> SEQUENCE: 58

```
Met Gly Phe Phe Leu Val Leu Val Met Glu Gln Ile Thr Leu Ala Tyr
 1               5                  10                  15

Lys Glu Gln Ser Gly Pro Ser Pro Leu Glu Thr Arg Ala Leu Leu
                20                  25                  30

Gly Thr Val Asn Gly Gly Pro Gln His Trp His Asp Gly Pro Gly Val
                35                  40                  45

Pro Gln Ala Ser Gly Ala Pro Ala Thr Pro Ser Ala Leu Arg Ala Cys
        50                  55                  60

Val Leu Val Phe Ser Leu Ala Leu His Ser Val Phe Glu Gly Leu Ala
 65                  70                  75                  80

Val Gly Leu Gln Arg Asp Arg Ala Arg Ala Met Glu Leu Cys Leu Ala
                85                  90                  95

Leu Leu Leu His Lys Gly Ile Leu Ala Val Ser Leu Ser Leu Arg Leu
                100                 105                 110

Leu Gln Ser His Leu Arg Ala Gln Val Val Ala Gly Cys Gly Ile Leu
            115                 120                 125

Phe Ser Cys Met Thr Pro Leu Gly Ile Gly Leu Gly Ala Ala Leu Ala
        130                 135                 140

Glu Ser Ala Gly Pro Leu His Gln Leu Ala Gln Ser Val Leu Glu Gly
145                 150                 155                 160

Met Ala Ala Gly Thr Phe Xaa Tyr Ile Thr Phe Leu Glu Ile Leu Leu
                165                 170                 175

Phe His Pro Lys Phe Lys Gly Val Ser Arg Arg
            180                 185
```

<210> SEQ ID NO 59
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 59

```
Met Thr Phe Ser Pro Leu Ser Ser Thr Phe Trp Trp Ser Ser Arg Phe
 1               5                  10                  15

His Cys Glu Met Leu Trp Phe Val Ser Leu Leu Val Thr Phe Thr Ala
                20                  25                  30

His Ser Val Glu Tyr Ser Gln Tyr Xaa
            35                  40
```

<210> SEQ ID NO 60
<211> LENGTH: 339
<212> TYPE: PRT
<213> ORGANISM: Homo sapiens
<220> FEATURE:

```
<221> NAME/KEY: SITE
<222> LOCATION: (339)
<223> OTHER INFORMATION: Xaa equals stop translation

<400> SEQUENCE: 60
```

| | | | | | | | | | | | | | | | |
|---|---|---|---|---|---|---|---|---|---|---|---|---|---|---|---|
| Met | Tyr | Gly | Tyr | Val | Asp | Thr | Leu | Leu | Thr | Met | Leu | Ala | Met | Leu | Leu |
| 1 | | | | 5 | | | | | 10 | | | | | 15 | |
| Lys | Val | Ala | Met | Asn | Arg | Ala | Gln | Val | Cys | Leu | Ile | Ser | Ser | Ser | Lys |
| | | | 20 | | | | | 25 | | | | | 30 | | |
| Ser | Gly | Glu | Arg | His | Leu | Tyr | Leu | Ile | Lys | Val | Ser | Arg | Asp | Lys | Ile |
| | | 35 | | | | | 40 | | | | | 45 | | | |
| Ser | Asp | Ser | Asn | Asp | Gln | Glu | Ser | Ala | Asn | Cys | Asp | Ala | Lys | Ala | Ile |
| | 50 | | | | | 55 | | | | | 60 | | | | |
| Phe | Ala | Val | Leu | Thr | Ser | Val | Leu | Thr | Lys | Asp | Asp | Trp | Trp | Asn | Leu |
| 65 | | | | | 70 | | | | | 75 | | | | | 80 |
| Leu | Leu | Lys | Ala | Ile | Tyr | Ser | Leu | Cys | Asp | Leu | Ser | Arg | Phe | Gln | Glu |
| | | | | 85 | | | | | 90 | | | | | 95 | |
| Ala | Glu | Leu | Leu | Val | Asp | Ser | Ser | Leu | Glu | Tyr | Tyr | Ser | Phe | Tyr | Asp |
| | | | 100 | | | | | 105 | | | | | 110 | | |
| Asp | Arg | Gln | Lys | Arg | Lys | Glu | Leu | Glu | Tyr | Phe | Gly | Leu | Ser | Ala | Ala |
| | | 115 | | | | | 120 | | | | | 125 | | | |
| Ile | Leu | Asp | Lys | Asn | Phe | Arg | Lys | Ala | Tyr | Asn | Tyr | Ile | Arg | Ile | Met |
| | 130 | | | | | 135 | | | | | 140 | | | | |
| Val | Met | Glu | Asn | Val | Asn | Lys | Pro | Gln | Leu | Trp | Asn | Ile | Phe | Asn | Gln |
| 145 | | | | | 150 | | | | | 155 | | | | | 160 |
| Val | Thr | Met | His | Ser | Gln | Asp | Val | Arg | His | His | Arg | Phe | Cys | Leu | Arg |
| | | | | 165 | | | | | 170 | | | | | 175 | |
| Leu | Met | Leu | Lys | Asn | Pro | Glu | Asn | His | Ala | Leu | Cys | Val | Leu | Asn | Gly |
| | | | | 180 | | | | | 185 | | | | | 190 | |
| His | Asn | Ala | Phe | Val | Ser | Gly | Ser | Phe | Lys | His | Ala | Leu | Gly | Gln | Tyr |
| | | | | 195 | | | | | 200 | | | | | 205 | |
| Val | Gln | Ala | Phe | Arg | Thr | His | Pro | Asp | Glu | Pro | Leu | Tyr | Ser | Phe | Cys |
| | | 210 | | | | | 215 | | | | | 220 | | | |
| Ile | Gly | Leu | Thr | Phe | Ile | His | Met | Ala | Ser | Gln | Lys | Tyr | Val | Leu | Arg |
| 225 | | | | | 230 | | | | | 235 | | | | | 240 |
| Arg | His | Ala | Leu | Ile | Val | Gln | Gly | Phe | Ser | Phe | Leu | Asn | Arg | Tyr | Leu |
| | | | | 245 | | | | | 250 | | | | | 255 | |
| Ser | Leu | Arg | Gly | Pro | Cys | Gln | Glu | Ser | Phe | Tyr | Asn | Leu | Gly | Arg | Gly |
| | | | | 260 | | | | | 265 | | | | | 270 | |
| Leu | His | Gln | Leu | Gly | Leu | Ile | His | Leu | Ala | Ile | His | Tyr | Tyr | Gln | Lys |
| | | | | 275 | | | | | 280 | | | | | 285 | |
| Ala | Leu | Glu | Leu | Pro | Pro | Leu | Val | Val | Glu | Gly | Ile | Glu | Leu | Asp | Gln |
| | | | | 290 | | | | | 295 | | | | | 300 | |
| Leu | Asp | Leu | Arg | Arg | Asp | Ile | Ala | Tyr | Asn | Leu | Ser | Leu | Ile | Tyr | Gln |
| 305 | | | | | 310 | | | | | 315 | | | | | 320 |
| Ser | Ser | Gly | Asn | Thr | Gly | Met | Ala | Gln | Thr | Leu | Leu | Tyr | Thr | Tyr | Cys |
| | | | | 325 | | | | | 330 | | | | | 335 | |
| Ser | Ile | Xaa | | | | | | | | | | | | | |

```
<210> SEQ ID NO 61
<211> LENGTH: 48
<212> TYPE: PRT
<213> ORGANISM: Homo sapiens
<220> FEATURE:
<221> NAME/KEY: SITE
<222> LOCATION: (48)
```

<223> OTHER INFORMATION: Xaa equals stop translation

<400> SEQUENCE: 61

```
Met Leu Thr Val Lys Ile Leu Lys Cys Phe Leu Gly Trp Ala Val Val
 1               5                  10                  15

Ala Gly Gly Leu Gly Arg Ser Gln Ala Arg Pro Ser Leu Leu Phe Asn
                20                  25                  30

Arg Leu Ser Pro Ser Val Pro Gln Met Arg Ile Gln Gln Pro Trp Xaa
            35                  40                  45
```

<210> SEQ ID NO 62
<211> LENGTH: 336
<212> TYPE: PRT
<213> ORGANISM: Homo sapiens

<400> SEQUENCE: 62

```
Met Ala Ala Val Ala Ala Ala Leu Ala Arg Leu Leu Ala Ala Ala Phe
 1               5                  10                  15

Leu Leu Leu Ala Ala Gln Val Ala Cys Glu Tyr Gly Met Val His Val
                20                  25                  30

Val Ser Gln Ala Gly Gly Pro Glu Gly Lys Asp Tyr Cys Ile Leu Tyr
            35                  40                  45

Asn Pro Gln Trp Ala His Leu Pro His Asp Leu Ser Lys Ala Ser Phe
 50                  55                  60

Leu Gln Leu Arg Asn Trp Thr Ala Ser Leu Leu Cys Ser Ala Ala Asp
 65                  70                  75                  80

Leu Pro Ala Arg Gly Phe Ser Asn Gln Ile Pro Leu Val Ala Arg Gly
                85                  90                  95

Asn Cys Thr Phe Tyr Glu Lys Val Arg Leu Ala Gln Gly Ser Gly Ala
            100                 105                 110

Arg Gly Leu Leu Ile Val Ser Arg Glu Arg Leu Val Pro Pro Gly Gly
            115                 120                 125

Asn Lys Thr Gln Tyr Asp Glu Ile Gly Ile Pro Val Ala Leu Leu Ser
130                 135                 140

Tyr Lys Asp Met Leu Asp Ile Phe Thr Arg Phe Gly Arg Thr Val Arg
145                 150                 155                 160

Ala Ala Leu Tyr Ala Pro Lys Glu Pro Val Leu Asp Tyr Asn Met Val
                165                 170                 175

Ile Ile Phe Ile Met Ala Val Gly Thr Val Ala Ile Gly Gly Tyr Trp
            180                 185                 190

Ala Gly Ser Arg Asp Val Lys Lys Arg Tyr Met Lys His Lys Arg Asp
            195                 200                 205

Asp Gly Pro Glu Lys Gln Glu Asp Glu Ala Val Asp Val Thr Pro Val
    210                 215                 220

Met Thr Cys Val Phe Val Val Met Cys Cys Ser Met Leu Val Leu Leu
225                 230                 235                 240

Tyr Tyr Phe Tyr Asp Leu Leu Val Cys Val Val Ile Gly Ile Phe Cys
                245                 250                 255

Leu Ala Ser Ala Thr Gly Leu Tyr Ser Cys Leu Ala Pro Cys Val Arg
            260                 265                 270

Arg Leu Pro Phe Gly Lys Cys Arg Ile Pro Asn Asn Ser Leu Pro Tyr
            275                 280                 285

Phe His Lys Arg Pro Gln Ala Arg Met Leu Leu Leu Ala Leu Phe Cys
    290                 295                 300

Val Ala Val Ser Val Val Trp Gly Val Phe Arg Asn Glu Asp Ser Gly
```

```
305                 310                 315                 320
Pro Gly Ser Ser Arg Met Pro Trp Ala Ser Pro Ser Ala Ser Thr Cys
                325                 330                 335

<210> SEQ ID NO 63
<211> LENGTH: 85
<212> TYPE: PRT
<213> ORGANISM: Homo sapiens
<220> FEATURE:
<221> NAME/KEY: SITE
<222> LOCATION: (85)
<223> OTHER INFORMATION: Xaa equals stop translation

<400> SEQUENCE: 63

Met Lys Gly Trp Gly Trp Leu Ala Leu Leu Gly Ala Leu Leu Gly
  1               5                  10                  15

Thr Ala Trp Ala Arg Arg Ser Gln Asp Leu His Cys Gly Ala Cys Arg
                 20                  25                  30

Ala Leu Val Asp Glu Leu Glu Trp Glu Ile Ala Gln Val Asp Pro Lys
             35                  40                  45

Lys Thr Ile Gln Met Gly Ser Phe Arg Ile Asn Pro Asp Gly Ser Gln
         50                  55                  60

Ser Val Val Glu Val Thr Val Thr Val Pro Pro Asn Lys Val Ala His
 65                  70                  75                  80

Ser Gly Phe Gly Xaa
                 85

<210> SEQ ID NO 64
<211> LENGTH: 63
<212> TYPE: PRT
<213> ORGANISM: Homo sapiens
<220> FEATURE:
<221> NAME/KEY: SITE
<222> LOCATION: (63)
<223> OTHER INFORMATION: Xaa equals stop translation

<400> SEQUENCE: 64

Met Val Ala Val Thr Gly Gly Val Gly Val Ala Ala Leu Cys Leu
  1               5                  10                  15

Cys Ser Leu Leu Leu Trp Pro Thr Arg Leu Arg Arg Ser Arg Gly Gly
                 20                  25                  30

Glu His Arg Thr Pro Ser Glu Gly Glu Gly Ile Ser Thr Ala Pro Pro
             35                  40                  45

Pro Cys Trp Asn Glu Thr Gln Pro Gln Gly Gly Ala Lys Leu Xaa
         50                  55                  60

<210> SEQ ID NO 65
<211> LENGTH: 50
<212> TYPE: PRT
<213> ORGANISM: Homo sapiens
<220> FEATURE:
<221> NAME/KEY: SITE
<222> LOCATION: (50)
<223> OTHER INFORMATION: Xaa equals stop translation

<400> SEQUENCE: 65

Met Arg Leu Cys Ser Phe Thr Lys Val Pro Met Asn Leu Phe Leu Asn
  1               5                  10                  15

Val Ile Leu Leu Lys Phe Tyr Asn Phe Leu Phe Ser Leu Ile Leu Gly
                 20                  25                  30

Lys Ser Cys Leu Ala Ser Leu Gly Leu Cys Lys Asn Asn Lys Cys Leu
             35                  40                  45
```

Ser Xaa
    50

<210> SEQ ID NO 66
<211> LENGTH: 402
<212> TYPE: PRT
<213> ORGANISM: Homo sapiens
<220> FEATURE:
<221> NAME/KEY: SITE
<222> LOCATION: (402)
<223> OTHER INFORMATION: Xaa equals stop translation

<400> SEQUENCE: 66

Met Val Ala Leu Arg Gly Ala Ser Ala Leu Leu Val Leu Phe Leu Ala
 1               5                  10                  15

Ala Phe Leu Pro Pro Gln Cys Thr Gln Asp Pro Ala Met Val His
            20                  25                  30

Tyr Ile Tyr Gln Arg Phe Arg Val Leu Glu Gln Gly Leu Glu Lys Cys
            35                  40                  45

Thr Gln Ala Thr Arg Ala Tyr Ile Gln Glu Phe Gln Glu Phe Ser Lys
    50                  55                  60

Asn Ile Ser Val Met Leu Gly Arg Cys Gln Thr Tyr Thr Ser Glu Tyr
 65                  70                  75                  80

Lys Ser Ala Val Gly Asn Leu Ala Leu Arg Val Glu Arg Ala Gln Arg
                85                  90                  95

Glu Ile Asp Tyr Ile Gln Tyr Leu Arg Glu Ala Asp Glu Cys Ile Glu
            100                 105                 110

Ser Glu Asp Lys Thr Leu Ala Glu Met Leu Leu Gln Glu Ala Glu Glu
        115                 120                 125

Glu Lys Lys Ile Arg Thr Leu Leu Asn Ala Ser Cys Asp Asn Met Leu
    130                 135                 140

Met Gly Ile Lys Ser Leu Lys Ile Val Lys Met Met Asp Thr His
145                 150                 155                 160

Gly Ser Trp Met Lys Asp Ala Val Tyr Asn Ser Pro Lys Val Tyr Leu
                165                 170                 175

Leu Ile Gly Ser Arg Asn Asn Thr Val Trp Glu Phe Ala Asn Ile Arg
            180                 185                 190

Ala Phe Met Glu Asp Asn Thr Lys Pro Ala Pro Arg Lys Gln Ile Leu
        195                 200                 205

Thr Leu Ser Trp Gln Gly Thr Gly Gln Val Ile Tyr Lys Gly Phe Leu
    210                 215                 220

Phe Phe His Asn Gln Ala Thr Ser Asn Glu Ile Ile Lys Tyr Asn Leu
225                 230                 235                 240

Gln Lys Arg Thr Val Glu Asp Arg Met Leu Leu Pro Gly Val Gly
                245                 250                 255

Arg Ala Leu Val Tyr Gln His Ser Pro Ser Thr Tyr Ile Asp Leu Ala
            260                 265                 270

Val Asp Glu His Gly Leu Trp Ala Ile His Ser Gly Pro Gly Thr His
        275                 280                 285

Ser His Leu Val Leu Thr Lys Ile Glu Pro Gly Thr Leu Gly Val Glu
    290                 295                 300

His Ser Trp Asp Thr Pro Cys Arg Ser Gln Asp Ala Glu Ala Ser Phe
305                 310                 315                 320

Leu Leu Cys Gly Val Leu Tyr Val Tyr Ser Thr Gly Gly Gln Gly
                325                 330                 335

-continued

```
Pro His Arg Ile Thr Cys Ile Tyr Asp Pro Leu Gly Thr Ile Ser Glu
            340                 345                 350

Glu Asp Leu Pro Asn Leu Phe Phe Pro Lys Arg Pro Arg Ser His Ser
        355                 360                 365

Met Ile His Tyr Asn Pro Arg Asp Lys Gln Leu Tyr Ala Trp Asn Glu
    370                 375                 380

Gly Asn Gln Ile Ile Tyr Lys Leu Gln Thr Lys Arg Lys Leu Thr Leu
385                 390                 395                 400

Lys Xaa

<210> SEQ ID NO 67
<211> LENGTH: 58
<212> TYPE: PRT
<213> ORGANISM: Homo sapiens
<220> FEATURE:
<221> NAME/KEY: SITE
<222> LOCATION: (58)
<223> OTHER INFORMATION: Xaa equals stop translation

<400> SEQUENCE: 67

Met Val Ser Leu Leu Ser Ser Tyr Leu Leu Leu Glu Leu Leu Ser
  1               5                  10                  15

Lys Arg Ser Leu Phe Leu Gln Trp Tyr Leu Phe Phe Gly Leu Gln Cys
             20                  25                  30

Cys Ser Ser Phe Leu Cys Arg Lys Asn Glu Ser Gln Cys Phe Thr Arg
         35                  40                  45

Leu Lys Glu Arg Ser Ala Gly Ser Val Xaa
     50                  55

<210> SEQ ID NO 68
<211> LENGTH: 73
<212> TYPE: PRT
<213> ORGANISM: Homo sapiens
<220> FEATURE:
<221> NAME/KEY: SITE
<222> LOCATION: (73)
<223> OTHER INFORMATION: Xaa equals stop translation

<400> SEQUENCE: 68

Met Leu Arg Pro Ala Leu Pro Trp Leu Tyr Leu Gly Leu Cys Ser Leu
  1               5                  10                  15

Leu Val Gly Glu Ala Glu Ala Pro Ser Pro Val Asp Pro Leu Glu Arg
             20                  25                  30

Ser Arg Pro Tyr Ala Val Leu Arg Gly Gln Asn Leu Val Leu Met Gly
         35                  40                  45

Thr Ile Phe Ser Ile Leu Leu Val Thr Val Ile Leu Met Ala Phe Cys
     50                  55                  60

Val Tyr Lys Pro Ile Arg Arg Xaa
 65                  70

<210> SEQ ID NO 69
<211> LENGTH: 51
<212> TYPE: PRT
<213> ORGANISM: Homo sapiens
<220> FEATURE:
<221> NAME/KEY: SITE
<222> LOCATION: (51)
<223> OTHER INFORMATION: Xaa equals stop translation

<400> SEQUENCE: 69

Met Leu Thr Tyr Leu Pro Arg Trp Cys Phe Leu Ser Leu Pro Pro Pro
  1               5                  10                  15
```

-continued

```
Cys Cys Gly Ala Ala Ser Cys Thr Met Met His Ile Gln Ile Ile Leu
            20                  25                  30

Asn Thr His Ile Leu Ile Glu Arg Phe Leu Gly Phe Leu Leu Asn Gln
        35                  40                  45

Val Tyr Xaa
    50

<210> SEQ ID NO 70
<211> LENGTH: 182
<212> TYPE: PRT
<213> ORGANISM: Homo sapiens
<220> FEATURE:
<221> NAME/KEY: SITE
<222> LOCATION: (182)
<223> OTHER INFORMATION: Xaa equals stop translation

<400> SEQUENCE: 70

Met Thr Ser Arg Arg Ser Ser Thr Leu Ser Met Thr Ser Ser Leu Leu
 1               5                  10                  15

Ser Leu Gly Cys Ala Leu Thr Ser Ala Phe Pro Ala Ser Thr Met Ser
            20                  25                  30

Trp Val Pro Leu Leu Gln Met Leu Asp Gln Ser Pro Arg Arg Val Met
        35                  40                  45

Arg Lys Ser Val Ser Gln Leu Cys Pro Leu Leu Arg Pro His Pro Pro
 50                  55                  60

Leu Ser Ser Lys His Pro Leu Val Leu Pro Leu Gln Leu Pro Pro Thr
 65                  70                  75                  80

Phe Leu His Leu Leu Pro Gly Pro Gly Cys Pro Gly Gln Thr Val Ala
                85                  90                  95

Tyr Trp Leu Leu Glu Phe Leu Ser Arg Ala Thr Leu Lys Leu Tyr Pro
            100                 105                 110

Gly Asp Arg Pro Leu Trp Leu Gln Pro Thr Arg Leu Asn Phe Lys Asp
        115                 120                 125

His Trp Thr Ile Phe Ser Val Ala Ser Ala Ala Leu Phe Cys Val His
    130                 135                 140

Arg Met Ala Thr Asp Arg His Ala Ser Phe Pro Thr His Trp Lys Ala
145                 150                 155                 160

His Arg Gln Gly Glu Arg Gly His Arg Arg Cys Gln His Cys Arg Tyr
                165                 170                 175

Ser Lys Asp Leu Lys Xaa
            180

<210> SEQ ID NO 71
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 71

Met His Met Gly Leu Thr Thr Cys Lys Cys His Trp Lys Met Ala Tyr
 1               5                  10                  15

Leu Arg Phe Leu Ile Leu Trp Ser Phe Pro Leu Ser Ser Ala Val Ser
            20                  25                  30

Gly Ala Lys Arg Val Thr Asp Leu Leu Asn Gly Lys His Trp Lys Pro
        35                  40                  45
```

Xaa

<210> SEQ ID NO 72
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 72

Met Val Gln Phe Glu Val Ile Phe Leu Leu Phe Gly Leu Cys Phe Ser
 1               5                  10                  15

Ser Ser Ser Ser Arg Leu Val Gly Ser Gln Val Glu Asn Phe Ser Pro
                20                  25                  30

Thr Pro Cys Ile Phe Gln Ala Phe Arg Cys Ser Ser Leu Ala Ile Ile
            35                  40                  45

Ser Met Ser Leu Ser Xaa
        50

<210> SEQ ID NO 73
<211> LENGTH: 75
<212> TYPE: PRT
<213> ORGANISM: Homo sapiens
<220> FEATURE:
<221> NAME/KEY: SITE
<222> LOCATION: (75)
<223> OTHER INFORMATION: Xaa equals stop translation

<400> SEQUENCE: 73

Met Ser Val Val Pro Val Met Ile Pro Phe Leu Leu Leu Phe Phe
 1               5                  10                  15

Phe Ser Leu Ser Ser Thr His His Pro His Leu Leu Tyr Phe Ser Ile
                20                  25                  30

Phe Ile Phe Ser Gly Ser Leu Leu Val Arg Ile Leu Ser Cys Arg Lys
            35                  40                  45

Glu Ser Ser His Gln Val Leu Leu Ser Arg Lys Cys Phe Ile Lys Gly
        50                  55                  60

His Arg Gln His Arg Gln Leu Thr Lys Val Xaa
65                  70                  75

<210> SEQ ID NO 74
<211> LENGTH: 65
<212> TYPE: PRT
<213> ORGANISM: Homo sapiens
<220> FEATURE:
<221> NAME/KEY: SITE
<222> LOCATION: (65)
<223> OTHER INFORMATION: Xaa equals stop translation

<400> SEQUENCE: 74

Met Pro Leu Phe Leu Phe Val Ala His Leu Ile Ser Leu Leu Leu Ala
 1               5                  10                  15

Phe Arg Arg Pro Pro Ala Ser Gln Ile Thr Pro Arg Ala Trp Thr Thr
                20                  25                  30

Glu Ile Ala Ser Cys Glu Ser Val Glu Met Val Lys Ala Leu Ser Ser
            35                  40                  45

Leu Arg Ser Arg Ala Gln Val Asn Ala Asp Phe Pro Gly His Leu Cys
        50                  55                  60

Xaa
65

<210> SEQ ID NO 75
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 75

Met Ser Ser Val Lys Cys Pro Tyr Met Trp Cys Phe Trp Ala Phe Pro
1               5                   10                  15

Leu Phe Gln Leu Ser Val Phe Ile Pro Val Ser Lys Ser His Ser Ile
            20                  25                  30

Asn Tyr Tyr Asn Phe Ile Val Ser Leu Asn Ile Xaa
        35                  40

<210> SEQ ID NO 76
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 76

Met Ile Leu Phe Met Cys Phe Leu Val Tyr Cys Leu Ser Ser Val Glu
1               5                   10                  15

Trp Lys Ser His Arg Tyr Phe Val Phe Phe Ser Pro Cys Pro Phe Leu
            20                  25                  30

Tyr Pro Gln Leu Leu Glu His Ser Leu Glu His Ser Lys Cys Ser Val
        35                  40                  45

Leu Phe Met Glu Xaa
    50

<210> SEQ ID NO 77
<211> LENGTH: 320
<212> TYPE: PRT
<213> ORGANISM: Homo sapiens
<220> FEATURE:
<221> NAME/KEY: SITE
<222> LOCATION: (320)
<223> OTHER INFORMATION: Xaa equals stop translation

<400> SEQUENCE: 77

Met Ser Trp Cys Cys Leu Trp Leu Cys Leu Ser Ser Val Gly Arg Thr
1               5                   10                  15

Gly Ser Ala Gly Pro Ser Leu Pro Phe Ser Glu Leu Cys Ser Leu Gly
            20                  25                  30

Leu Leu Arg Leu Arg Pro Val Phe Ser Pro Leu His Ser Gly Pro Gly
        35                  40                  45

Lys Pro Ala Gln Phe Leu Ala Gly Glu Ala Glu Val Asn Ala Phe
    50                  55                  60

Ala Leu Gly Phe Leu Ser Thr Ser Ser Gly Val Ser Gly Glu Asp Glu
65                  70                  75                  80

Val Glu Pro Leu His Asp Gly Val Glu Glu Ala Glu Lys Lys Met Glu
                85                  90                  95

Glu Glu Gly Val Ser Val Ser Gly Met Glu Ala Thr Gly Ala Gln Gly
            100                 105                 110

```
Pro Ser Arg Val Glu Ala Glu Gly His Thr Glu Val Thr Glu Ala
        115                 120                 125

Glu Gly Ser Gln Gly Thr Ala Glu Ala Asp Gly Pro Gly Ala Ser Ser
130                 135                 140

Gly Asp Glu Asp Ala Ser Gly Arg Ala Ala Ser Pro Glu Ser Ala Ser
145                 150                 155                 160

Ser Thr Pro Glu Ser Leu Gln Ala Arg Arg His His Gln Phe Leu Glu
                165                 170                 175

Pro Ala Pro Ala Pro Gly Ala Ala Val Leu Ser Ser Glu Pro Ala Glu
            180                 185                 190

Pro Leu Leu Val Arg His Pro Arg Pro Arg Thr Thr Gly Pro Arg
        195                 200                 205

Pro Arg Gln Asp Pro His Lys Ala Gly Leu Ser His Tyr Val Lys Leu
    210                 215                 220

Phe Ser Phe Tyr Ala Lys Met Pro Met Glu Arg Lys Ala Leu Glu Met
225                 230                 235                 240

Val Glu Lys Cys Leu Asp Lys Tyr Phe Gln His Leu Cys Asp Asp Leu
                245                 250                 255

Glu Val Phe Ala Ala His Ala Gly Arg Lys Thr Val Lys Pro Glu Asp
            260                 265                 270

Leu Glu Leu Leu Met Arg Arg Gln Gly Leu Val Thr Asp Gln Val Ser
        275                 280                 285

Leu His Val Leu Val Glu Arg His Leu Pro Leu Glu Tyr Arg Gln Leu
    290                 295                 300

Leu Ile Pro Cys Ala Tyr Ser Gly Asn Ser Val Phe Pro Ala Gln Xaa
305                 310                 315                 320

<210> SEQ ID NO 78
<211> LENGTH: 172
<212> TYPE: PRT
<213> ORGANISM: Homo sapiens
<220> FEATURE:
<221> NAME/KEY: SITE
<222> LOCATION: (172)
<223> OTHER INFORMATION: Xaa equals stop translation

<400> SEQUENCE: 78

Met Ser Leu Pro Ile Pro Trp Leu Ser Leu Pro Pro Cys Pro Ile Leu
1               5                   10                  15

Gly Gln Pro Ala Gly Leu Leu Leu Trp Leu Phe Arg Pro Phe Ser Gln
            20                  25                  30

Cys Cys Gln Cys Pro Trp Glu Gly Arg Ala Ser Leu Arg His Pro Asn
        35                  40                  45

Gly Pro Ser Gly Cys Arg Glu Ala Glu Ala Trp Pro Gln Arg Ser Leu
    50                  55                  60

Leu Arg Gln Gln Leu Gln Gln Ala His Pro Leu Pro Thr Leu Pro Thr
65                  70                  75                  80

Pro Glu Arg Leu Pro Glu Gln Met Leu Phe Pro Ser Ser Ser Lys
                85                  90                  95

Pro Phe Ser Leu Leu Ser Leu Thr Ile Trp Ala Arg Leu Val Gly Arg
            100                 105                 110

Leu Thr Asn Arg Ile Cys Pro Val Pro Pro Gly Ser Val Ala Ser Ser
        115                 120                 125

Met Ser Leu Gln Ala Gly Arg Cys Gly Asn Pro Val Val Leu Pro Gln
    130                 135                 140

Pro Met Pro Pro Gly Leu Leu Cys Met Asn Glu Cys Ser Leu Val Pro
```

```
                    145                 150                 155                 160
Gly Leu Gly Arg Gly Gln Val Asn Ser Arg Val Xaa
                165                 170

<210> SEQ ID NO 79
<211> LENGTH: 61
<212> TYPE: PRT
<213> ORGANISM: Homo sapiens
<220> FEATURE:
<221> NAME/KEY: SITE
<222> LOCATION: (61)
<223> OTHER INFORMATION: Xaa equals stop translation

<400> SEQUENCE: 79

Met Val Ser Arg Ser Thr Ser Leu Thr Leu Ile Val Phe Leu Phe His
  1               5                  10                  15

Arg Leu Ser Lys Ala Pro Gly Lys Met Val Glu Asn Ser Pro Ser Pro
                 20                  25                  30

Leu Pro Glu Arg Ala Ile Tyr Gly Phe Val Leu Phe Leu Ser Ser Gln
             35                  40                  45

Phe Gly Phe Lys Asn Leu Lys Gly Ser Arg Val Cys Xaa
 50                  55                  60

<210> SEQ ID NO 80
<211> LENGTH: 101
<212> TYPE: PRT
<213> ORGANISM: Homo sapiens
<220> FEATURE:
<221> NAME/KEY: SITE
<222> LOCATION: (20)
<223> OTHER INFORMATION: Xaa equals any of the naturally occurring
      L-amino acids
<221> NAME/KEY: SITE
<222> LOCATION: (37)
<223> OTHER INFORMATION: Xaa equals any of the naturally occurring
      L-amino acids
<221> NAME/KEY: SITE
<222> LOCATION: (101)
<223> OTHER INFORMATION: Xaa equals stop translation

<400> SEQUENCE: 80

Met Leu Pro Ser Ala Trp Gly Pro Leu Gln Val Ala Ser Phe Phe Leu
  1               5                  10                  15

Leu Ser Phe Xaa Phe Cys Phe Leu Ser Ser Pro His Leu Gly Arg
                 20                  25                  30

Gln Glu Thr His Xaa Val Val Leu Glu Asp Asp Glu Gly Ala Pro Cys
             35                  40                  45

Pro Ala Glu Asp Glu Leu Ala Leu Gln Asp Asn Gly Phe Leu Ser Lys
 50                  55                  60

Asn Glu Val Leu Arg Thr Arg Cys Leu Gly Ser Arg Ser Gly Ser Ala
 65                  70                  75                  80

Ser Ala Thr Pro Pro Thr Thr Ser Gly Thr Ala Arg Ala Ala Arg Pro
                 85                  90                  95

Pro Ser Gln Cys Xaa
            100

<210> SEQ ID NO 81
<211> LENGTH: 98
<212> TYPE: PRT
<213> ORGANISM: Homo sapiens
<220> FEATURE:
<221> NAME/KEY: SITE
<222> LOCATION: (98)
<223> OTHER INFORMATION: Xaa equals stop translation
```

-continued

```
<400> SEQUENCE: 81

Met Ala Leu Leu Ala Leu Ala Ser Ala Val Pro Ser Ala Leu Leu Ala
 1               5                  10                  15

Leu Ala Val Phe Arg Val Pro Ala Trp Ala Cys Leu Leu Cys Phe Thr
            20                  25                  30

Thr Tyr Ser Glu Arg Leu Arg Ile Cys Gln Met Phe Val Gly Met Arg
         35                  40                  45

Ser Pro Ser Leu Lys Ser Val Arg Arg Pro Ser Arg Pro Pro Ser Arg
     50                  55                  60

Ala Ser Leu Thr Pro Lys Ser Val Arg Pro Ser Thr Leu His Gln
 65                  70                  75                  80

Cys Pro Gly Glu Gly Ala Glu Gly Gly Gln Glu Arg Pro Arg Gly Ser
                 85                  90                  95

Gly Xaa

<210> SEQ ID NO 82
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 82

Met Trp Leu Asn Phe Ser Asp Val His Thr Tyr Leu Ser Ser Ile Ala
 1               5                  10                  15

Leu Leu Cys Phe Cys Leu Ser Gly Val Leu Cys Cys Ile Cys Asn Asn
            20                  25                  30

Ser Val Phe His Ile Gln Gln Tyr Ile Leu Ile Ile Thr Phe Pro
         35                  40                  45

Leu Val Val Ile Xaa
     50

<210> SEQ ID NO 83
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 83

Met Ser His Ala Ser Arg Lys Thr Lys His Phe Pro Pro Leu Leu Gln
 1               5                  10                  15

Asn Pro Phe Leu Met Leu Thr Leu Leu Thr Met Ala Val Ser Ala Gln
            20                  25                  30

Pro Leu Pro Phe Ser Arg Pro Arg Xaa
         35                  40

<210> SEQ ID NO 84
<211> LENGTH: 133
<212> TYPE: PRT
<213> ORGANISM: Homo sapiens
<220> FEATURE:
<221> NAME/KEY: SITE
<222> LOCATION: (122)
<223> OTHER INFORMATION: Xaa equals any of the naturally occurring
      L-amino acids
<221> NAME/KEY: SITE
```

```
<222> LOCATION: (133)
<223> OTHER INFORMATION: Xaa equals stop translation

<400> SEQUENCE: 84
```

Met Ala Ala Val Ala Ala Ala Leu Ala Arg Leu Leu Ala Ala Phe
 1               5                  10                  15

Leu Leu Leu Ala Ala Gln Val Ala Cys Glu Tyr Gly Met Val His Val
            20                  25                  30

Val Ser Gln Ala Gly Gly Pro Glu Gly Lys Asp Tyr Cys Ile Leu Tyr
        35                  40                  45

Asn Pro Gln Trp Ala His Leu Pro His Asp Leu Ser Lys Ala Ser Phe
    50                  55                  60

Leu Gln Leu Arg Asn Trp Thr Ala Ser Leu Leu Cys Ser Ala Ala Asp
65                  70                  75                  80

Leu Pro Ala Arg Gly Phe Ser Asn Gln Ile Pro Leu Val Ala Arg Gly
                85                  90                  95

Asn Cys Thr Phe Tyr Glu Lys Val Arg Leu Ala Gln Gly Ser Gly His
            100                 105                 110

Ala Gly Cys Ser Ser Ser Ala Gly Arg Xaa Trp Ser Pro Arg Gly Val
        115                 120                 125

Ile Arg Arg Ile Xaa
        130

```
<210> SEQ ID NO 85
<211> LENGTH: 11
<212> TYPE: PRT
<213> ORGANISM: Homo sapiens

<400> SEQUENCE: 85
```

His Ser Ser Leu Pro His Phe Ser Ser Arg Ile
 1               5                  10

```
<210> SEQ ID NO 86
<211> LENGTH: 22
<212> TYPE: PRT
<213> ORGANISM: Homo sapiens

<400> SEQUENCE: 86
```

Arg Asp Ser Asn Gly Arg Gly Asp Ser Ser Leu Leu Lys Phe Val Cys
 1               5                  10                  15

Pro Val Pro Leu Lys Lys
            20

```
<210> SEQ ID NO 87
<211> LENGTH: 12
<212> TYPE: PRT
<213> ORGANISM: Homo sapiens

<400> SEQUENCE: 87
```

Ile Pro Glu Tyr Thr Phe Arg Arg Arg Trp Phe His
 1               5                  10

```
<210> SEQ ID NO 88
<211> LENGTH: 17
<212> TYPE: PRT
<213> ORGANISM: Homo sapiens

<400> SEQUENCE: 88
```

Leu Cys Val Ser Met Lys Ile Glu Trp Gly Arg Glu Ser Cys Glu Lys
 1               5                  10                  15

Lys

<210> SEQ ID NO 89
<211> LENGTH: 25
<212> TYPE: PRT
<213> ORGANISM: Homo sapiens

<400> SEQUENCE: 89

Arg Leu Lys Thr Thr Arg Ala Tyr Ser Ser Gln Phe Trp Arg Pro Glu
 1               5                  10                  15

Val Gln Asn Gln Gly Val Arg Lys Val
            20                  25

<210> SEQ ID NO 90
<211> LENGTH: 165
<212> TYPE: PRT
<213> ORGANISM: Homo sapiens

<400> SEQUENCE: 90

Leu Thr Leu Cys Leu Pro Arg Ser Leu Tyr Ala Leu Pro Gln Cys Pro
 1               5                  10                  15

Gly Pro His Val His Pro Cys Pro Ala Leu Leu Trp Asp Arg Ala Gly
            20                  25                  30

Leu Pro Leu Pro Leu Pro Gly Cys Ile His Gly Arg Ser Gln Val Pro
        35                  40                  45

Trp His Glu Leu His Ser Pro Ala Ala Phe Asn Gln Gly Met Met Gly
     50                  55                  60

Met Cys Thr Tyr Pro Thr Pro Pro Leu Gly Arg Val Met Leu Arg Cys
 65                  70                  75                  80

Gly Phe Leu Thr Val Pro Arg Leu Ser Gln Glu Ala Trp Val Trp Val
                85                  90                  95

Pro Thr Val Gly Ala Gly Val Ile Ser Tyr Leu Arg Arg Pro Pro Phe
            100                 105                 110

Leu Pro Val Leu Cys Ala Pro Thr Pro Thr Leu Glu Leu Pro Arg Phe
        115                 120                 125

Ser Val Phe Val Lys Glu Leu Thr Leu Cys Cys Leu Pro Leu Ser Gln
    130                 135                 140

Cys Pro Cys His Ser Cys Glu Pro Ala Ala Gly Glu Val Gly Ala Asp
145                 150                 155                 160

Leu Cys Val Ala Gly
                165

<210> SEQ ID NO 91
<211> LENGTH: 41
<212> TYPE: PRT
<213> ORGANISM: Homo sapiens

<400> SEQUENCE: 91

Leu Thr Leu Cys Leu Pro Arg Ser Leu Tyr Ala Leu Pro Gln Cys Pro
 1               5                  10                  15

Gly Pro His Val His Pro Cys Pro Ala Leu Leu Trp Asp Arg Ala Gly
            20                  25                  30

Leu Pro Leu Pro Leu Pro Gly Cys Ile
        35                  40

<210> SEQ ID NO 92
<211> LENGTH: 38
<212> TYPE: PRT
<213> ORGANISM: Homo sapiens -continued

```
<400> SEQUENCE: 92

His Gly Arg Ser Gln Val Pro Trp His Glu Leu His Ser Pro Ala Ala
 1               5                  10                  15

Phe Asn Gln Gly Met Met Gly Met Cys Thr Tyr Pro Thr Pro Pro Leu
            20                  25                  30

Gly Arg Val Met Leu Arg
        35

<210> SEQ ID NO 93
<211> LENGTH: 41
<212> TYPE: PRT
<213> ORGANISM: Homo sapiens

<400> SEQUENCE: 93

Cys Gly Phe Leu Thr Val Pro Arg Leu Ser Gln Glu Ala Trp Val Trp
 1               5                  10                  15

Val Pro Thr Val Gly Ala Gly Val Ile Ser Tyr Leu Arg Arg Pro Pro
            20                  25                  30

Phe Leu Pro Val Leu Cys Ala Pro Thr
        35                  40

<210> SEQ ID NO 94
<211> LENGTH: 45
<212> TYPE: PRT
<213> ORGANISM: Homo sapiens

<400> SEQUENCE: 94

Pro Thr Leu Glu Leu Pro Arg Phe Ser Val Phe Val Lys Glu Leu Thr
 1               5                  10                  15

Leu Cys Cys Leu Pro Leu Ser Gln Cys Pro Cys His Ser Cys Glu Pro
            20                  25                  30

Ala Ala Gly Glu Val Gly Ala Asp Leu Cys Val Ala Gly
        35                  40                  45

<210> SEQ ID NO 95
<211> LENGTH: 38
<212> TYPE: PRT
<213> ORGANISM: Homo sapiens

<400> SEQUENCE: 95

Ile Arg His Glu Thr Phe Arg Val Arg Gly Cys Ser Ile Ser Arg Ala
 1               5                  10                  15

Leu Ser Pro Phe Pro Leu Pro Phe Pro His Pro Gly Arg Ser Gly Trp
            20                  25                  30

Ser Gly Pro Glu Ala Lys
        35

<210> SEQ ID NO 96
<211> LENGTH: 145
<212> TYPE: PRT
<213> ORGANISM: Homo sapiens

<400> SEQUENCE: 96

Pro Asp Ser Arg Pro Glu Ala Arg Gly Asp His Val Val Arg Pro Ser
 1               5                  10                  15

Arg Gly Leu Arg Val Thr Gly Ala Thr Arg Ser Ile Met Gly Pro Trp
            20                  25                  30

Gly Glu Pro Glu Leu Leu Val Trp Arg Pro Glu Ala Val Ala Ser Glu
        35                  40                  45
```

```
Pro Pro Val Pro Val Gly Leu Glu Val Lys Leu Gly Ala Leu Val Leu
    50                  55                  60

Leu Leu Val Leu Thr Leu Leu Cys Ser Leu Val Pro Ile Cys Val Leu
 65                  70                  75                  80

Arg Arg Pro Gly Ala Asn His Glu Gly Ser Ala Ser Arg Gln Lys Ala
                 85                  90                  95

Leu Ser Leu Val Ser Cys Phe Ala Gly Val Phe Leu Ala Thr Cys
                100                 105                 110

Leu Leu Asp Leu Pro Asp Tyr Leu Ala Ala Ile Asp Glu Ala Leu
            115                 120                 125

Ala Ala Leu His Val Thr Leu Gln Phe Pro Leu Gln Glu Phe Ile Leu
    130                 135                 140

Ala
145

<210> SEQ ID NO 97
<211> LENGTH: 35
<212> TYPE: PRT
<213> ORGANISM: Homo sapiens

<400> SEQUENCE: 97

Pro Asp Ser Arg Pro Glu Ala Arg Gly Asp His Val Val Arg Pro Ser
 1               5                  10                  15

Arg Gly Leu Arg Val Thr Gly Ala Thr Arg Ser Ile Met Gly Pro Trp
             20                  25                  30

Gly Glu Pro
         35

<210> SEQ ID NO 98
<211> LENGTH: 37
<212> TYPE: PRT
<213> ORGANISM: Homo sapiens

<400> SEQUENCE: 98

Glu Leu Leu Val Trp Arg Pro Glu Ala Val Ala Ser Glu Pro Pro Val
 1               5                  10                  15

Pro Val Gly Leu Glu Val Lys Leu Gly Ala Leu Val Leu Leu Leu Val
             20                  25                  30

Leu Thr Leu Leu Cys
         35

<210> SEQ ID NO 99
<211> LENGTH: 36
<212> TYPE: PRT
<213> ORGANISM: Homo sapiens

<400> SEQUENCE: 99

Ser Leu Val Pro Ile Cys Val Leu Arg Arg Pro Gly Ala Asn His Glu
 1               5                  10                  15

Gly Ser Ala Ser Arg Gln Lys Ala Leu Ser Leu Val Ser Cys Phe Ala
             20                  25                  30

Gly Gly Val Phe
         35

<210> SEQ ID NO 100
<211> LENGTH: 37
<212> TYPE: PRT
<213> ORGANISM: Homo sapiens
```

-continued

```
<400> SEQUENCE: 100

Leu Ala Thr Cys Leu Leu Asp Leu Leu Pro Asp Tyr Leu Ala Ala Ile
  1               5                  10                  15

Asp Glu Ala Leu Ala Ala Leu His Val Thr Leu Gln Phe Pro Leu Gln
             20                  25                  30

Glu Phe Ile Leu Ala
             35

<210> SEQ ID NO 101
<211> LENGTH: 28
<212> TYPE: PRT
<213> ORGANISM: Homo sapiens

<400> SEQUENCE: 101

Lys Tyr Ile Leu Ser Ser Pro Leu Leu Asp Ser Leu Ala Glu His Lys
  1               5                  10                  15

Asn Leu Val Trp Lys Ser Phe Leu Pro Arg Asn Phe
             20                  25

<210> SEQ ID NO 102
<211> LENGTH: 70
<212> TYPE: PRT
<213> ORGANISM: Homo sapiens
<220> FEATURE:
<221> NAME/KEY: SITE
<222> LOCATION: (53)
<223> OTHER INFORMATION: Xaa equals any of the naturally occurring
      L-amino acids

<400> SEQUENCE: 102

Tyr Gly Lys Val Val Asp Leu Ala Pro Leu His Leu Asp Ala Arg Ile
  1               5                  10                  15

Ser Leu Ser Thr Leu Gln Gln Gln Leu Gly Gln Pro Glu Lys Ala Leu
             20                  25                  30

Glu Ala Leu Glu Pro Met Tyr Asp Pro Asp Thr Leu Ala Gln Asp Ala
         35                  40                  45

Asn Ala Ala Gln Xaa Glu Leu Lys Leu Leu Leu His Arg Ser Thr Leu
     50                  55                  60

Leu Phe Ser Gln Gly Lys
 65                  70

<210> SEQ ID NO 103
<211> LENGTH: 96
<212> TYPE: PRT
<213> ORGANISM: Homo sapiens
<220> FEATURE:
<221> NAME/KEY: SITE
<222> LOCATION: (58)
<223> OTHER INFORMATION: Xaa equals any of the naturally occurring
      L-amino acids

<400> SEQUENCE: 103

Asp Phe Met Glu Thr Phe Pro Asp Phe Cys Leu Pro Leu Ala Pro His
  1               5                  10                  15

Tyr Leu Gly Lys Ala Ala Leu Trp Ala Met Cys Pro Gly Arg Ala Trp
             20                  25                  30

Ala Gly Cys Gly Pro Val Leu Arg Thr Ser His Leu Gly Pro His Ser
         35                  40                  45

Ala Leu Pro Ser Trp Cys Asn Ile Cys Xaa Gln Ala Ile Val Gly Ala
     50                  55                  60

Gly Arg Gln Arg Gly Leu Ser Glu Asp Pro Thr Cys Ala Ser His Trp
```

```
                65                  70                  75                  80
Asp Thr Lys Thr Gly Leu Val Pro Ser Cys Gly Ala Gly Lys Gly Ile
                    85                  90                  95
```

<210> SEQ ID NO 104
<211> LENGTH: 44
<212> TYPE: PRT
<213> ORGANISM: Homo sapiens

<400> SEQUENCE: 104

```
Asp Phe Met Glu Thr Phe Pro Asp Phe Cys Leu Pro Leu Ala Pro His
 1               5                  10                  15
Tyr Leu Gly Lys Ala Ala Leu Trp Ala Met Cys Pro Gly Arg Ala Trp
                20                  25                  30
Ala Gly Cys Gly Pro Val Leu Arg Thr Ser His Leu
            35                  40
```

<210> SEQ ID NO 105
<211> LENGTH: 52
<212> TYPE: PRT
<213> ORGANISM: Homo sapiens
<220> FEATURE:
<221> NAME/KEY: SITE
<222> LOCATION: (14)
<223> OTHER INFORMATION: Xaa equals any of the naturally occurring
      L-amino acids

<400> SEQUENCE: 105

```
Gly Pro His Ser Ala Leu Pro Ser Trp Cys Asn Ile Cys Xaa Gln Ala
 1               5                  10                  15
Ile Val Gly Ala Gly Arg Gln Arg Gly Leu Ser Glu Asp Pro Thr Cys
                20                  25                  30
Ala Ser His Trp Asp Thr Lys Thr Gly Leu Val Pro Ser Cys Gly Ala
            35                  40                  45
Gly Lys Gly Ile
        50
```

<210> SEQ ID NO 106
<211> LENGTH: 280
<212> TYPE: PRT
<213> ORGANISM: Homo sapiens

<400> SEQUENCE: 106

```
Arg Leu Pro Gln Arg Gly Gln Trp Ala Trp Val Leu Gln Asp Ala Leu
 1               5                  10                  15
Gly Ile Ala Phe Cys Leu Tyr Met Leu Lys Thr Ile Arg Leu Pro Thr
                20                  25                  30
Phe Lys Ala Cys Thr Leu Leu Leu Val Leu Phe Leu Tyr Asp Ile
            35                  40                  45
Phe Phe Val Phe Ile Thr Pro Phe Leu Thr Lys Ser Gly Ser Ser Ile
    50                  55                  60
Met Val Glu Val Ala Thr Gly Pro Ser Asp Ser Ala Thr Arg Glu Lys
65                  70                  75                  80
Leu Pro Met Val Leu Lys Val Pro Arg Leu Asn Ser Ser Pro Leu Ala
                85                  90                  95
Leu Cys Asp Arg Pro Phe Ser Leu Leu Gly Phe Gly Asp Ile Leu Val
            100                 105                 110
Pro Gly Leu Leu Val Ala Tyr Cys His Arg Phe Asp Ile Gln Val Gln
        115                 120                 125
```

```
Ser Ser Arg Val Tyr Phe Val Ala Cys Thr Ile Ala Tyr Gly Val Gly
    130                 135                 140

Leu Leu Val Thr Phe Val Ala Leu Ala Leu Met Gln Arg Gly Gln Pro
145                 150                 155                 160

Ala Leu Leu Tyr Leu Val Pro Cys Thr Leu Val Thr Ser Cys Ala Val
                165                 170                 175

Ala Leu Trp Arg Arg Glu Leu Gly Val Phe Trp Thr Gly Ser Gly Phe
            180                 185                 190

Ala Lys Val Leu Pro Pro Ser Pro Trp Ala Pro Ala Pro Ala Asp Gly
        195                 200                 205

Pro Gln Pro Pro Lys Asp Ser Ala Thr Pro Leu Ser Pro Gln Pro Pro
    210                 215                 220

Ser Glu Glu Pro Ala Thr Ser Pro Trp Pro Ala Glu Gln Ser Pro Lys
225                 230                 235                 240

Ser Arg Thr Ser Glu Glu Met Gly Ala Gly Ala Pro Met Arg Glu Pro
                245                 250                 255

Gly Ser Pro Ala Glu Ser Glu Gly Arg Asp Gln Ala Gln Pro Ser Pro
            260                 265                 270

Val Thr Gln Pro Gly Ala Ser Ala
    275                 280

<210> SEQ ID NO 107
<211> LENGTH: 43
<212> TYPE: PRT
<213> ORGANISM: Homo sapiens

<400> SEQUENCE: 107

Arg Leu Pro Gln Arg Gly Gln Trp Ala Trp Val Leu Gln Asp Ala Leu
1               5                   10                  15

Gly Ile Ala Phe Cys Leu Tyr Met Leu Lys Thr Ile Arg Leu Pro Thr
            20                  25                  30

Phe Lys Ala Cys Thr Leu Leu Leu Val Leu
        35                  40

<210> SEQ ID NO 108
<211> LENGTH: 44
<212> TYPE: PRT
<213> ORGANISM: Homo sapiens

<400> SEQUENCE: 108

Phe Leu Tyr Asp Ile Phe Val Phe Ile Thr Pro Phe Leu Thr Lys
1               5                   10                  15

Ser Gly Ser Ser Ile Met Val Glu Val Ala Thr Gly Pro Ser Asp Ser
            20                  25                  30

Ala Thr Arg Glu Lys Leu Pro Met Val Leu Lys Val
        35                  40

<210> SEQ ID NO 109
<211> LENGTH: 44
<212> TYPE: PRT
<213> ORGANISM: Homo sapiens

<400> SEQUENCE: 109

Pro Arg Leu Asn Ser Ser Pro Leu Ala Leu Cys Asp Arg Pro Phe Ser
1               5                   10                  15

Leu Leu Gly Phe Gly Asp Ile Leu Val Pro Gly Leu Leu Val Ala Tyr
            20                  25                  30

Cys His Arg Phe Asp Ile Gln Val Gln Ser Ser Arg
```

-continued

<210> SEQ ID NO 110
<211> LENGTH: 43
<212> TYPE: PRT
<213> ORGANISM: Homo sapiens

<400> SEQUENCE: 110

Val Tyr Phe Val Ala Cys Thr Ile Ala Tyr Gly Val Gly Leu Leu Val
1               5                   10                  15

Thr Phe Val Ala Leu Ala Leu Met Gln Arg Gly Gln Pro Ala Leu Leu
            20                  25                  30

Tyr Leu Val Pro Cys Thr Leu Val Thr Ser Cys
        35                  40

<210> SEQ ID NO 111
<211> LENGTH: 40
<212> TYPE: PRT
<213> ORGANISM: Homo sapiens

<400> SEQUENCE: 111

Ala Val Ala Leu Trp Arg Arg Glu Leu Gly Val Phe Trp Thr Gly Ser
1               5                   10                  15

Gly Phe Ala Lys Val Leu Pro Pro Ser Pro Trp Ala Pro Ala Pro Ala
            20                  25                  30

Asp Gly Pro Gln Pro Pro Lys Asp
        35                  40

<210> SEQ ID NO 112
<211> LENGTH: 41
<212> TYPE: PRT
<213> ORGANISM: Homo sapiens

<400> SEQUENCE: 112

Ser Ala Thr Pro Leu Ser Pro Gln Pro Pro Ser Glu Glu Pro Ala Thr
1               5                   10                  15

Ser Pro Trp Pro Ala Glu Gln Ser Pro Lys Ser Arg Thr Ser Glu Glu
            20                  25                  30

Met Gly Ala Gly Ala Pro Met Arg Glu
        35                  40

<210> SEQ ID NO 113
<211> LENGTH: 25
<212> TYPE: PRT
<213> ORGANISM: Homo sapiens

<400> SEQUENCE: 113

Pro Gly Ser Pro Ala Glu Ser Glu Gly Arg Asp Gln Ala Gln Pro Ser
1               5                   10                  15

Pro Val Thr Gln Pro Gly Ala Ser Ala
            20                  25

<210> SEQ ID NO 114
<211> LENGTH: 26
<212> TYPE: PRT
<213> ORGANISM: Homo sapiens

<400> SEQUENCE: 114

Glu Ser Ser Gly Leu Pro Ala Leu Gly Pro Arg Arg Arg Pro Trp Glu
1               5                   10                  15

Gln Arg Trp Ser Asp Pro Ile Thr Leu Lys
            20                  25

-continued

<210> SEQ ID NO 115
<211> LENGTH: 61
<212> TYPE: PRT
<213> ORGANISM: Homo sapiens

<400> SEQUENCE: 115

```
Leu Thr Leu Ala Leu Asp Glu Ile Arg Leu Lys Lys Asp Leu Gly
 1               5                  10                  15

Leu Ile Glu Met Lys Lys Thr Asp Ser Glu Lys Arg Phe Gly Ser Val
                20                  25                  30

Ser Phe Gly Arg Ser Cys Arg Leu Ile Pro His Ala Leu Ala Ser Trp
            35                  40                  45

Leu Gln Thr Leu Ile Leu Cys Phe Cys Cys Arg Ile Cys
        50                  55                  60
```

<210> SEQ ID NO 116
<211> LENGTH: 32
<212> TYPE: PRT
<213> ORGANISM: Homo sapiens
<220> FEATURE:
<221> NAME/KEY: SITE
<222> LOCATION: (27)
<223> OTHER INFORMATION: Xaa equals any of the naturally occurring
      L-amino acids

<400> SEQUENCE: 116

```
Gly Arg Pro Thr Arg Pro Val Met Ala Ile Gln Ser Leu His Pro Cys
 1               5                  10                  15

Pro Ser Glu Leu Cys Cys Arg Ala Cys Val Xaa Phe Tyr His Trp Ala
                20                  25                  30
```

<210> SEQ ID NO 117
<211> LENGTH: 29
<212> TYPE: PRT
<213> ORGANISM: Homo sapiens

<400> SEQUENCE: 117

```
Asn Ser Lys Asn Thr Arg Asn Glu Arg Ser Phe Leu Lys Leu Phe Arg
 1               5                  10                  15

Asn Ile His Asp Ile Pro Leu Thr Val Leu Glu Asn Lys
                20                  25
```

<210> SEQ ID NO 118
<211> LENGTH: 20
<212> TYPE: PRT
<213> ORGANISM: Homo sapiens

<400> SEQUENCE: 118

```
Pro Arg Val Arg Gly Glu Gly Asn Arg Cys Trp Thr Gln Gly Ala Leu
 1               5                  10                  15

Cys His Arg Met
            20
```

<210> SEQ ID NO 119
<211> LENGTH: 421
<212> TYPE: PRT
<213> ORGANISM: Homo sapiens

<400> SEQUENCE: 119

```
Pro Arg Val Arg Gly Glu Gly Asn Arg Cys Trp Thr Gln Gly Ala Leu
 1               5                  10                  15
```

```
Cys His Arg Met Met Val Ala Leu Arg Gly Ala Ser Ala Leu Leu Val
             20                  25                  30
Leu Phe Leu Ala Ala Phe Leu Pro Pro Gln Cys Thr Gln Asp Pro
         35                  40                  45
Ala Met Val His Tyr Ile Tyr Gln Arg Phe Arg Val Leu Glu Gln Gly
         50                  55                  60
Leu Glu Lys Cys Thr Gln Ala Thr Arg Ala Tyr Ile Gln Glu Phe Gln
 65                  70                  75                  80
Glu Phe Ser Lys Asn Ile Ser Val Met Leu Gly Arg Cys Gln Thr Tyr
                 85                  90                  95
Thr Ser Glu Tyr Lys Ser Ala Val Gly Asn Leu Ala Leu Arg Val Glu
                100                 105                 110
Arg Ala Gln Arg Glu Ile Asp Tyr Ile Gln Tyr Leu Arg Glu Ala Asp
             115                 120                 125
Glu Cys Ile Glu Ser Glu Asp Lys Thr Leu Ala Glu Met Leu Leu Gln
         130                 135                 140
Glu Ala Glu Glu Lys Lys Ile Arg Thr Leu Leu Asn Ala Ser Cys
145                 150                 155                 160
Asp Asn Met Leu Met Gly Ile Lys Ser Leu Lys Ile Val Lys Lys Met
                 165                 170                 175
Met Asp Thr His Gly Ser Trp Met Lys Asp Ala Val Tyr Asn Ser Pro
             180                 185                 190
Lys Val Tyr Leu Leu Ile Gly Ser Arg Asn Asn Thr Val Trp Glu Phe
         195                 200                 205
Ala Asn Ile Arg Ala Phe Met Glu Asp Asn Thr Lys Pro Ala Pro Arg
         210                 215                 220
Lys Gln Ile Leu Thr Leu Ser Trp Gln Gly Thr Gly Gln Val Ile Tyr
225                 230                 235                 240
Lys Gly Phe Leu Phe His Asn Gln Ala Thr Ser Asn Glu Ile Ile
                 245                 250                 255
Lys Tyr Asn Leu Gln Lys Arg Thr Val Glu Asp Arg Met Leu Leu Pro
             260                 265                 270
Gly Gly Val Gly Arg Ala Leu Val Tyr Gln His Ser Pro Ser Thr Tyr
         275                 280                 285
Ile Asp Leu Ala Val Asp Glu His Gly Leu Trp Ala Ile His Ser Gly
         290                 295                 300
Pro Gly Thr His Ser His Leu Val Leu Thr Lys Ile Glu Pro Gly Thr
305                 310                 315                 320
Leu Gly Val Glu His Ser Trp Asp Thr Pro Cys Arg Ser Gln Asp Ala
                 325                 330                 335
Glu Ala Ser Phe Leu Leu Cys Gly Val Leu Tyr Val Val Tyr Ser Thr
             340                 345                 350
Gly Gly Gln Gly Pro His Arg Ile Thr Cys Ile Tyr Asp Pro Leu Gly
         355                 360                 365
Thr Ile Ser Glu Glu Asp Leu Pro Asn Leu Phe Phe Pro Lys Arg Pro
         370                 375                 380
Arg Ser His Ser Met Ile His Tyr Asn Pro Arg Asp Lys Gln Leu Tyr
385                 390                 395                 400
Ala Trp Asn Glu Gly Asn Gln Ile Ile Tyr Lys Leu Gln Thr Lys Arg
                 405                 410                 415
Lys Leu Thr Leu Lys
             420
```

```
<210> SEQ ID NO 120
<211> LENGTH: 27
<212> TYPE: PRT
<213> ORGANISM: Homo sapiens

<400> SEQUENCE: 120

Phe Pro Cys Ile Cys Leu Ser Gly Leu Leu Asp Leu Leu Ile Trp Arg
 1               5                  10                  15

Pro Phe Ser Glu Glu Leu Thr Lys Thr Phe Gly
            20                  25

<210> SEQ ID NO 121
<211> LENGTH: 84
<212> TYPE: PRT
<213> ORGANISM: Homo sapiens

<400> SEQUENCE: 121

Phe Pro Cys Ile Cys Leu Ser Gly Leu Leu Asp Leu Leu Ile Trp Arg
 1               5                  10                  15

Pro Phe Ser Glu Glu Leu Thr Lys Thr Phe Gly Met Val Ser Leu Leu
            20                  25                  30

Ser Ser Tyr Leu Leu Leu Glu Leu Leu Ser Lys Arg Ser Leu Phe
        35                  40                  45

Leu Gln Trp Tyr Leu Phe Phe Gly Leu Gln Cys Cys Ser Ser Phe Leu
     50                  55                  60

Cys Arg Lys Asn Glu Ser Gln Cys Phe Thr Arg Leu Lys Glu Arg Ser
 65                  70                  75                  80

Ala Gly Ser Val

<210> SEQ ID NO 122
<211> LENGTH: 24
<212> TYPE: PRT
<213> ORGANISM: Homo sapiens
<220> FEATURE:
<221> NAME/KEY: SITE
<222> LOCATION: (8)
<223> OTHER INFORMATION: Xaa equals any of the naturally occurring
      L-amino acids
<221> NAME/KEY: SITE
<222> LOCATION: (24)
<223> OTHER INFORMATION: Xaa equals any of the naturally occurring
      L-amino acids

<400> SEQUENCE: 122

Lys Asp Thr Cys Thr Arg Met Xaa Ile Ala Ala Leu Phe Thr Ile Ala
 1               5                  10                  15

Lys Ile Trp Asn Gln Pro Lys Xaa
            20

<210> SEQ ID NO 123
<211> LENGTH: 45
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring
      L-amino acids
<221> NAME/KEY: SITE
<222> LOCATION: (26)
<223> OTHER INFORMATION: Xaa equals any of the naturally occurring
      L-amino acids

<400> SEQUENCE: 123
```

```
Arg His Met His Thr Tyr Val Tyr Cys Gly Thr Ile His Asn Ser Lys
 1               5                  10                  15

Asp Leu Glu Pro Thr Gln Met Xaa Asp Xaa Ile Lys Lys Met Trp His
                20                  25                  30

Leu Tyr Thr Thr Lys Tyr Tyr Ala Ala Ile Lys Lys Asp
                35                  40              45
```

<210> SEQ ID NO 124
<211> LENGTH: 14
<212> TYPE: PRT
<213> ORGANISM: Homo sapiens

<400> SEQUENCE: 124

```
Arg Lys Cys Gly Thr Tyr Ile Pro Arg Asn Thr Met Gln Pro
 1               5                  10
```

<210> SEQ ID NO 125
<211> LENGTH: 40
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids

<400> SEQUENCE: 125

```
Lys Arg Thr Glu Phe Met Ser Phe Xaa Gly Thr Trp Met Lys Leu Glu
 1               5                  10                  15

Ala Ile Ile Leu Ser Lys Leu Thr Gln Glu Lys Thr Lys His Leu
                20                  25                  30

Met Phe Ser Leu Ile Ser Gly Ser
                35              40
```

<210> SEQ ID NO 126
<211> LENGTH: 11
<212> TYPE: PRT
<213> ORGANISM: Homo sapiens

<400> SEQUENCE: 126

```
Pro Lys Ser Asp Thr Ser Pro Ala Ser Ser Arg
 1               5                  10
```

<210> SEQ ID NO 127
<211> LENGTH: 15
<212> TYPE: PRT
<213> ORGANISM: Homo sapiens

<400> SEQUENCE: 127

```
Pro Lys Ser Asp Thr Ser Pro Ala Ser Ser Arg Leu Cys Trp Asp
 1               5                  10                  15
```

<210> SEQ ID NO 128
<211> LENGTH: 270
<212> TYPE: PRT
<213> ORGANISM: Homo sapiens

<400> SEQUENCE: 128

```
Tyr Val Pro Ser Phe Leu Pro Lys Ala Thr Gly Ser Ile Pro Ser Arg
 1               5                  10                  15

Lys Gly Gly Val Gly Ser Glu Lys Pro Glu Val Pro Leu Gln Thr Tyr
                20                  25                  30

Lys Glu Ile Val His Cys Cys Glu Glu Gln Val Leu Thr Leu Ala Thr
```

```
                35                  40                  45
Glu Gln Thr Tyr Ala Val Glu Gly Glu Thr Pro Ile Asn Arg Leu Ser
        50                  55                  60
Leu Leu Leu Ser Gly Arg Val Arg Val Ser Gln Asp Gly Gln Phe Leu
65                  70                  75                  80
His Tyr Ile Phe Pro Tyr Gln Phe Met Asp Ser Pro Glu Trp Glu Ser
                85                  90                  95
Leu Gln Pro Ser Glu Glu Gly Val Phe Gln Val Thr Leu Thr Ala Glu
            100                 105                 110
Thr Ser Cys Ser Tyr Ile Ser Trp Pro Arg Lys Ser Leu His Leu Leu
        115                 120                 125
Leu Thr Lys Glu Arg Tyr Ile Ser Cys Leu Phe Ser Ala Leu Leu Gly
    130                 135                 140
Tyr Asp Ile Ser Glu Lys Leu Tyr Thr Leu Asn Asp Lys Leu Phe Ala
145                 150                 155                 160
Lys Phe Gly Leu Arg Phe Asp Ile Arg Leu Pro Ser Leu Tyr His Val
                165                 170                 175
Leu Gly Pro Thr Ala Ala Asp Ala Gly Pro Glu Ser Glu Lys Gly Asp
            180                 185                 190
Glu Glu Val Cys Glu Pro Ala Val Ser Pro Gln Ala Thr Pro Thr
        195                 200                 205
Ser Leu Gln Gln Thr Pro Pro Cys Ser Thr Pro Ala Thr Thr Asn
    210                 215                 220
Phe Pro Ala Pro Pro Thr Arg Ala Arg Leu Ser Arg Pro Asp Ser Gly
225                 230                 235                 240
Ile Leu Ala Ser Arg Ile Pro Leu Gln Ser Tyr Ser Gln Val Ile Ser
                245                 250                 255
Arg Gly Gln Ala Pro Leu Ala Pro Thr His Thr Pro Glu Leu
            260                 265                 270

<210> SEQ ID NO 129
<211> LENGTH: 21
<212> TYPE: PRT
<213> ORGANISM: Homo sapiens

<400> SEQUENCE: 129

Ala Thr Gly Ser Ile Pro Ser Arg Lys Gly Val Gly Ser Glu Lys
1               5                   10                  15

Pro Glu Val Pro Leu
            20

<210> SEQ ID NO 130
<211> LENGTH: 25
<212> TYPE: PRT
<213> ORGANISM: Homo sapiens

<400> SEQUENCE: 130

Ile Val His Cys Cys Glu Glu Gln Val Leu Thr Leu Ala Thr Glu Gln
1               5                   10                  15

Thr Tyr Ala Val Glu Gly Glu Thr Pro
            20                  25

<210> SEQ ID NO 131
<211> LENGTH: 23
<212> TYPE: PRT
<213> ORGANISM: Homo sapiens

<400> SEQUENCE: 131
```

Gln Asp Gly Gln Phe Leu His Tyr Ile Phe Pro Tyr Gln Phe Met Asp
1               5                   10                  15

Ser Pro Glu Trp Glu Ser Leu
            20

<210> SEQ ID NO 132
<211> LENGTH: 23
<212> TYPE: PRT
<213> ORGANISM: Homo sapiens

<400> SEQUENCE: 132

Thr Leu Thr Ala Glu Thr Ser Cys Ser Tyr Ile Ser Trp Pro Arg Lys
1               5                   10                  15

Ser Leu His Leu Leu Leu Thr
            20

<210> SEQ ID NO 133
<211> LENGTH: 25
<212> TYPE: PRT
<213> ORGANISM: Homo sapiens

<400> SEQUENCE: 133

Asp Ile Ser Glu Lys Leu Tyr Thr Leu Asn Asp Lys Leu Phe Ala Lys
1               5                   10                  15

Phe Gly Leu Arg Phe Asp Ile Arg Leu
            20                  25

<210> SEQ ID NO 134
<211> LENGTH: 26
<212> TYPE: PRT
<213> ORGANISM: Homo sapiens

<400> SEQUENCE: 134

Ser Leu Tyr His Val Leu Gly Pro Thr Ala Ala Asp Ala Gly Pro Glu
1               5                   10                  15

Ser Glu Lys Gly Asp Glu Glu Val Cys Glu
            20                  25

<210> SEQ ID NO 135
<211> LENGTH: 28
<212> TYPE: PRT
<213> ORGANISM: Homo sapiens

<400> SEQUENCE: 135

Thr Thr Asn Phe Pro Ala Pro Pro Thr Arg Ala Arg Leu Ser Arg Pro
1               5                   10                  15

Asp Ser Gly Ile Leu Ala Ser Arg Ile Pro Leu Gln
            20                  25

<210> SEQ ID NO 136
<211> LENGTH: 196
<212> TYPE: PRT
<213> ORGANISM: Homo sapiens

<400> SEQUENCE: 136

Pro Lys Ser Asp Thr Ser Pro Ala Ser Ser Arg Leu Cys Trp Asp Met
1               5                   10                  15

Thr Ser Arg Arg Ser Ser Thr Leu Ser Met Thr Ser Ser Leu Leu Ser
            20                  25                  30

Leu Gly Cys Ala Leu Thr Ser Ala Phe Pro Ala Ser Thr Met Ser Trp
        35                  40                  45

-continued

```
Val Pro Leu Leu Gln Met Leu Asp Gln Ser Pro Arg Arg Val Met Arg
     50                  55                  60

Lys Ser Val Ser Gln Leu Cys Pro Leu Arg Pro His Pro Pro Leu
 65                  70                  75                  80

Ser Ser Lys His Pro Leu Val Leu Pro Leu Gln Leu Pro Pro Thr Phe
                 85                  90                  95

Leu His Leu Leu Pro Gly Pro Gly Cys Pro Gly Gln Thr Val Ala Tyr
                100                 105                 110

Trp Leu Leu Glu Phe Leu Ser Arg Ala Thr Leu Lys Leu Tyr Pro Gly
            115                 120                 125

Asp Arg Pro Leu Trp Leu Gln Pro Thr Arg Leu Asn Phe Lys Asp His
            130                 135                 140

Trp Thr Ile Phe Ser Val Ala Ser Ala Ala Leu Phe Cys Val His Arg
145                 150                 155                 160

Met Ala Thr Asp Arg His Ala Ser Phe Pro Thr His Trp Lys Ala His
                165                 170                 175

Arg Gln Gly Glu Arg Gly His Arg Arg Cys Gln His Cys Arg Tyr Ser
            180                 185                 190

Lys Asp Leu Lys
        195

<210> SEQ ID NO 137
<211> LENGTH: 10
<212> TYPE: PRT
<213> ORGANISM: Homo sapiens

<400> SEQUENCE: 137

Tyr Phe Ser His Gly Ile Cys Ser His Ala
 1               5                  10

<210> SEQ ID NO 138
<211> LENGTH: 55
<212> TYPE: PRT
<213> ORGANISM: Homo sapiens

<400> SEQUENCE: 138

Asn Ser Glu Asp Ile Ser Gln Thr Arg Gln Glu Leu Gly Leu Cys Ile
 1               5                  10                  15

Ser Gln Arg Cys Leu Ser Asp Arg Lys Lys Ser Arg Arg Ser Gly Val
                20                  25                  30

Trp Val Arg Ala Cys Thr Met Gln Phe Met Lys His Val Phe Pro Arg
            35                  40                  45

Leu Ile Ser Pro Arg Arg Pro
        50                  55

<210> SEQ ID NO 139
<211> LENGTH: 55
<212> TYPE: PRT
<213> ORGANISM: Homo sapiens

<400> SEQUENCE: 139

Pro Thr Arg His Phe Cys Gly Thr Ser Cys Leu Thr Gly Thr Ala
 1               5                  10                  15

Val Arg Cys Arg Ala Pro Ala Pro Val Trp Ser Val Arg Cys Pro His
                20                  25                  30

Cys Phe Arg Ser Ser Asp Ala Trp Val Asp Pro Gly Ile Pro Asp Arg
            35                  40                  45
```

```
Tyr Leu Gln Ala Tyr Leu Leu
        50                  55

<210> SEQ ID NO 140
<211> LENGTH: 246
<212> TYPE: PRT
<213> ORGANISM: Homo sapiens
<220> FEATURE:
<221> NAME/KEY: SITE
<222> LOCATION: (8)
<223> OTHER INFORMATION: Xaa equals any of the naturally occurring
      L-amino acids

<400> SEQUENCE: 140

Gly Glu Ala Met Asp Ala Glu Xaa Ala Val Ala Pro Pro Gly Cys Ser
 1               5                  10                  15

His Leu Gly Ser Phe Lys Val Asp Asn Trp Lys Gln Asn Leu Arg Ala
            20                  25                  30

Ile Tyr Gln Cys Phe Val Trp Ser Gly Thr Ala Glu Ala Arg Lys Arg
        35                  40                  45

Lys Ala Lys Ser Cys Ile Cys His Val Cys Gly Val His Leu Asn Arg
    50                  55                  60

Leu His Ser Cys Leu Tyr Cys Val Phe Phe Gly Cys Phe Thr Lys Lys
65                  70                  75                  80

His Ile His Glu His Ala Lys Ala Lys Arg His Asn Leu Ala Ile Asp
                85                  90                  95

Leu Met Tyr Gly Gly Ile Tyr Cys Phe Leu Cys Gln Asp Tyr Ile Tyr
            100                 105                 110

Asp Lys Asp Met Glu Ile Ile Ala Lys Glu Glu Gln Arg Lys Ala Trp
        115                 120                 125

Lys Met Gln Gly Val Gly Glu Lys Phe Ser Thr Trp Glu Pro Thr Lys
    130                 135                 140

Arg Glu Leu Glu Leu Leu Lys His Asn Pro Lys Arg Arg Lys Ile Thr
145                 150                 155                 160

Ser Asn Cys Thr Ile Gly Leu Arg Gly Leu Ile Asn Leu Gly Asn Thr
                165                 170                 175

Cys Phe Met Asn Cys Ile Val Gln Ala Leu Thr His Thr Pro Leu Leu
            180                 185                 190

Arg Asp Phe Phe Leu Ser Asp Arg His Arg Cys Glu Met Gln Ser Pro
        195                 200                 205

Ser Ser Cys Leu Val Cys Glu Met Ser Ser Leu Phe Gln Glu Phe Gly
    210                 215                 220

Arg Val Gly Arg Pro Gly Asn Ser Gly Pro Val Pro Ala Gly Val Pro
225                 230                 235                 240

Ser Ile Val Ser Pro Glu
                245

<210> SEQ ID NO 141
<211> LENGTH: 24
<212> TYPE: PRT
<213> ORGANISM: Homo sapiens

<400> SEQUENCE: 141

Val Ala Pro Pro Gly Cys Ser His Leu Gly Ser Phe Lys Val Asp Asn
 1               5                  10                  15

Trp Lys Gln Asn Leu Arg Ala Ile
            20
```

<210> SEQ ID NO 142
<211> LENGTH: 23
<212> TYPE: PRT
<213> ORGANISM: Homo sapiens

<400> SEQUENCE: 142

Thr Ala Glu Ala Arg Lys Arg Lys Ala Lys Ser Cys Ile Cys His Val
1               5                   10                  15

Cys Gly Val His Leu Asn Arg
            20

<210> SEQ ID NO 143
<211> LENGTH: 23
<212> TYPE: PRT
<213> ORGANISM: Homo sapiens

<400> SEQUENCE: 143

Phe Thr Lys Lys His Ile His Glu His Ala Lys Ala Lys Arg His Asn
1               5                   10                  15

Leu Ala Ile Asp Leu Met Tyr
            20

<210> SEQ ID NO 144
<211> LENGTH: 21
<212> TYPE: PRT
<213> ORGANISM: Homo sapiens

<400> SEQUENCE: 144

Tyr Asp Lys Asp Met Glu Ile Ile Ala Lys Glu Glu Gln Arg Lys Ala
1               5                   10                  15

Trp Lys Met Gln Gly
            20

<210> SEQ ID NO 145
<211> LENGTH: 28
<212> TYPE: PRT
<213> ORGANISM: Homo sapiens

<400> SEQUENCE: 145

Glu Leu Leu Lys His Asn Pro Lys Arg Arg Lys Ile Thr Ser Asn Cys
1               5                   10                  15

Thr Ile Gly Leu Arg Gly Leu Ile Asn Leu Gly Asn
            20                  25

<210> SEQ ID NO 146
<211> LENGTH: 26
<212> TYPE: PRT
<213> ORGANISM: Homo sapiens

<400> SEQUENCE: 146

Gly Asn Thr Cys Phe Met Asn Cys Ile Val Gln Ala Leu Thr His Thr
1               5                   10                  15

Pro Leu Leu Arg Asp Phe Phe Leu Ser Asp
            20                  25

<210> SEQ ID NO 147
<211> LENGTH: 20
<212> TYPE: PRT
<213> ORGANISM: Homo sapiens

<400> SEQUENCE: 147

Glu Phe Gly Arg Val Gly Arg Pro Gly Asn Ser Gly Pro Val Pro Ala
1               5                   10                  15

Gly Val Pro Ser
            20

<210> SEQ ID NO 148
<211> LENGTH: 108
<212> TYPE: PRT
<213> ORGANISM: Homo sapiens

<400> SEQUENCE: 148

Asn Ser Glu Asp Ile Ser Gln Thr Arg Gln Glu Leu Gly Leu Cys Ile
 1               5                  10                  15

Ser Gln Arg Cys Leu Ser Asp Arg Lys Lys Ser Arg Arg Ser Gly Val
            20                  25                  30

Trp Val Arg Ala Cys Thr Met Gln Phe Met Lys His Val Phe Pro Arg
        35                  40                  45

Leu Ile Ser Pro Arg Arg Pro Met Val Gln Phe Glu Val Ile Phe Leu
    50                  55                  60

Leu Phe Gly Leu Cys Phe Ser Ser Ser Ser Arg Leu Val Gly Ser
65                  70                  75                  80

Gln Val Glu Asn Phe Ser Pro Thr Pro Cys Ile Phe Gln Ala Phe Arg
                85                  90                  95

Cys Ser Ser Leu Ala Ile Ile Ser Met Ser Leu Ser
            100                 105

<210> SEQ ID NO 149
<211> LENGTH: 7
<212> TYPE: PRT
<213> ORGANISM: Homo sapiens

<400> SEQUENCE: 149

Ala Phe Pro Trp Pro Thr Ser
 1               5

<210> SEQ ID NO 150
<211> LENGTH: 23
<212> TYPE: PRT
<213> ORGANISM: Homo sapiens

<400> SEQUENCE: 150

Glu Ser Asn Phe Phe Tyr Pro Tyr Asp Ser Gln Leu Ala Leu Leu Ser
 1               5                  10                  15

Ser Val Thr Cys Ser Ala Ser
            20

<210> SEQ ID NO 151
<211> LENGTH: 83
<212> TYPE: PRT
<213> ORGANISM: Homo sapiens

<400> SEQUENCE: 151

Lys Leu Lys Met Phe Ala Phe Tyr Val Gln Val Leu Asn Gln Ser Lys
 1               5                  10                  15

Ser Ile Phe Val Tyr Ser Arg Asn Leu Ile Phe Ile His Met Ile
            20                  25                  30

Val Ser Trp Pro Ser Phe Leu Gln Leu Pro Ala Val His Gln Cys His
        35                  40                  45

Gln Ser Ser Val His Ile Cys Gly Val Ser Gly Leu Phe Pro Ser Ser
    50                  55                  60

Asn Tyr Gln Cys Leu Ser Leu Cys Gln Asn His Thr Val Leu Ile Ile

```
            65                  70                  75                  80
Thr Thr Leu

<210> SEQ ID NO 152
<211> LENGTH: 48
<212> TYPE: PRT
<213> ORGANISM: Homo sapiens

<400> SEQUENCE: 152

Ser Ile Leu Asn Val Ile Pro Asn Leu Ser Lys Gln Ser Phe Glu Glu
  1               5                  10                  15

Phe Asp Arg Leu Ile Leu Lys Tyr Met Gln Lys Ser Lys Ser Lys Arg
                 20                  25                  30

Ile Ala Lys Ile Leu Leu Ser Asn Lys Lys Thr Cys Pro Thr Lys Tyr
             35                  40                  45

<210> SEQ ID NO 153
<211> LENGTH: 36
<212> TYPE: PRT
<213> ORGANISM: Homo sapiens

<400> SEQUENCE: 153

Leu Pro Gln Ile Leu Arg Trp Leu Lys Tyr His Gln Ser Val Trp Gly
  1               5                  10                  15

Lys Gln Thr Pro Val Thr Leu His Tyr Leu Thr Leu Asp Leu Ile Gln
                 20                  25                  30

Glu Phe Thr Pro
             35

<210> SEQ ID NO 154
<211> LENGTH: 33
<212> TYPE: PRT
<213> ORGANISM: Homo sapiens

<400> SEQUENCE: 154

Ile Phe Val Tyr Ser Arg Asn Leu Ile Phe Phe Ile His Met Ile Val
  1               5                  10                  15

Ser Trp Pro Ser Phe Leu Gln Leu Pro Ala Val His Gln Cys His Gln
                 20                  25                  30

Ser

<210> SEQ ID NO 155
<211> LENGTH: 184
<212> TYPE: PRT
<213> ORGANISM: Homo sapiens

<400> SEQUENCE: 155

Pro Thr Gly Asn Asp Leu Val Tyr Val Phe Pro Cys Leu Leu Ser Val
  1               5                  10                  15

Phe Ser Arg Met Glu Glu Pro Ser Val Phe Cys Leu Phe Phe Pro Leu
                 20                  25                  30

Ser Ile Leu Ile Ser Ser Ala Ser Arg Thr Phe Pro Gly Thr Gln Gln
             35                  40                  45

Val Phe Ser Ile Val His Gly Val Thr Asp Val Ser Ala Lys Lys Val
         50                  55                  60

Gln Ser Gln Gly Arg Met Thr Ser Thr Gly Leu Asp Phe Asn Leu Leu
 65                  70                  75                  80

Pro Ala Trp Phe Pro Ser Pro Thr Ser Leu Gln Pro Thr Glu Asp Leu
                 85                  90                  95
```

Phe Gln Thr Gly Ser Leu Ser Arg Ser Phe Cys Ser Lys Ala Phe
              100                 105                 110

Ser Ser Ser Pro Leu Ser Pro Gly Gly Ser Pro Asn Ala Leu Thr Ser
        115                 120                 125

Val Lys Glu His Leu Val Ser Pro Ala Phe Leu Ala Ser His Ser Cys
130                 135                 140

Thr Ala Glu Ser Phe Pro Arg Val Asp Val Ile His Ala Val Pro Ile
145                 150                 155                 160

Ala Trp Ile Pro Ala Pro Leu His Pro Ile Gln Leu Ile Asn Ser Trp
                165                 170                 175

Phe Phe Phe Phe Phe Phe Phe Phe
            180

<210> SEQ ID NO 156
<211> LENGTH: 24
<212> TYPE: PRT
<213> ORGANISM: Homo sapiens

<400> SEQUENCE: 156

Asp Leu Val Tyr Val Phe Pro Cys Leu Leu Ser Val Phe Ser Arg Met
1               5                   10                  15

Glu Glu Pro Ser Val Phe Cys Leu
            20

<210> SEQ ID NO 157
<211> LENGTH: 24
<212> TYPE: PRT
<213> ORGANISM: Homo sapiens

<400> SEQUENCE: 157

Ile Ser Ser Ala Ser Arg Thr Phe Pro Gly Thr Gln Gln Val Phe Ser
1               5                   10                  15

Ile Val His Gly Val Thr Asp Val
            20

<210> SEQ ID NO 158
<211> LENGTH: 20
<212> TYPE: PRT
<213> ORGANISM: Homo sapiens

<400> SEQUENCE: 158

Phe Asn Leu Leu Pro Ala Trp Phe Pro Ser Pro Thr Ser Leu Gln Pro
1               5                   10                  15

Thr Glu Asp Leu
            20

<210> SEQ ID NO 159
<211> LENGTH: 25
<212> TYPE: PRT
<213> ORGANISM: Homo sapiens

<400> SEQUENCE: 159

Phe Cys Ser Lys Ala Phe Ser Ser Ser Pro Leu Ser Pro Gly Gly Ser
1               5                   10                  15

Pro Asn Ala Leu Thr Ser Val Lys Glu
            20                  25

<210> SEQ ID NO 160
<211> LENGTH: 23
<212> TYPE: PRT

<213> ORGANISM: Homo sapiens

<400> SEQUENCE: 160

Thr Ala Glu Ser Phe Pro Arg Val Asp Val Ile His Ala Val Pro Ile
 1               5                  10                  15

Ala Trp Ile Pro Ala Pro Leu
            20

<210> SEQ ID NO 161
<211> LENGTH: 34
<212> TYPE: PRT
<213> ORGANISM: Homo sapiens

<400> SEQUENCE: 161

Phe Ser Phe Leu Lys Pro Leu Cys Ala Pro Arg Ala Pro Trp Leu Trp
 1               5                  10                  15

Leu Pro Pro Ser Ser Lys Ser Arg Val His Val Gly Pro Gly Asp Phe
            20                  25                  30

Arg Ser

<210> SEQ ID NO 162
<211> LENGTH: 122
<212> TYPE: PRT
<213> ORGANISM: Homo sapiens
<220> FEATURE:
<221> NAME/KEY: SITE
<222> LOCATION: (108)
<223> OTHER INFORMATION: Xaa equals any of the naturally occurring
      L-amino acids

<400> SEQUENCE: 162

Val Cys Gly Thr Gly Gly Leu Glu Pro Asn Leu Ala Trp Val Arg Val
 1               5                  10                  15

Asp Asn Gly Ser Phe Pro Ser Ser Ser Pro Ser Val Pro Leu Glu His
            20                  25                  30

Pro Gly Cys Gly Cys Leu Leu His Pro Arg Ala Glu Ser Met Leu Gly
        35                  40                  45

Gln Glu Thr Ser Asp Pro Cys Pro Gly Ala Ala Ser Gly Phe Val Phe
    50                  55                  60

Pro Gln Trp Ala Gly Leu Gly Leu Leu Val His Leu Tyr Pro Ser Leu
65                  70                  75                  80

Ser Tyr Ala Ala Leu Ala Cys Cys Val Ser Gly Leu Tyr Ser Leu Pro
                85                  90                  95

Phe Thr Gln Ala Leu Gly Asn Gln Pro Ser Phe Xaa Gln Glu Arg Gln
            100                 105                 110

Arg Arg Ser Met Pro Leu Leu Trp Ala Ser
            115                 120

<210> SEQ ID NO 163
<211> LENGTH: 8
<212> TYPE: PRT
<213> ORGANISM: Homo sapiens

<400> SEQUENCE: 163

His Ala Gly Arg Lys Thr Val Lys
 1               5

<210> SEQ ID NO 164
<211> LENGTH: 61
<212> TYPE: PRT
<213> ORGANISM: Homo sapiens

```
<400> SEQUENCE: 164

Ser Phe Tyr Ala Lys Met Pro Met Glu Arg Lys Ala Leu Glu Met Val
  1               5                  10                  15

Glu Lys Cys Leu Asp Lys Tyr Phe Gln His Leu Cys Asp Asp Leu Glu
                 20                  25                  30

Val Phe Ala Ala His Ala Gly Arg Lys Thr Val Lys Pro Glu Asp Leu
             35                  40                  45

Glu Leu Leu Met Arg Arg Gln Gly Leu Val Thr Asp Gln
         50                  55                  60

<210> SEQ ID NO 165
<211> LENGTH: 19
<212> TYPE: PRT
<213> ORGANISM: Homo sapiens

<400> SEQUENCE: 165

Pro Met Glu Arg Lys Ala Leu Glu Met Val Glu Lys Cys Leu Asp Lys
  1               5                  10                  15

Tyr Phe Gln

<210> SEQ ID NO 166
<211> LENGTH: 22
<212> TYPE: PRT
<213> ORGANISM: Homo sapiens

<400> SEQUENCE: 166

Glu Val Phe Ala Ala His Ala Gly Arg Lys Thr Val Lys Pro Glu Asp
  1               5                  10                  15

Leu Glu Leu Leu Met Arg
                 20

<210> SEQ ID NO 167
<211> LENGTH: 31
<212> TYPE: PRT
<213> ORGANISM: Homo sapiens

<400> SEQUENCE: 167

Ser Phe Pro Ser Ser Pro Ser Val Pro Leu Glu His Pro Gly Cys
  1               5                  10                  15

Gly Cys Leu Leu His Pro Arg Ala Glu Ser Met Leu Gly Gln Glu
                 20                  25                  30

<210> SEQ ID NO 168
<211> LENGTH: 27
<212> TYPE: PRT
<213> ORGANISM: Homo sapiens

<400> SEQUENCE: 168

Tyr Pro Ser Leu Ser Tyr Ala Ala Leu Ala Cys Cys Val Ser Gly Leu
  1               5                  10                  15

Tyr Ser Leu Pro Phe Thr Gln Ala Leu Gly Asn
                 20                  25

<210> SEQ ID NO 169
<211> LENGTH: 353
<212> TYPE: PRT
<213> ORGANISM: Homo sapiens

<400> SEQUENCE: 169

Phe Ser Phe Leu Lys Pro Leu Cys Ala Pro Arg Ala Pro Trp Leu Trp
```

```
                1               5                   10                  15
        Leu Pro Pro Ser Ser Lys Ser Arg Val His Val Gly Pro Gly Asp Phe
                        20                  25                  30
        Arg Ser Met Ser Trp Cys Cys Leu Trp Leu Cys Leu Ser Ser Val Gly
                    35                  40                  45
        Arg Thr Gly Ser Ala Gly Pro Ser Leu Pro Phe Ser Glu Leu Cys Ser
                50                  55                  60
        Leu Gly Leu Leu Arg Leu Arg Pro Val Phe Ser Pro Leu His Ser Gly
        65                  70                  75                  80
        Pro Gly Lys Pro Ala Gln Phe Leu Ala Gly Glu Ala Glu Val Asn
                        85                  90                  95
        Ala Phe Ala Leu Gly Phe Leu Ser Thr Ser Ser Gly Val Ser Gly Glu
                        100                 105                 110
        Asp Glu Val Glu Pro Leu His Asp Gly Val Glu Glu Ala Glu Lys Lys
                        115                 120                 125
        Met Glu Glu Glu Gly Val Ser Val Ser Glu Met Glu Ala Thr Gly Ala
                    130                 135                 140
        Gln Gly Pro Ser Arg Val Glu Glu Ala Gly His Thr Glu Val Thr
        145                 150                 155                 160
        Glu Ala Glu Gly Ser Gln Gly Thr Ala Glu Ala Asp Gly Pro Gly Ala
                        165                 170                 175
        Ser Ser Gly Asp Glu Asp Ala Ser Gly Arg Ala Ala Ser Pro Glu Ser
                        180                 185                 190
        Ala Ser Ser Thr Pro Glu Ser Leu Gln Ala Arg Arg His His Gln Phe
                    195                 200                 205
        Leu Glu Pro Ala Pro Ala Pro Gly Ala Ala Val Leu Ser Ser Glu Pro
                    210                 215                 220
        Ala Glu Pro Leu Leu Val Arg His Pro Pro Arg Pro Arg Thr Thr Gly
        225                 230                 235                 240
        Pro Arg Pro Arg Gln Asp Pro His Lys Ala Gly Leu Ser His Tyr Val
                        245                 250                 255
        Lys Leu Phe Ser Phe Tyr Ala Lys Met Pro Met Glu Arg Lys Ala Leu
                        260                 265                 270
        Glu Met Val Glu Lys Cys Leu Asp Lys Tyr Phe Gln His Leu Cys Asp
                    275                 280                 285
        Asp Leu Glu Val Phe Ala Ala His Ala Gly Arg Lys Thr Val Lys Pro
                    290                 295                 300
        Glu Asp Leu Glu Leu Leu Met Arg Arg Gln Gly Leu Val Thr Asp Gln
        305                 310                 315                 320
        Val Ser Leu His Val Leu Val Glu Arg His Leu Pro Leu Glu Tyr Arg
                        325                 330                 335
        Gln Leu Leu Ile Pro Cys Ala Tyr Ser Gly Asn Ser Val Phe Pro Ala
                        340                 345                 350
        Gln

<210> SEQ ID NO 170
<211> LENGTH: 27
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids

<400> SEQUENCE: 170
```

Ala Pro Gly Gly Val Asn Ser Glu Gly Arg Gly Gln His Leu Pro Pro
 1               5                  10                  15

Pro Xaa Leu Ala Val Cys Leu Lys Leu His Leu
             20                  25

<210> SEQ ID NO 171
<211> LENGTH: 198
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids

<400> SEQUENCE: 171

Ala Pro Gly Gly Val Asn Ser Glu Gly Arg Gly Gln His Leu Pro Pro
 1               5                  10                  15

Pro Xaa Leu Ala Val Cys Leu Lys Leu His Leu Met Ser Leu Pro Ile
             20                  25                  30

Pro Trp Leu Ser Leu Pro Pro Cys Pro Ile Leu Gly Gln Pro Ala Gly
         35                  40                  45

Leu Leu Leu Trp Leu Phe Arg Pro Phe Ser Gln Cys Cys Gln Cys Pro
 50                  55                  60

Trp Glu Gly Arg Ala Ser Leu Arg His Pro Asn Gly Pro Ser Gly Cys
 65                  70                  75                  80

Arg Glu Ala Glu Ala Trp Pro Gln Arg Ser Leu Leu Arg Gln Gln Leu
                 85                  90                  95

Gln Gln Ala His Pro Leu Pro Thr Leu Pro Thr Pro Glu Arg Leu Pro
             100                 105                 110

Glu Gln Met Leu Phe Pro Ser Ser Ser Lys Pro Phe Ser Leu Leu
         115                 120                 125

Ser Leu Thr Ile Trp Ala Arg Leu Val Gly Arg Leu Thr Asn Arg Ile
     130                 135                 140

Cys Pro Val Pro Pro Gly Ser Val Ala Ser Ser Met Ser Leu Gln Ala
145                 150                 155                 160

Gly Arg Cys Gly Asn Pro Val Val Leu Pro Gln Pro Met Pro Pro Gly
                 165                 170                 175

Leu Leu Cys Met Asn Glu Cys Ser Leu Val Pro Gly Leu Gly Arg Gly
             180                 185                 190

Gln Val Asn Ser Arg Val
         195

<210> SEQ ID NO 172
<211> LENGTH: 44
<212> TYPE: PRT
<213> ORGANISM: Homo sapiens

<400> SEQUENCE: 172

Asn Ser Ala Glu Pro Ala Trp Val Pro Val Cys Ala Arg Gly Gly Gly
 1               5                  10                  15

Ala Gly Cys Gly Arg Arg Arg Gly Arg Arg Phe Cys Ala Ala Gly Ala
             20                  25                  30

Val Pro Ala Ala Glu Arg Gly Gly Glu Asn Gly Ser
         35                  40

<210> SEQ ID NO 173
<211> LENGTH: 124

```
<212> TYPE: PRT
<213> ORGANISM: Homo sapiens

<400> SEQUENCE: 173

Ser Leu Val Pro Ala Leu Lys Glu Val Val Leu Trp Arg Arg Gln
 1               5                  10                  15

Met Val Leu Tyr Leu Val Trp Ala Phe Ile Pro Glu Ser Trp Leu Asn
             20                  25                  30

Ser Leu Gly Leu Thr Tyr Trp Pro Gln Lys Tyr Trp Ala Val Ala Leu
         35                  40                  45

Pro Val Tyr Leu Leu Ile Ala Ile Val Ile Gly Tyr Val Leu Leu Phe
     50                  55                  60

Gly Ile Asn Met Met Ser Thr Ser Pro Leu Asp Ser Ile His Thr Ile
 65                  70                  75                  80

Thr Asp Asn Tyr Ala Lys Asn Gln Gln Gln Lys Lys Tyr Gln Glu Glu
                 85                  90                  95

Ala Ile Pro Ala Leu Arg Asp Ile Ser Ile Ser Glu Val Asn Gln Met
            100                 105                 110

Phe Phe Leu Ala Ala Lys Glu Leu Tyr Thr Lys Asn
            115                 120

<210> SEQ ID NO 174
<211> LENGTH: 28
<212> TYPE: PRT
<213> ORGANISM: Homo sapiens

<400> SEQUENCE: 174

Met Val Leu Tyr Leu Val Trp Ala Phe Ile Pro Glu Ser Trp Leu Asn
 1               5                  10                  15

Ser Leu Gly Leu Thr Tyr Trp Pro Gln Lys Tyr Trp
             20                  25

<210> SEQ ID NO 175
<211> LENGTH: 25
<212> TYPE: PRT
<213> ORGANISM: Homo sapiens

<400> SEQUENCE: 175

Tyr Trp Ala Val Ala Leu Pro Val Tyr Leu Leu Ile Ala Ile Val Ile
 1               5                  10                  15

Gly Tyr Val Leu Leu Phe Gly Ile Asn
             20                  25

<210> SEQ ID NO 176
<211> LENGTH: 22
<212> TYPE: PRT
<213> ORGANISM: Homo sapiens

<400> SEQUENCE: 176

Gln Gln Gln Lys Lys Tyr Gln Glu Glu Ala Ile Pro Ala Leu Arg Asp
 1               5                  10                  15

Ile Ser Ile Ser Glu Val
             20

<210> SEQ ID NO 177
<211> LENGTH: 104
<212> TYPE: PRT
<213> ORGANISM: Homo sapiens

<400> SEQUENCE: 177
```

```
Asn Ser Ala Glu Pro Ala Trp Val Pro Val Cys Ala Arg Gly Gly Gly
 1               5                  10                  15

Ala Gly Cys Gly Arg Arg Gly Arg Arg Phe Cys Ala Ala Gly Ala
            20                  25                  30

Val Pro Ala Ala Glu Arg Gly Gly Glu Asn Gly Ser Met Val Ser Arg
            35                  40                  45

Ser Thr Ser Leu Thr Leu Ile Val Phe Leu Phe His Arg Leu Ser Lys
         50                  55                  60

Ala Pro Gly Lys Met Val Glu Asn Ser Pro Ser Pro Leu Pro Glu Arg
 65                  70                  75                  80

Ala Ile Tyr Gly Phe Val Leu Phe Leu Ser Ser Gln Phe Gly Phe Lys
                 85                  90                  95

Asn Leu Lys Gly Ser Arg Val Cys
            100

<210> SEQ ID NO 178
<211> LENGTH: 32
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring
      L-amino acids

<400> SEQUENCE: 178

Leu Ser Pro Arg Leu Phe Asp Ala Gly Ile Leu Leu Trp Gly Ala Ser
 1               5                  10                  15

Val Asn Val Thr Ile Trp Glu Val Arg Xaa Ala Gln Ser Ser Ala Ser
            20                  25                  30

<210> SEQ ID NO 179
<211> LENGTH: 132
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring
      L-amino acids
<221> NAME/KEY: SITE
<222> LOCATION: (52)
<223> OTHER INFORMATION: Xaa equals any of the naturally occurring
      L-amino acids
<221> NAME/KEY: SITE
<222> LOCATION: (69)
<223> OTHER INFORMATION: Xaa equals any of the naturally occurring
      L-amino acids

<400> SEQUENCE: 179

Leu Ser Pro Arg Leu Phe Asp Ala Gly Ile Leu Leu Trp Gly Ala Ser
 1               5                  10                  15

Val Asn Val Thr Ile Trp Glu Val Arg Xaa Ala Gln Ser Ser Ala Ser
            20                  25                  30

Met Leu Pro Ser Ala Trp Gly Pro Leu Gln Val Ala Ser Phe Phe Leu
            35                  40                  45

Leu Ser Phe Xaa Phe Cys Phe Leu Ser Ser Ser Pro His Leu Gly Arg
         50                  55                  60

Gln Glu Thr His Xaa Val Val Leu Glu Asp Asp Gly Ala Pro Cys
 65                  70                  75                  80

Pro Ala Glu Asp Glu Leu Ala Leu Gln Asp Asn Gly Phe Leu Ser Lys
                 85                  90                  95
```

-continued

```
Asn Glu Val Leu Arg Thr Arg Cys Leu Gly Ser Arg Ser Gly Ser Ala
                100                 105                 110

Ser Ala Thr Pro Pro Thr Thr Ser Gly Thr Ala Arg Ala Ala Arg Pro
            115                 120                 125

Pro Ser Gln Cys
        130
```

<210> SEQ ID NO 181
<211> LENGTH: 32
<212> TYPE: PRT
<213> ORGANISM: Homo sapiens

<400> SEQUENCE: 180

```
Asn Leu Thr Ser Asp Pro Arg Pro Leu Ala Leu Pro Pro Pro Cys Gly
  1               5                   10                  15

Asp Phe Ile Lys Val Thr Ser Phe Ser Pro Gly Leu Glu Thr His Thr
                20                  25                  30
```

<210> SEQ ID NO 181
<211> LENGTH: 135
<212> TYPE: PRT
<213> ORGANISM: Homo sapiens
<220> FEATURE:
<221> NAME/KEY: SITE
<222> LOCATION: (14)
<223> OTHER INFORMATION: Xaa equals any of the naturally occurring
      L-amino acids

<400> SEQUENCE: 181

```
Glu Gln Gln Arg Leu Arg Asp Arg Glu Thr Gln Thr Gly Xaa Asp Ser
  1               5                   10                  15

Arg Ala Lys Thr Gln Arg Gly Glu Asp Gly Glu Ser Glu Arg Gly Arg
                20                  25                  30

Trp Arg Leu Arg Glu Gly Glu Asp Gly Asp Ser Glu Arg Glu Glu Asp
            35                  40                  45

Gly Asp Ser Glu Arg Trp Arg Leu Arg Ser Met Glu Ser Gln Arg Gly
 50                  55                  60

Glu Asp Gly His Ser Gly Gly Trp Arg Val Arg Arg Met Glu Thr His
 65                  70                  75                  80

Arg Lys Gly Arg Met Glu Ser Gln Glu Arg Leu Glu Thr Gly Glu Gly
                85                  90                  95

Ile Glu Thr Gln Arg Gly Glu Asp Gly Asp Ser Glu Gly Gly Arg Trp
                100                 105                 110

Arg Leu Lys Glu Asp Gly Asn Pro Gly Glu Arg Thr Glu Met Arg
            115                 120                 125

Gln Arg Leu Gly Glu Ala Gly
        130                 135
```

<210> SEQ ID NO 182
<211> LENGTH: 220
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids

<400> SEQUENCE: 182

```
Gly His Gly Val Ala Gly Xaa Cys Leu Pro Gln Pro Leu Leu Pro Pro
  1               5                   10                  15
```

-continued

```
Ser Pro Pro Asp Tyr Asp Glu Arg Ser His Leu His Asp Thr Phe Thr
            20                  25                  30

Gln Met Thr His Ala Leu Gln Glu Leu Ala Ala Ala Gln Gly Ser Phe
        35                  40                  45

Glu Val Ala Phe Pro Asp Ala Ala Glu Lys Met Lys Lys Val Phe Thr
    50                  55                  60

Gln Leu Lys Glu Ala Gln Ala Cys Ile Pro Pro Cys Glu Gly Leu Gln
65                  70                  75                  80

Glu Phe Ala Arg Arg Phe Leu Cys Ser Gly Cys Tyr Ser Arg Val Cys
                85                  90                  95

Asp Leu Pro Leu Asp Cys Pro Val Gln Asp Val Thr Val Thr Arg Gly
            100                 105                 110

Asp Gln Ala Met Phe Ser Cys Ile Val Asn Phe Gln Leu Pro Lys Glu
        115                 120                 125

Glu Ile Thr Tyr Ser Trp Lys Phe Ala Gly Gly Leu Arg Thr Gln
    130                 135                 140

Asp Leu Ser Tyr Phe Arg Asp Met Pro Arg Ala Glu Gly Tyr Leu Ala
145                 150                 155                 160

Arg Ile Arg Pro Ala Gln Leu Thr His Arg Gly Thr Phe Ser Cys Val
                165                 170                 175

Ile Lys Gln Asp Gln Arg Pro Leu Ala Arg Leu Tyr Phe Phe Leu Asn
            180                 185                 190

Val Thr Gly Arg Pro Arg Gly Arg Arg Gln Ser Cys Arg Pro Arg Ser
        195                 200                 205

Gly Lys Cys Cys Ala Gly Arg Arg Gly Met Pro Ser
    210                 215                 220

<210> SEQ ID NO 183
<211> LENGTH: 41
<212> TYPE: PRT
<213> ORGANISM: Homo sapiens

<400> SEQUENCE: 183

Gly Asp His Pro His Phe Ile Ser Val Leu Gly Lys Val Gln Arg Glu
1               5                   10                  15

Gly Arg Arg Gly Pro Glu Gly Gln Ala Glu Gly Gln Thr Glu Arg Asn
            20                  25                  30

Ser Gln Arg Arg Lys Ala Gln Arg Pro
        35                  40

<210> SEQ ID NO 184
<211> LENGTH: 129
<212> TYPE: PRT
<213> ORGANISM: Homo sapiens

<400> SEQUENCE: 184

Asn Leu Thr Ser Asp Pro Arg Pro Leu Ala Leu Pro Pro Pro Cys Gly
1               5                   10                  15

Asp Phe Ile Lys Val Thr Ser Phe Ser Pro Gly Leu Glu Thr His Thr
            20                  25                  30

Met Ala Leu Leu Ala Leu Ala Ser Ala Val Pro Ser Ala Leu Leu Ala
        35                  40                  45

Leu Ala Val Phe Arg Val Pro Ala Trp Ala Cys Leu Leu Cys Phe Thr
    50                  55                  60

Thr Tyr Ser Glu Arg Leu Arg Ile Cys Gln Met Phe Val Gly Met Arg
65                  70                  75                  80
```

-continued

```
Ser Pro Ser Leu Lys Ser Val Arg Arg Pro Ser Arg Pro Pro Ser Arg
                85                  90                  95

Ala Ser Leu Thr Pro Lys Ser Val Arg Arg Pro Ser Thr Leu His Gln
            100                 105                 110

Cys Pro Gly Glu Gly Ala Glu Gly Gly Gln Glu Arg Pro Arg Gly Ser
        115                 120                 125

Gly

<210> SEQ ID NO 185
<211> LENGTH: 13
<212> TYPE: PRT
<213> ORGANISM: Homo sapiens

<400> SEQUENCE: 185

Met Leu Val Tyr Gln Asn Gln Ala Gln Phe Ser Ser Asn
  1               5                  10

<210> SEQ ID NO 186
<211> LENGTH: 65
<212> TYPE: PRT
<213> ORGANISM: Homo sapiens

<400> SEQUENCE: 186

Met Leu Val Tyr Gln Asn Gln Ala Gln Phe Ser Ser Asn Met Trp Leu
  1               5                  10                  15

Asn Phe Ser Asp Val His Thr Tyr Leu Ser Ser Ile Ala Leu Leu Cys
             20                  25                  30

Phe Cys Leu Ser Gly Val Leu Cys Cys Ile Cys Asn Asn Ser Val Phe
         35                  40                  45

His Ile Gln Gln Tyr Ile Leu Ile Ile Thr Phe Pro Leu Val Val
     50                  55                  60

Ile
 65
```

36 HUMAN SECRETED PROTEINS

This application is a Continuation of U.S. application Ser. No. 09/382,572 filed Aug. 25, 1999, now abandoned, which is hereby incorporated by reference, which is a continuation-in-part of, and claims benefit under 35 U.S.C. §120 of copending U.S. patent application Ser. No. PCT/US99/03939, filed Feb. 24, 1999, which is hereby incorporated by reference, which claims benefit under 35 U.S.C. §119(e) based on U.S. Provisional Applications:

| Appln No. | Filing Date |
|---|---|
| 60/076,053 | 26-Feb-1998 |
| 60/076,051 | 26-Feb-1998 |
| 60/076,054 | 26-Feb-1998 |
| 60/076,052 | 26-Feb-1998 |
| 60/076,057 | 26-Feb-1998 |

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant and synthetic methods for producing the polypeptides and polynucleotides. Also provided are diagnostic methods for detecting disorders and conditions related to the polypeptides and polynucleotides, and therapeutic methods for treating such disorders and conditions. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC, at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH$_2$PO$_4$; 0.02M EDTA, pH 7.4), 0.5% SDS, 30% formamide, 100 u g/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using digo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann N.Y. Acad Sci 663:48–62 (1992).) "SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention

FEATURES OF PROTEIN ENCODED BY GENE NO: 1

Preferred polypeptides of the invention comprise the following amino acid sequence: HSSLPHFSSRI (SEQ ID:NO: 85). Polynucleotides encoding these polypeptides are also provided.

Contact of cells with supernatant expressing the product of this gene induces the expression of osteocalcin in human SOAS-2 osteoblastic cells. Osteocalcin is a protein attributed to influencing the bone mineralization of skeletal tissue, and is also thought to be useful in inhibiting osteoblast function. Thus, polynucleotides and polypeptides have uses which include, but are not limited to, inducing the expression of osteocalcin.

The polypeptide of this gene has been determined to have a transmembrane domain at about amino acid position 31–48 of the amino acid sequence referenced in Table 1 for this gene. Moreover, a cytoplasmic tail encompassing amino acids 49–55 of this protein has also been determined. Based upon these characteristics, it is believed that the protein product of this gene shares structural features to type Ia membrane proteins.

This gene is expressed primarily in in B-cell lymphoma, and to a lesser extent in brain tissue.

Therefore, polynucleotides and polypeptides of the invention are useful as reagents for differential identification of the tissue(s) or cell type(s) present in a biological sample and for diagnosis of diseases and conditions, which include, but are not limited to, diseases of the haemopoietic system and brain, including cancer. Similarly, polypeptides and antibodies directed to these polypeptides are useful in providing immunological probes for differential identification of the tissue(s) or cell type(s). For a number of disorders of the above tissues or cells, particularly of the immune and central nervous system, expression of this gene at significantly higher or lower levels is routinely detected in certain tissues or cell types (e.g., immune, central nervous system, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in B-cell lymphoma and brain tissue indicates that polynucleotides and polypeptides corresponding to this gene are useful for the diagnosis, treatment, and/or prevention of disorders of the haemopoietic system and the central nervous system, as well as cancers thereof. The expression of this gene in B-cell lymphoma indicates that this gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Alternatively, the tissue distribution in brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ D NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1427 of SEQ ID NO:11, b is an integer of 15 to 1441, where both a and b correspond to the positions of nucleotide residues shown in SEQ ID NO:11, and where b is greater than or equal to a +14.

FEATURES OF PROTEIN ENCODED BY GENE NO: 2

Preferred polypeptides of the invention comprise the following amino acid sequence: RDSNGRGDSSLLK-FVCPVPLKK (SEQ ID NO: 86). Polynucleotides encoding these polypeptides are also provided.

The gene encoding the disclosed cDNA is thought to reside on chromosome 2. Accordingly, polynucleotides related to this invention are useful as a marker in linkage analysis for chromosome 2.

This gene is expressed primarily in brain, fetal tissue, ovarian cancer, colon and hepatocellular tumor and to a lesser extent in several other tissues and organs.

Therefore, polynucleotides and polypeptides of the invention are useful as reagents for differential identification of the tissue(s) or cell type(s) present in a biological sample and for diagnosis of diseases and conditions, which include, but are not limited to, neurological and developmental diseases and cancers. Similarly, polypeptides and antibodies directed to these polypeptides are useful in providing immunological probes for differential identification of the tissue(s) or cell type(s). For a number of disorders of the above tissues or cells, particularly of the neural and developing systems, expression of this gene at significantly higher or lower levels is routinely detected in certain tissues or cell types (e.g., neurological, developing, cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 49 as residues: Ile-35 to Lys-40. Polynucleotides encoding said polypeptides are also provided.

The tissue distribution in brain and embryonic tissues indicates that polynucleotides and polypeptides corresponding to this gene are useful for the diagnosis, treatment, and/or prevention of disorders of the neural system, as well as cancer. The tissue distribution in brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2146 of SEQ ID NO:12, b is an integer of 15 to 2160, where both a and b correspond to the positions of nucleotide residues shown in SEQ ID NO:12, and where b is greater than or equal to a +14.

FEATURES OF PROTEIN ENCODED BY GENE NO: 3

Preferred polypeptides of the invention comprise the following amino acid sequence: IPEYTFRRRWFH (SEQ ID NO: 87). Polynucleotides encoding these polypeptides are also provided.

This gene is expressed primarily in breast lymph nodes, T-cells, bone marrow, brain tissue, haemopoietic cells and cancerous tissues.

Therefore, polynucleotides and polypeptides of the invention are useful as reagents for differential identification of the tissue(s) or cell type(s) present in a biological sample and for diagnosis of diseases and conditions, which include, but are not limited to, cancer and diseases of the haemopoietic and central nervous systems. Similarly, polypeptides and antibodies directed to these polypeptides are useful in providing immunological probes for differential identification of the tissue(s) or cell type(s). For a number of disorders of the above tissues or cells, particularly of the haemopoietic and central nervous systems, expression of this gene at significantly higher or lower levels is routinely detected in certain tissues or cell types (e.g., immune, neurological, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in haemopoietic and neural tissues indicates that polynucleotides and polypeptides corresponding to this gene are useful for the diagnosis, treatment, and/or prevention of disorders of the haemopoietic system, the central nervous system, and cancers thereof, particularly leukemias. Expression of this gene product in normal and cancerous lymph nodes indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Alternatively, the tissue distribution in brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1188 of SEQ ID NO:13, b is an integer of 15 to 1202, where both a and b correspond to the positions of nucleotide residues shown in SEQ ID NO:13, and where b is greater than or equal to a +14.

FEATURES OF PROTEIN ENCODED BY GENE NO: 4

Preferred polypeptides of the invention comprise the following amino acid sequence: LCVSMK-IEWGRESCEKK (SEQ ID NO: 88). Polynucleotides encoding these polypeptides are also provided.

This gene is expressed primarily in leukemia cells and fetal tissue.

Therefore, polynucleotides and polypeptides of the invention are useful as reagents for differential identification of the tissue(s) or cell type(s) present in a biological sample and for diagnosis of diseases and conditions, which include, but are not limited to, diseases of the haemopoietic system and cancer. Similarly, polypeptides and antibodies directed to these polypeptides are useful in providing immunological probes for differential identification of the tissue(s) or cell type(s). For a number of disorders of the above tissues or cells, particularly of the haemopoietic system, expression of this gene at significantly higher or lower levels is routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in leukemia cells indicates that polynucleotides and polypeptides corresponding to this gene are useful for the diagnosis, treatment, and/or prevention of disorders of the haemopoietic system and cancers thereof, particularly leukemia, as well as cancers of other tissues where expression has been observed. Furthermore, this gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1540 of SEQ ID NO:14, b is an integer of 15 to 1554, where both a and b correspond to the positions of nucleotide residues shown in SEQ ID NO:14, and where b is greater than or equal to a +14.

FEATURES OF PROTEIN ENCODED BY GENE NO: 5

Preferred polypeptides of the invention comprise the following amino acid sequence: RLKTTRAYSSQFWRPE-VQNQGVRKV (SEQ ID NO: 89). Polynucleotides encoding these polypeptides are also provided.

This gene is expressed primarily in CD-34 Positive cord blood cells.

Therefore, polynucleotides and polypeptides of the invention are useful as reagents for differential identification of the tissue(s) or cell type(s) present in a biological sample and for diagnosis of diseases and conditions, which include, but are not limited to, diseases and disorders of the immune and haemopoietic system, in addition to developing cells and tissues. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels is routinely detected in certain tissues or cell types (e.g., immune, developmental, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in CD34 (+) cells indicates that polynucleotides and polypeptides corresponding to this gene are useful for the diagnosis, treatment, and/or prevention of disorders of the haemopoietic and immune systems, including cancers thereof. Furthermore, expression of this gene product in CD34 (+) cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1526 of SEQ ID NO:15, b is an integer of 15 to 1540, where both a and b correspond to the positions of nucleotide residues shown in SEQ ID NO:15, and where b is greater than or equal to a +14.

FEATURES OF PROTEIN ENCODED BY GENE NO: 6

Preferred polypeptides of the invention comprise the following amino acid sequence: LTLCLPRSLYALPQCPGPHVHPCPALLWDRAGLPLPLPGCIHGRSQVPWHELHSPAAFNQGMMGMCTYPTPPLGRVMLRCGFLTVPRLSQEAWVWVPTVGAGV ISYLRRPPFLPVLCAPTPTLELPRFSVFVKELTLCCLPLSQCPCHSCEPAAGEVG ADLCVAG (SEQ ID NO: 90), LTLCLPRSLYALPQCPGPHVHPCPALLWDRAGLPLPLPGCI (SEQ ID NO: 91), HGRSQVPWHELHSPAAFNQGMMGMCTYPTPPLGRVMLR (SEQ ID NO: 92), CGFLTVPRLSQEAWVWVPTVGAGVISYLRRPPFLPVLCAPT (SEQ ID NO: 93), and/or PTLELPRFSVFVKELTLCCLPLSQCPCHSCEPAAGEVGADLCVAG (SEQ ID NO: 94). Polynucleotides encoding these polypeptides are also provided.

This gene is expressed primarily in lymph nodes, thymus, chronic synovitis tissues, immune cells (e.g., T-cells), ovarian tumor and to a lesser extent in several other tissues and organs.

Therefore, polynucleotides and polypeptides of the invention are useful as reagents for differential identification of the tissue(s) or cell type(s) present in a biological sample and for diagnosis of diseases and conditions, which include, but are not limited to, immune and inflammatory disorders. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels is routinely detected in certain tissues or cell types (e.g., immune, musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune tissues indicates that polynucleotides and polypeptides corresponding to this gene are useful for the diagnosis, treatment, and/or prevention of inflammatory and haemopoietic disorders. Furthermore, expression of this gene product in thymus and lymph nodes indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1043 of SEQ ID NO:16, b is an integer of 15 to 1057, where both a and b correspond to the positions of nucleotide residues shown in SEQ ID NO:16, and where b is greater than or equal to a +14.

FEATURES OF PROTEIN ENCODED BY GENE NO: 7

Preferred polypeptides of the invention comprise the following amino acid sequence: IRHETFRVRGCSISRALSPFPLPFPHPGRSGWSGPEAK (SEQ ID NO: 95). Polynucleotides encoding these polypeptides are also provided.

The gene encoding the disclosed cDNA is thought to reside on chromosome 6. Accordingly, polynucleotides related to this invention are useful as a marker in linkage analysis for chromosome 6.

The polypeptide of this gene has been determined to have transmembrane domains at about amino acid positions 298–332, 139–167, 405–432, 42–74, 361–386, 100–124, 495–517, 189–211 of the amino acid sequence referenced in Table 1 for this gene. Based upon these characteristics, it is believed that the protein product of this gene shares structural features to type IIIa membrane proteins.

This gene is expressed primarily in embryonic, placental and umbilical vein tissues, osteoblasts, T-cell lymphoma, colon, brain, osteoclastoma, hepatocellular tumor and to a lesser extent in several other tissues and organs, including cancerous tissues.

Therefore, polynucleotides and polypeptides of the invention are useful as reagents for differential identification of the tissue(s) or cell type(s) present in a biological sample and for diagnosis of diseases and conditions, which include, but are not limited to, disorders of developing organs, growth disorders, and cancer(s). Similarly, polypeptides and antibodies directed to these polypeptides are useful in providing immunological probes for differential identification of the tissue(s) or cell type(s). For a number of disorders of the above tissues or cells, particularly of the developing and fetal systems, highly vascularized tissues and cancer, expression of this gene at significantly higher or lower levels is routinely detected in certain tissues or cell types (e.g., embryonic, placental, developing, cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placental and embryonic tissues indicates that polynucleotides and polypeptides corresponding to this gene are useful for the diagnosis, treatment, and/or prevention of diseases of developing, embryonic, and/or fetal systems, as well as growth disorders and cancer (s). Furthermore, the tissue distribution in placental tissue indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus.

Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Likewise, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function.

Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2066 of SEQ ID NO:17, b is an integer of 15 to 2080, where both a and b correspond to the positions of nucleotide residues shown in SEQ ID NO:17, and where b is greater than or equal to a +14.

FEATURES OF PROTEIN ENCODED BY GENE NO: 8

The translation product of this gene shares some sequence homology to beta-transducin (see, e.g., Genbank accession number AAB52945 (AF000265.1); all references available through this accession are hereby incorporated by reference herein.).

This gene is expressed primarily in the haemopoietic system, the central nervous system, and fetal tissue, as well as in cancer(s), and to a lesser extent in several other tissues and organs.

Therefore, polynucleotides and polypeptides of the invention are useful as reagents for differential identification of the tissue(s) or cell type(s) present in a biological sample and for diagnosis of diseases and conditions, which include, but are not limited to, haemopoietic diseases, developmental disorders, central nervous system, and cancer. Similarly, polypeptides and antibodies directed to these polypeptides are useful in providing immunological probes for differential identification of the tissue(s) or cell type(s). For a number of disorders of the above tissues or cells, particularly of the central nervous system, haemopoietic system, and cancer, expression of this gene at significantly higher or lower levels is routinely detected in certain tissues or cell types (e.g., immune, neurological, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:55 as residues: Lys-37 to Ile-45. Polynucleotides encoding said polypeptides are also provided.

The tissue distribution in immune and neurological tissues indicates that polynucleotides and polypeptides corresponding to this gene are useful for the diagnosis, treatment, and/or prevention of disorders of the haemopoietic system, the central nervous system, and cancer(s). This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Alternatively, the tissue distribution indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 588 of SEQ ID NO:18, b is an integer of 15 to 602, where both a and b correspond to the positions of nucleotide residues shown in SEQ ID NO:18, and where b is greater than or equal to a +14.

FEATURES OF PROTEIN ENCODED BY GENE NO: 9

The polypeptide of this gene has been determined to have a transmembrane domain at about amino acid position 7–36 of the amino acid sequence referenced in Table 1 for this gene. Moreover, a cytoplasmic tail encompassing amino acids 26–83 of this protein has also been determined. Based upon these characteristics, it is believed that the protein product of this gene shares structural features to type Ib membrane proteins.

This gene is expressed primarily in fetal skin.

Therefore, polynucleotides and polypeptides of the invention are useful as reagents for differential identification of the tissue(s) or cell type(s) present in a biological sample and for diagnosis of diseases and conditions, which include, but are not limited to, growth and skin abnormalities. Similarly, polypeptides and antibodies directed to these polypeptides are useful in providing immunological probes for differential identification of the tissue(s) or cell type(s). For a number of disorders of the above tissues or cells, particularly of epithelial structures, expression of this gene at significantly higher or lower levels is routinely detected in certain tissues or cell types (e.g., epithelial, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal epithelium indicates that polynucleotides and polypeptides corresponding to this gene are useful for the study and/or treatment of growth and skin disorders. Furthermore, the tissue distribution indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, portwine syndrome), integumentary tumors (i.e. keratoses, Bowen's Disease, basal cell carcinoma, squamous cell carcinoma, malignant melanoma, Paget's Disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show utility as a tumor marker and immunotherapy targets for the above listed tumors and tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 615 of SEQ ID NO:19, b is an integer of 15 to 629, where both a and b correspond to the positions of nucleotide residues shown in SEQ ID NO:19, and where b is greater than or equal to a +14.

FEATURES OF PROTEIN ENCODED BY GENE NO: 10

When tested against sensory neuronal cell lines, supernatants removed from cells containing this gene activated the EGR1 assay. Thus, it is likely that this gene activates sensory neuron cells, and to a lesser extent other neuronal cells, through a signal transduction pathway. Early growth response 1 (EGR1) is a promoter associated with certain genes that induces various tissues and cell types upon activation, leading the cells to undergo differentiation and proliferation.

The polypeptide of this gene has been determined to have a transmembrane domain at about amino acid position 101–117 of the amino acid sequence referenced in Table 1 for this gene. Moreover, a cytoplasmic tail encompassing amino acids 1–100 of this protein has also been determined. Based upon these characteristics, it is believed that the protein product of this gene shares structural features to type II membrane proteins.

This gene is expressed primarily in epileptic frontal cortex tissue of the brain, and to a lesser extent in fetal heart tissue.

Therefore, polynucleotides and polypeptides of the invention are useful as reagents for differential identification of the tissue(s) or cell type(s) present in a biological sample and for diagnosis of diseases and conditions, which include, but are not limited to, neurological and cardiovascular abnormalities. Similarly, polypeptides and antibodies directed to these polypeptides are useful in providing immunological probes for differential identification of the tissue(s) or cell type(s). For a number of disorders of the above tissues or cells, particularly of the central nervous and vascular systems, expression of this gene at significantly higher or lower levels is routinely detected in certain tissues or cell types (e.g., neurological, vascular, cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:57 as residues: Pro-43 to Pro-50, Asn-65 to Gly-70. Polynucleotides encoding said polypeptides are also provided.

The tissue distribution in frontal cortex tissue of the brain and fetal heart tissue indicates that polynucleotides and polypeptides corresponding to this gene are useful for the study and/or treatment of nervous system and cardiovascular disorders. The tissue distribution in frontal cortex tissue, in conjunction with the observed biological activity data, indicates that polynucleotides and polypeptides corresponding to this gene are useful for the diagnosis and/or treatment of disorders of the brain and nervous system. Elevated expression of this gene product within the frontal cortex of the brain indicates that it is involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. Alternatively, the tissue distribution in fetal heart tissue indicates that the protein product of this gene is useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2053 of SEQ ID NO:20, b is an integer of 15 to 2067, where both a and b correspond to the positions of nucleotide residues shown in SEQ ID NO:20, and where b is greater than or equal to a +14.

FEATURES OF PROTEIN ENCODED BY GENE NO: 11

Preferred polypeptides of the invention comprise the following amino acid sequence: PDSRPEARGDHV-VRPSRGLRVTGATRSIMGPWGE-PELLVWRPEAVASEPPVP VGLEVKLGALVLLLV-LTLLCSLVPICVLRRPGANHEGSASRQKALSLVSCFAG GVFLATCLLDLLPDYLAAIDEALAALH-VTLQFPLQEFILA (SEQ ID NO: 96), PDSRPEARGDH-VVRPSRGLRVTGATRSIMGPWGEP (SEQ ID NO: 97), ELLVWRPEAVASEPPVPVGLEVKLGALVLLLVLTLLC (SEQ ID NO: 98), SLVPICVLRRPGANHEGSAS-RQKALSLVSCFAGGVF (SEQ ID NO: 99), and/or LAT-CLLDLLPDYLAAIDEALAALHVTLQFPLQEFILA (SEQ ID NO: 100). Polynucleotides encoding these polypeptides are also provided.

The gene encoding the disclosed cDNA is thought to reside on chromosome 1. Accordingly, polynucleotides related to this invention are useful as a marker in linkage analysis for chromosome 1.

The translation product of this gene shares sequence homology with the polypeptide sequence of a novel protein ETI-1, which has cytostatic activity. ETI-1 is thought to be useful as an antitumour agent. Based on the sequence similarity, the translation product of this gene is expected to share biological activities with cytostatic proteins. Such activities are known in the art and described elsewhere herein.

When tested against U937 Myeloid cell lines, supernatants removed from cells containing this gene activated the GAS assay. Thus, it is likely that this gene activates myeloid cells, and to a lesser extent other immune cells, through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

The polypeptide of this gene has been determined to have a transmembrane domains at about amino acid positions 63–83, 90–110, 121–139, 161–177 of the amino acid sequence referenced in Table 1 for this gene. Based upon these characteristics, it is believed that the protein product of this gene shares structural features to type IIIa membrane proteins.

The translation product of this gene shares some homology to CGI-08 protein (see, e.g., Genbank accession number AAD277717 (AF132942.1); all references available through this accession are hereby incorporated by reference herein.).

This gene is expressed primarily in fetal tissue, endocrine organs and cancerous tissues, such as pancreas, lung, endometrial tumors, as well as neuroblastomas, and to a lesser extent in various normal and transformed cell types.

Therefore, polynucleotides and polypeptides of the invention are useful as reagents for differential identification of the tissue(s) or cell type(s) present in a biological sample and for diagnosis of diseases and conditions, which include, but are not limited to, hormonal abnormalities and tumors. Similarly, polypeptides and antibodies directed to these polypeptides are useful in providing immunological probes for differential identification of the tissue(s) or cell type(s). For a number of disorders of the above tissues or cells, particularly of the endocrine and immune systems, expression of this gene at significantly higher or lower levels is routinely detected in certain tissues or cell types (e.g., endocrine, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:58 as residues: Lys-17 to Gln-27, Gln40 to Gly47. Polynucleotides encoding said polypeptides are also provided.

The tissue distribution in cancerous tissues such as pancreatic, lung and endometrial tumors, in conjunction with the observed biological activity data and the homology to a protein known to have cytostatic activity, indicates that polynucleotides and polypeptides corresponding to this gene are useful for the study and/or treatment of tumors of various tissue types, such as pancreas and endometrium, as well as cancers of other tissues where expression has been observed. Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Protein, as well as, antibodies directed against the protein may show utility as a tumor marker and immunotherapy targets for the above listed tumors and tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 983 of SEQ ID NO:21, b is an integer of 15 to 997, where both a and b correspond to the positions of nucleotide residues shown in SEQ ID NO:21, and where b is greater than or equal to a +14.

FEATURES OF PROTEIN ENCODED BY GENE NO: 12

Preferred polypeptides of the invention comprise the following amino acid sequence: KYILSSPLLDSLAEHKN-LVWKSFLPRNF (SEQ ID NO: 101). Polynucleotides encoding these polypeptides are also provided.

This gene is expressed primarily in leukemic spleen tissue.

Therefore, polynucleotides and polypeptides of the invention are useful as reagents for differential identification of the tissue(s) or cell type(s) present in a biological sample and for diagnosis of diseases and conditions, which include, but are not limited to, leukemia and other cancers. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in leukemic spleen tissue indicates that polynucleotides and polypeptides corresponding to this gene are useful for study and treatment of immune disorders and neoplasias, as well as cancers of other tissues where expression has been observed. Protein, as well as, antibodies directed against the protein may show utility as a tumor marker and immunotherapy targets for the above listed tumors and tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1369 of SEQ ID NO:22, b is an integer of 15 to 1383, where both a and b correspond to the positions of nucleotide residues shown in SEQ ID NO:22, and where b is greater than or equal to a +14.

FEATURES OF PROTEIN ENCODED BY GENE NO: 13

Preferred polypeptides of the invention comprise the following amino acid sequence: YGKVVDLAPLHL- DARISLSTLQQQLGQPEKALEALEPMYD-
PDTLAQDANAA QXELKLLLHRSTLLFSQGK (SEQ ID
NO:102). Polynucleotides encoding these polypeptides are
also provided.

The gene encoding the disclosed cDNA is thought to reside on chromosome 2. Accordingly, polynucleotides related to this invention are useful as a marker in linkage analysis for chromosome 2.

The translation product of this gene shares sequence homology to a transcription factor IIIC102 (see, e.g, Genbank accesssion number AAD41479 (AF133123) and Mol. Cell. Biol. 19:4944–4952, 1999; all references and information available through this accession and reference are hereby incorporated by reference herein.) which is thought to functionally interact with TFIIIB and RNA Polymerase III.

This gene is expressed primarily in haemopoietic tissues such as fetal liver/spleen, osteoblasts, tongue, testes, tonsils, T-cell lymphoma and to a lesser extent in several other normal and transformed cell types.

Therefore, polynucleotides and polypeptides of the invention are useful as reagents for differential identification of the tissue(s) or cell type(s) present in a biological sample and for diagnosis of diseases and conditions, which include, but are not limited to, immune and growth abnormalities. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, liver, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:60 as residues: Ser-31 to Arg-36, Ser-44 to Glu-55, Asp-112 to Glu-119, Lys-132 to Asn-139, Asn-148 to Leu-154, Thr-214 to Leu-220, Gly-260 to Ser-265. Polynucleotides encoding said polypeptides are also provided.

The tissue distribution in immune tissues such as fetal liver/spleen indicates that polynucleotides and polypeptides corresponding to this gene are useful for the study and/or treatment of immune disorders. Expression of this gene product in fetal liver/spleen tissue indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1499 of SEQ ID NO:23, b is an integer of 15 to 1513, where both a and b correspond to the positions of nucleotide residues shown in SEQ ID NO:23, and where b is greater than or equal to a +14.

FEATURES OF PROTEIN ENCODED BY GENE NO: 14

Preferred polypeptides of the invention comprise the following amino acid sequence: DFMETFPDFCLPLA-
PHYLGKAALWAMCPGRAWAGCGPVLRT-
SHLGPHSALP SWCNICXQAIVGAGRQRGLSEDPT-
CASHWDTKTGLVPSCGAGKGI (SEQ ID NO: 103),
DFMETFPDFCLPLAPHYLGKAAL-
WAMCPGRAWAGCGPVLRTSHL (SEQ ID NO: 104),
and/or GPHSALPSWCNICXQAIVGAGRQR-
GLSEDPTCASHWDTKTGLVPSCGAGKGI (SEQ ID NO: 105). Polynucleotides encoding these polypeptides are also provided.

The gene encoding the disclosed cDNA is thought to reside on chromosome 7. Accordingly, polynucleotides related to this invention are useful as a marker in linkage analysis for chromosome 7.

This gene is expressed primarily in cerebellum tissue, and to a lesser extent in fetal liver, synovial sarcoma, osteoclastoma, and glioblastoma.

Therefore, polynucleotides and polypeptides of the invention are useful as reagents for differential identification of the tissue(s) or cell type(s) present in a biological sample and for diagnosis of diseases and conditions, which include, but are not limited to, neurodegenerative diseases and brain tumors. Similarly, polypeptides and antibodies directed to these polypeptides are useful in providing immunological probes for differential identification of the tissue(s) or cell type(s). For a number of disorders of the above tissues or cells, particularly of the nervous and immune systems, expression of this gene at significantly higher or lower levels is routinely detected in certain tissues or cell types (e.g., nervous, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution and in cerebellum tissue and fetal liver tissue indicates that polynucleotides and polypeptides corresponding to this gene are useful for the study and/or treatment of immune, neurodegenerative and cognitive disorders and neoplasias. The tissue distribution in cerebellum tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Alternatively, expression of this gene product in fetal liver indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1030 of SEQ ID NO:24, b is an integer of 15 to 1044, where both a and b correspond to the positions of nucleotide residues shown in SEQ ID NO:24, and where b is greater than or equal to a +14.

FEATURES OF PROTEIN ENCODED BY GENE NO: 15

Preferred polypeptides of the invention comprise the following amino acid sequence: RLPQRGQWAWV-LQDALGIAFCLYMLKTIRL TKACTLLLLVLFLYDIF-FVFI TPFLTKSGSSIMVEVATGPSDSATREK-LPMVLKVPRLNSSPLALCDRPFSLLGF GDILVPGLLVAYCHRFDIQVQSSRVYF-VACTIAYGVGLLVTFVALALMQRGQ PAL-LYLVPCTLVTSCAVALWRRELGVFWTGS-GFAKVLPPSPWAPAPADGPQP PKDSATPLSPQPPSEEPATSPW-PAEQSPKSRTSEEMGAGAPMREPGSPAESEG RDQAQPSPVTQPGASA (SEQ ID NO: 106), RLPQRGQWAWVLQDALGIAFCLYMLK-TIRLPTFKACTLLLLVL (SEQ ID NO: 107), FLYDW-FVHTPFLTKSGSSIMVEVATGPSDSATREKLPMVLKV (SEQ ID NO: 108), PRLNSSPLALCDRPFSLLGFGDIL-VPGLLVAYCHRFDIQVQSSR (SEQ ID NO: 109), VYF-VACTIAYGVGLLVTFVALALMQRGQPAL-LYLVPCTLVTSC (SEQ ID NO: 110), AVALWRRELGVFWTGSGFAKVLPPSPWA-PAPADGPQPPKD (SEQ ID NO: 111), SATPLSPQPPSEE-PATSPWPAEQSPKSRTSEEMGAGAPMRE (SEQ ID NO:112), and/or PGSPAESEGRDQAQPSPVTQPGASA (SEQ ID NO: 113). Polynucleotides encoding these polypeptides are also provided.

The gene encoding the disclosed cDNA is thought to reside on chromosome 19. Accordingly, polynucleotides related to this invention are useful as a marker in linkage analysis for chromosome 19.

The polypeptide of this gene has been determined to have transmembrane domains at about amino acid positions 217–268, 293–316, 241–268, 169–194 of the amino acid sequence referenced in Table 1 for this gene. Based upon these characteristics, it is believed that the protein product of this gene shares structural features to type IIIa membrane proteins.

This gene is expressed primarily in eosinophils, brain, placental tissue, bone marrow, tumors of the pancreas and testes and to a lesser extent in various other normal and transformed tissues.

Therefore, polynucleotides and polypeptides of the invention are useful as reagents for differential identification of the tissue(s) or cell type(s) present in a biological sample and for diagnosis of diseases and conditions, which include, but are not limited to, placental, neurological and cancerous abnormalities. Similarly, polypeptides and antibodies directed to these polypeptides are useful in providing immunological probes for differential identification of the tissue(s) or cell type(s). For a number of disorders of the above tissues or cells, particularly of the placenta and central nervous system, expression of this gene at significantly higher or lower levels is routinely detected in certain tissues or cell types (e.g., neurological, placental, lung, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 62 as residues: Gly-127 to Asp-134, Gly-194 to Arg-201, His-205 to Glu-217, Pro-275 to Arg-280, Pro-287 to Gln-294, Arg-315 to Arg-325. Polynucleotides encoding said polypeptides are also provided.

The tissue distribution in brain tissue indicates that polynucleotides and polypeptides corresponding to this gene are useful for the study and/or treatment of central nervous system disorders and neoplasias. Furthermore, the tissue distribution in brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders.

Alternatively, the tissue distribution in placental tissue indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus. Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. The tissue distribution in immune tissue (bone marrow and eosinophils) indicates polynucleotides and polypeptides corresponding to this gene are useful for the diagnosis and treatment of a variety of immune system disorders. Representative uses are described in the "Immune Activity" and "infectious disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses).

Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides compris- ing a nucleotide sequence described by the general formula of a–b, where a is any integer between 1 to 2561 of SEQ ID NO:25, b is an integer of 15 to 2575, where both a and b correspond to the positions of nucleotide residues shown in SEQ ID NO:25, and where b is greater than or equal to a +14.

FEATURES OF PROTEIN ENCODED BY GENE NO: 16

Preferred polypeptides of the invention comprise the following amino acid sequence: ESSGLPALGPRRRP-WEQRWSDPITLK (SEQ ID NO: 114), and/or LTLAL-DEIRLLKKDLGLIEMKKTDSEKRFGSVS-FGRSCRLIPHALASWLQTLIL CFCCRIC (SEQ ID NO: 115). Polynucleotides encoding these polypeptides are also provided.

The gene encoding the disclosed cDNA is thought to reside on chromosome 12. Accordingly, polynucleotides related to this invention are useful as a marker in linkage analysis for chromosome 12.

The translation product of this gene shares sequence homology to a type II membrane protein (see, e.g., Genbank accession number BAA76498 (AB015631.1); all references available through this accession are hereby incorporated by reference herein.).

This gene is expressed primarily in placental and embryonic tissues, PHA activated T-cells, uterus, osteoarthritis, lung, adipose tissue and to a lesser extent in many other tissues.

Therefore, polynucleotides and polypeptides of the invention are useful as reagents for differential identification of the tissue(s) or cell type(s) present in a biological sample and for diagnosis of diseases and conditions, which include, but are not limited to, growth and immune disorders, osteoarthritis, respiratory and endocrine disorders. Similarly, polypeptides and antibodies directed to these polypeptides are useful in providing immunological probes for differential identification of the tissue(s) or cell type(s). For a number of disorders of the above tissues or cells, particularly of the developing and immune systems, expression of this gene at significantly higher or lower levels is routinely detected in certain tissues or cell types (e.g., developing, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 63 as residues: Arg-21 to Leu-26. Polynucleotides encoding said polypeptides are also provided.

The tissue distribution in placental and embryonic tissues, as well as in T-cells, indicates that polynucleotides and polypeptides corresponding to this gene are useful for the study and/or diagnosis of growth and immune disorders. Furthermore, the tissue distribution in placental and embryonic tissues indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus.

Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Alternatively, expression of this gene product in T-cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. The tissue distribution in adipose tissue indicates that polynucleotides and polypeptides corresponding to this gene are useful for the treatment of obesity and other metabolic and endocrine conditions or disorders. Furthermore, the protein product of this gene may show utility in ameliorating conditions which occur secondary to aberrant fatty-acid metabolism (e.g. aberrant myelin sheath development), either directly or indirectly. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 704 of SEQ ID NO:26, b is an integer of 15 to 718, where both a and b correspond to the positions of nucleotide residues shown in SEQ ID NO:26, and where b is greater than or equal to a +14.

FEATURES OF PROTEIN ENCODED BY GENE NO: 17

Preferred polypeptides of the invention comprise the following amino acid sequence: GRPTRPVMAIQSLH-PCPSELCCRACVXFYHWA (SEQ ID NO: 116). Polynucleotides encoding these polypeptides are also provided.

The polypeptide of this gene has been determined to have a transmembrane domain at about amino acid position 1–24 of the amino acid sequence referenced in Table 1 for this gene. Moreover, a cytoplasmic tail encompassing amino acids 21–62 of this protein has also been determined. Based upon these characteristics, it is believed that the protein product of this gene shares structural features to type Ib membrane proteins.

This gene is expressed primarily in immune cells (e.g., activated monocytes, primary dendritic cells, and GM-CSF stimulated macrophages), testes, ovary tumor and to a lesser extent in activated T-cells and adult brain.

Therefore, polynucleotides and polypeptides of the invention are useful as reagents for differential identification of the tissue(s) or cell type(s) present in a biological sample and for diagnosis of diseases and conditions, which include, but are not limited to, immune regulation and immune disorders, neural and endocrine disorders, cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 64 as residues: Thr-24 to Gly-42, Glu-53 to Gly-58. Polynucleotides encoding said polypeptides are also provided.

The tissue distribution in immune cells and leukocytes such as monocytes, macrophage, primary dendritic cells, and T-cells, indicates that polynucleotides and polypeptides corresponding to this gene are useful for the study, diagnosis and/or treatment of immune dysfuntion and other immune disorders. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells and primary dendritic cells also strongly indicates a role for this protein in immune function and immune surveillance.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function.

Potentially, this gene product is involved in synapse formation, neurotransmission, learning, cognition, homeostasis, or neuronal differentiation or survival. The tissue distribution in testes tissue indicates that polynucleotides and polypeptides corresponding to this gene are useful for the diagnosis and/or treatment of male reproductive and endocrine disorders. It may also prove to be valuable in the diagnosis and treatment of testicular cancer, as well as cancers of other tissues where expression has been observed. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 640 of SEQ ID NO:27, b is an integer of 15 to 654, where both a and b correspond to the positions of nucleotide residues shown in SEQ ID NO:27, and where b is greater than or equal to a +14.

FEATURES OF PROTEIN ENCODED BY GENE NO: 18

The translation product of this gene shares sequence homology with NADH ubiquinone oxidoreductase B15 complex (see, e.g., Genbank accession number AAD05421.1 (AF044957); all references available through this accession are hereby incorporated by reference herein.) which is thought to be important in cellular respiration and metabolism.

Preferred polypeptides of the invention comprise the following amino acid sequence: NSKNTRNERSFLKL-FRNNIHDIPLTVLENK (SEQ ID NO: 117). Polynucleotides encoding these polypeptides are also provided.

This gene is expressed primarily in fetal liver/spleen, infant brain tissues, spinal cord, prostate, multiple sclerosis and to a lesser extent in fetal kidney and adipose tissues.

Therefore, polynucleotides and polypeptides of the invention are useful as reagents for differential identification of the tissue(s) or cell type(s) present in a biological sample and for diagnosis of diseases and conditions, which include, but are not limited to, growth and developmental disorders, and adult metabolic disorders. Similarly, polypeptides and antibodies directed to these polypeptides are useful in providing immunological probes for differential identification of the tissue(s) or cell type(s). For a number of disorders of the above tissues or cells, particularly of the developmental and metabolic systems, expression of this gene at significantly higher or lower levels is routinely detected in certain tissues or cell types (e.g., immune, renal, neurological, metabolic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in a number of fetal and infant tissues, as well as the homology to NADH ubiquinone oxireductase B15 complex, indicates that polynucleotides and polypeptides corresponding to this gene are useful for the study, diagnosis and/or treatment of various developmental and growth disorders, and adult metabolic disorders, such as Tay-Sach's Disease, phenylkenonuria, galactosemia, hyperlipidemias, porphyrias, and Hurler's syndrome. Furthermore, the tissue distribution in adipose tissue indicates that polynucleotides and polypeptides corresponding to this gene are useful for the treatment of obesity and other metabolic and endocrine conditions or disorders.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function.

Potentially, this gene product is involved in synapse formation, neurotransmission, learning, cognition, homeostasis, or neuronal differentiation or survival. Furthermore, the protein product of this gene may show utility in ameliorating conditions which occur secondary to aberrant fatty-acid metabolism (e.g. aberrant myelin sheath development), either directly or indirectly. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1431 of SEQ ID NO:28, b is an integer of 15 to 1445, where both a and b correspond to the positions of nucleotide residues shown in SEQ ID NO:28, and where b is greater than or equal to a +14.

FEATURES OF PROTEIN ENCODED BY GENE NO: 19

The translation product of this gene shares sequence similarity with neuronal olfactomedin-related ER localized protein isolated from the rat (Genbank accession no. gi|442370).

Preferred polypeptides of the invention comprise the following amino acid sequence: PRVRGEGNRCWTQ-GALCHRM (SEQ ID NO: 118). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: PRVRGEGN-RCWTQGALCHRMMVALRGASALLV-LFLAAFLPPPQCTQDPAM VHYIYQRFRVLEQGLEKCTQ ATRAYIQEFQEFSKNIS-VMLGRCQTYTSEYKSAVGNLALRVERAQREIDYIQY LREADECIESEDKTLAE MLLQEAEEEKKIRTLL-NASCDNMLMGIKSLKIVKKMMDTHGSWMKDAVYN SPKVYLLIGSRNNTVWEFAN IRAFMEDNTKPAPRK-QILTLSWQGTGQVIYKGFLFFINQATSNEIIKYNLQKR TVEDRMLLPGGVGRALV YQHSPSTYIDLAVDEHGL-WAIHSGPGTHSHLVLTKIEPGTLGVEHSWDTPCRS QDAEASFLLCGVLYVVY STGGQGPHRITCIYDPLG-TISEEDLPNLFFPKRPRSHSMIHYNPRDKQLYAWNE GNIIHYKLQTKRKLTL K (SEQ ID NO: 119). Polynucleotides encoding these polypeptides are also provided.

The gene encoding the disclosed cDNA is thought to reside on chromosome 11. Accordingly, polynucleotides related to this invention are useful as a marker in linkage analysis for chromosome 11.

This gene is expressed primarily in synovial sarcoma tissue, and to a lesser extent in fetal dura mater, adipose, and hogkins' lymphoma tissues.

Therefore, polynucleotides and polypeptides of the invention are useful as reagents for differential identification of the tissue(s) or cell type(s) present in a biological sample and for diagnosis of diseases and conditions, which include, but are not limited to, cancers and other metabolic disorders. Similarly, polypeptides and antibodies directed to these polypeptides are useful in providing immunological probes for differential identification of the tissue(s) or cell type(s). For a number of disorders of the above tissues or cells, particularly of the metabolic system, expression of this gene at significantly higher or lower levels is routinely detected in certain tissues or cell types (e.g., musculo-skeletal, metabolic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 66 as residues: Tyr-76 to Lys-81, Glu-92 to Asp-99, Glu-125 to Ile-132, Asp-197 to Arg-204, Gln-241 to Glu-246, Pro-310 to Ala-316, Thr-332 to His-338, Pro-361 to Ser-366, Leu-392 to Thr-399. Polynucleotides encoding said polypeptides are also provided.

The tissue distribution in musculo-skeletal and metabolic tissues, and the sequence similarity to neuronal olfactomedin-related ER localized protein, indicates that polynucleotides and polypeptides corresponding to this gene are useful for the study, diagnosis and/or treatment of cancers and other metabolic disorders. Representative uses are described here and elsewhere herein. Furthermore, the tissue distribution indicates that polynucleotides and polypeptides corresponding to this gene are useful for the detection, treatment, and/or prevention of various endocrine disorders and cancers, particularly Addison's Disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism) , hypothallamus, and testes. Furthermore, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2006 of SEQ ID NO:29, b is an integer of 15 to 2020, where both a and b correspond to the positions of nucleotide residues shown in SEQ ID NO:29, and where b is greater than or equal to a +14.

FEATURES OF PROTEIN ENCODED BY GENE NO: 20

The translation product of this gene shares sequence homology with tissue plasminogen activator gene enhancer element which is thought to play a role in blood clotting.

Preferred polypeptides of the invention comprise the following amino acid sequence: FPCICLSGLLDLLIWR-PFSEELTKTFG (SEQ ID NO: 120). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: FPCICLSGLLD-LLIWRPFSEELTKTFGMVSLLSS YLLLLELL- SKRSLFLQWYLFFGLQCCSSFLCRKNESQCFTRL KERSAGSV (SEQ ID NO: 121). Polynucleotides encoding these polypeptides are also provided.

This gene is expressed primarily in rhabdomyosarcoma and to a lesser extent in lymphocytic leukemia.

Therefore, polynucleotides and polypeptides of the invention are useful as reagents for differential identification of the tissue(s) or cell type(s) present in a biological sample and for diagnosis of diseases and conditions, which include, but are not limited to, cancers and clotting diseases and/or disorders, such as hemophelia. Similarly, polypeptides and antibodies directed to these polypeptides are useful in providing immunological probes for differential identification of the tissue(s) or cell type(s). For a number of disorders of the above tissues or cells, particularly of the metabolic and blood clotting systems, expression of this gene at significantly higher or lower levels is routinely detected in certain tissues or cell types (e.g., hematopoietic, developmental, metabolic disorders, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 67 as residues: Cys-38 to Cys-45, Leu-49 to Ala-54. Polynucleotides encoding said polypeptides are also provided. The homology to the conserved tissue plasminogen activator gene enhancer element indicates that the protein product of this gene is useful for the study, treatment and diagnosis of cancers and blood clotting disorders. Representative uses are described here and elsewhere herein. The protein is useful for the treatment, detection, and/or prevention of metabolic and developmental disorders which include, but are not limited to diabetes, or placental aberrations. The protein is also useful for the treating and ameliorating cardiovascular conditions such as coronary artery disease, atherosclerosis, or arteriosclerosis. Moreover, the protein is useful in the detection, treatment, and/or prevention of vascular conditions, which include, but are not limited to, microvascular disease, vascular leak syndrome, aneurysm, stroke, atherosclerosis, arteriosclerosis, or embolism. Alternatively, the expression within lymphocytic leukemia cells, combined with its homology to tissue plasminogen activator indicates this gene product is involved in the regulation of cytokine production, antigen presentation, or other processes suggesting a usefulness in the treatment of cancer (e.g. by boosting immune responses).

Since the gene is expressed in cells of lymphoid origin, the natural gene product is involved in immune functions. Therefore it is also used as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, scleroderma and tissues. Moreover, the protein may represent a secreted factor that influences the differentiation or behavior of other blood cells, or that recruits hematopoietic cells to sites of injury (i.e. through modulating integrin function). In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1069 of SEQ ID NO:30, b is an integer of 15 to 1083, where both a and b correspond to the positions of nucleotide residues shown in SEQ ID NO:30, and where b is greater than or equal to a +14.

FEATURES OF PROTEIN ENCODED BY GENE NO: 21

The gene encoding the disclosed cDNA is believed to reside on chromosome 12. Accordingly, polynucleotides related to this invention are useful as a marker in linkage analysis for chromosome 12.

This gene is expressed primarily in fetal liver, fetal spleen and infant brain and to a lesser extent in human epididymus tissue.

Therefore, polynucleotides and polypeptides of the invention are useful as reagents for differential identification of the tissue(s) or cell type(s) present in a biological sample and for diagnosis of diseases and conditions, which include, but are not limited to, developmental, hematopoietic, immune, CNS, and/or reproductive diseases and/or disorders. Similarly, polypeptides and antibodies directed to these polypeptides are useful in providing immunological probes for differential identification of the tissue(s) or cell type(s). For a number of disorders of the above tissues or cells, particularly of the reproductive, developmental, and central nervous systems, expression of this gene at significantly higher or lower levels is routinely detected in certain tissues or cell types (e.g., developmental, hematopoietic, immune, CNS, reproductive, and cancerous and wounded tissues) or bodily fluids (e.g., lymph, serum, plasma, amniotic fluid, urine, bile, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 68 as residues: Pro-29 to Pro-35. Polynucleotides encoding said polypeptides are also provided.

The tissue distribution in fetal liver, fetal spleen and infant brain indicates that the protein product of this gene is useful for the study, diagnosis and treatment of reproductive, developmental, and CNS disorders. Moreover, the protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1566 of SEQ ID NO:31, b is an integer of 15 to 1580, where both a and b correspond to the positions of nucleotide residues shown in SEQ ID NO:31, and where b is greater than or equal to a +14.

FEATURES OF PROTEIN ENCODED BY GENE NO: 22

The translation product of this gene shares sequence homology with human beta-casein which is thought to be important as a milk component. This sequence encodes a homolog of the human milk protein, beta-casein. This sequence can be used in the production of recombinant human beta- casein for use as a constituent of infant formulae. Beta-casein is a phosphorylated protein which is present in milk of several species including humans in which it is the major casein subunit. This protein is believed to enhance calcium adsorbtion by chelating calcium to its phosphorylated residues and thereby keeping it in an adsorbable form. Human beta-casein is easily digestible by newborn infants and the digestive products have been found to play an important part in calcium uptake, and thus in the mineralisation of the skeleton. A digestion product of human beta-casein has been found to have opiod activity and is involved in the sleeping patterns of breast-fed infants.

Preferred polypeptides of the invention comprise the following amino acid sequence: KDTCTRMXIAALFT-IAKIWNQPKX (SEQ ID NO: 122), RHMHTYVY-CGTIHNSKDLEPTQMXDXIKKMWHLYTT-KYYAAIKKD (SEQ ID NO: 123), RKCGTYIPRNTMQP (SEQ ID NO: 124), and/or KRTEFMSFXGTWMKLEAI-ILSKLTQEEKTKHLMFSLISGS (SEQ ID NO: 125). Polynucleotides encoding these polypeptides are also provided.

This gene is expressed primarily in adult heart.

Therefore, polynucleotides and polypeptides of the invention are useful as reagents for differential identification of the tissue(s) or cell type(s) present in a biological sample and for diagnosis of diseases and conditions, which include, but are not limited to, reproductive and/or vascular disorders and diseases, particularly deficiency in milk production, atherosclerosis, or coronary artery disease. Similarly, polypeptides and antibodies directed to these polypeptides are useful in providing immunological probes for differential identification of the tissue(s) or cell type(s). For a number of disorders of the above tissues or cells, particularly of the reproductive system and mammary glands, expression of this gene at significantly higher or lower levels is routinely detected in certain tissues or cell types (e.g., reproductive, vascular, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The homology to human beta-casein indicates that the protein product of this gene is useful as a constituent of infant formulae. Representative uses are described here and elsewhere herein. Moreover, the protein is useful for the detection, treatment, and/or prevention of aberrant mammary gland function and diseases, in addition to a possible use in the developmental of novel protein expression for the isolation of heterologous proteins using the beta-casein enhancer, promoter, and encoding nucleotide sequences. Alternatively, the expression in adult heart indicates the protein is useful in the detection, treatment, and/or prevention of a variety of vascular disorders and condtions, which include, but are not limited to miscrovascular disease, vascular leak syndrome, aneurysm, stroke, embolism, thrombosis, and/or atherosclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 782 of SEQ ID NO:32, b is an integer of 15 to 796, where both a and b correspond to the positions of nucleotide residues shown in SEQ ID NO:32, and where b is greater than or equal to a +14.

FEATURES OF PROTEIN ENCODED BY GENE NO: 23

The translation product of this gene shares sequence homology with a rat protein, dendrin, which is distributed in the dendrites of neurons of the forebrain.

Preferred polypeptides of the invention comprise the following amino acid sequence: PKSDTSPASSR (SEQ ID NO: 126), PKSDTSPASSRLCWD (SEQ ID NO: 127), YVPSFLPKATGSIPSRKGGVGSEKPEV-PLQTYKEIVHCCEEQVLTLATEQTYA VEGETPIN-RLSLLLSGR VRVSQDGQFLHYIFPYQFMD-SPEWESLQPSEEGVFQVTLTAETSCSYISWPRK SLHLLLTKERYISCLFS ALLGYDISEKLYTLNDKL-FAKFGLRFDIRLPSLYHVLGPTAADAGPESEKGDE EVCEPAVSPPQATPTSL QQTPPCSTPPATTNFPAPP-TRARLSRPDSGILASRIPLQSYSQVISRGQAPLAPT HTPEL (SEQ ID NO: 128), ATGSIPSRKGGVGSEKPE-VPL (SEQ ID NO: 129), IVHCCEEQVLTLATE-QTYAVEGETP (SEQ ID NO: 130), QDGQFLTYIF-PYQFMDSPEWESL (SEQ ID NO: 131), TLTAETSCSYISWPRKSLHLLLT (SEQ D NO: 132), DIS-EKLYTLNDKLFAKFGLRFDIRL (SEQ ID NO: 133), SLY-HVLGPTAADAGPESEKGDEEVCE (SEQ ID NO: 134), and/or TTNPAPPRARLSRPDSGILASRIPLQ (SEQ ID NO: 135). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: PKSDTSPASSR LCWDMTSRRSSTLSMTSSLLSLGCALT-SAFPASTMSWVPLLQMLDQSPRRVM RKSVSQL-CPLLRPHPPLS SKHPLVLPLQLPPTFLHLLPG-PGCPGQTVAYWLLEFLSRATLKLYPGDRPLWL QPTRLNFKDHWTIFSVA SAALFCVHRMATDRHASF-PTHWKAHRQGERGHRRCQHCRYSKDLK (SEQ ID NO: 136). Polynucleotides encoding these polypeptides are also provided.

The gene encoding the disclosed cDNA is believed to reside on chromosome 3. Accordingly, polynucleotides related to this invention are useful as a marker in linkage analysis for chromosome 3.

This gene is expressed primarily in the heart and and to a lesser extent, in tonsil.

Therefore, polynucleotides and polypeptides of the invention are useful as reagents for differential identification of the tissue(s) or cell type(s) present in a biological sample and for diagnosis of diseases and conditions, which include, but are not limited to, cardiovascular diseases and/or disorders and conditions, particularly congestive heart failure. Similarly, polypeptides and antibodies directed to these polypeptides are useful in providing immunological probes for differential identification of the tissue(s) or cell type(s). For a number of disorders of the above tissues or cells, particularly of the vascular and neural sysytems, expression of this gene at significantly higher or lower levels is routinely detected in certain tissues or cell types (e.g., cardiovascular, vascular, immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 70 as residues: Met-1 to Ser-7, Asp-41 to Met-48, Pro-61 to Ser-67, Pro-121 to Trp-130, His-161 to Lys-181. Polynucleotides encoding said polypeptides are also provided.

The homology to dendrin indicates that the protein product of this gene is useful for the detection, treament, and/or prevention of neuronal diseases such as memory loss. Representative uses are described in the "Regeneration" and "Hyperproliferative Disorders" sections below, in Example 11, 15, and 18, and elsewhere herein. Moreover, polynucleotides and polypeptides corresponding to this gene are useful for the detection, treatment, and/or prevention of neurodegenerative disease states, behavioral disorders, or inflammatory conditions which include, but are not limited to Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function.

Potentially, this gene product is involved in synapse formation, neurotransmission, learning, cognition, homeostasis, or neuronal differentiation or survival. Alternatively, the expression in heart tissue indicates the protein is useful in the detection, treatment, and/or prevention of a variety of vascular disorders and condtions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1242 of SEQ ID NO:33, b is an integer of 15 to 1256, where both a and b correspond to the positions of nucleotide residues shown in SEQ ID NO:33, and where b is greater than or equal to a +14.

FEATURES OF PROTEIN ENCODED BY GENE NO: 24

Preferred polypeptides of the invention comprise the following amino acid sequence: YFSHGICSHA (SEQ ID NO: 137). Polynucleotides encoding these polypeptides are also provided.

This gene is expressed primarily in peripheral mononuclear cells, and to a lesser extent in other white blood cells such as neutrophils and lymphocytes from lymphomas.

Therefore, polynucleotides and polypeptides of the invention are useful as reagents for differential identification of the tissue(s) or cell type(s) present in a biological sample and for diagnosis of diseases and conditions, which include, but are not limited to, hematopoietic or immune disorders and conditions, particularly leukemia and lymphomas. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 71 as residues: Leu-41 to Pro-48. Polynucleotides encoding said polypeptides are also provided.

The tissue distribution in blood cells indicates that the protein product of this gene is useful for diagnosis and treatment of blood diseases such as leukemia and lymphomas. Representative uses are described in the "Immune Activity" and "infectious disease" sections below, in Example 11, 13, 14, 16, 18, 19, 20, and 27, and elsewhere herein. Moreover, the tissue distribution indicates polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1050 of SEQ ID NO:34, b is an integer of 15 to 1064, where both a and b correspond to the positions of nucleotide residues shown in SEQ ID NO:34, and where b is greater than or equal to a +14.

FEATURES OF PROTEIN ENCODED BY GENE NO: 25

The translation product of this gene was shown to have homology to a conserved ubiquitin thiolesterase (deubiquitinating enzyme) (See Genbank Accession No. sp|Q09738|UBPA_SCHPO) which is thought to be important in protein metabolism, processing, and/or regulation.

Preferred polypeptides of the invention comprise the following amino acid sequence: NSEDISQTRQEL-GLCISQRCLSDRKKSRRSGVWVRACT MQFMKHVF-PRLISPRRP (SEQ ID NO: 138), PTRHFCGTSSCLTG-TAVRCRAPAP VWSVRCPHCFRSSDAWVDPGIPDRYLQAYLL (SEQ ID NO: 139), GEAMDAEXAVAPPGCSHLGSFKVDN-WKQNLRAIYQCFVWSGTAEARKRKA KSCICH-VCGVHLNRLHSCLY CVFFGCFTKKHIHE-HAKAKRHNLAIDLMYGGIYCFLCQDYIYDKDME EIIAKEE QRKAWKMQGVGEKFSTW EPT-KRELELLKHNPKRRKITSNCTIGLR-GLINLGNTCFMNCIVQALTHTPLLRD FFLS-DRHRCEMQSPSS CLVCEMSSLFQEFGRVGRPGNSGPVPAGVPSIVSPE (SEQ ID NO: 140), VAPPGCSHLGSFKVDNWKQNLRAI (SEQ ID NO: 141), TAEARKRKAKSCICHVCGVHLNR (SEQ ID NO: 142), FTKKHIHEHAKAKRHNLAIDLMY (SEQ ID NO: 143), YDKDMEIIAKEEQRKAWKMQG (SEQ ID NO: 144), ELLKHNPKRRKITSNCTIGLRGLIN-LGN (SEQ ID NO: 145), GNTCFMNCIVQALTHTPLL-RDFFLSD (SEQ ID NO: 146), and/or EFGRVGRPGNSG-PVPAGVPS (SEQ ID NO: 147). Polynucleotides encoding these polypeptides are also provided.

This gene is expressed primarily in L428 cells, and to a lesser extent, in osteoblasts.

Therefore, polynucleotides and polypeptides of the invention are useful as reagents for differential identification of the tissue(s) or cell type(s) present in a biological sample and for diagnosis of diseases and conditions, which include, but are not limited to, skeletal diseases and/or disorders, particularly osteosarcoma or other bone diseases. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels is routinely detected in certain tissues or cell types (e.g., skeletal, metabolic, developmental, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in osteoblasts indicates that the protein product of this gene is useful for diagnosis and treatment of bone disorders such as osteoporosis. Representative uses are described in the "Regeneration" and "Hyperproliferative Disorders" sections below, in Example 11, 15, and 18, and elsewhere herein. Moreover, the homology to the ubiquitin thiolesterase indicates the protein can be used to arrest proliferation of haematopoietic cells for treating or preventing e.g. cancer especially leukaemias or lymphomas (in addition to other proliferative conditions in other cells or cell types). The protein can also be used to stimulate haematopoietic cell proliferation e.g. to produce blood cells for replacing blood cell depletion due to disease or condition e.g. immune suppression from AIDS or therapy such as chemotherapy or dialysis. The protein may also be used to suppress the immune system e.g. during organ or cell transplantation. The polynucleotides of the present invention can be used to transform cells for screening agents which inhibit DUB enzyme activity. Furthermore, the protein is useful for the detection and treatment of disorders and conditions affecting the skeletal system, in particular bone cancer, as well as, disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 741 of SEQ ID NO:35, b is an integer of 15 to 755, where both a and b correspond to the positions of nucleotide residues shown in SEQ ID NO:35, and where b is greater than or equal to a +14.

FEATURES OF PROTEIN ENCODED BY GENE NO: 26

The polypeptide of this gene has been determined to have a transmembrane domain at about amino acid position 27–43 of the amino acid sequence referenced in Table 1 for this gene. Moreover, a cytoplasmic tail encompassing amino acids 44 to 74 of this protein has also been determined. Based upon these characteristics, it is believed that the protein product of this gene shares structural features to type Ia membrane proteins.

In another embodiment, polypeptides comprising the amino acid sequence of the open reading frame upstream of the predicted signal peptide are contemplated by the present invention. Specifically, polypeptides of the invention comprise the following amino acid sequence:
NSEDISQTRQELGLCISQRCLS-
DRKKSRRSGVWVRACT MQFMKHVFPRLISPRRP-
MVQFEVEFLLFGLCFSSSSSRLVG-
SQVENFSPTPCIFQ AFRCSSLAIISMSLS (SEQ ID NO: 148). Polynucleotides encoding these polypeptides are also provided.

This gene is expressed primarily in cells from Hodgkin's lymphoma.

Therefore, polynucleotides and polypeptides of the invention are useful as reagents for differential identification of the tissue(s) or cell type(s) present in a biological sample and for diagnosis of diseases and conditions, which include, but are not limited to, hematopoietic or immune diseases and condtions, particularly Hodgkin's lymphoma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., hematopoietic, immune, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 73 as residues: Arg-47 to His-52, Gly-64 to Leu-7 1. Polynucleotides encoding said polypeptides are also provided.

The tissue distribution in Hodgkin's lymphoma indicates that the protein product of this gene is useful for diagnosis and treatment of hematopoietic and immune disorders and conditions. Representative uses are described in the "Immune Activity" and "infectious disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ D NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 590 of SEQ ID NO:36, b is an integer of 15 to 604, where both a and b correspond to the positions of nucleotide residues shown in SEQ ID NO:36, and where b is greater than or equal to a +14.

FEATURES OF PROTEIN ENCODED BY GENE NO: 27

The translation product of this gene shares sequence homology with 'AP2' tumor-specific DNA, which is thought to be important in detecting insertions or deletions in DNA sequences in tumor cells. Such mutations are markers of cancer and can be used in the diagnosis of cancer, esp. colorectal, stomach or pancreatic tumours.

Preferred polypeptides of the invention comprise the following amino acid sequence: AFPWPTS (SEQ ID NO: 149). Polynucleotides encoding these polypeptides are also provided.

This gene is expressed primarily in breast lymph nodes from a breast cancer patient, and to a lesser extent in adrenal gland and tonsils.

Therefore, polynucleotides and polypeptides of the invention are useful as reagents for differential identification of the tissue(s) or cell type(s) present in a biological sample and for diagnosis of diseases and conditions, which include, but are not limited to, reproductive and/or immune diseases and disorders, particularly cancers, such as breast cancer, colorectal cancer, and pancreatic cancer. Similarly, polypeptides and antibodies directed to these polypeptides are useful in providing immunological probes for differential identification of the tissue(s) or cell type(s). For a number of disorders of the above tissues or cells, particularly of the endocrine and digestive system, expression of this gene at significantly higher or lower levels is routinely detected in certain tissues or cell types (e.g., reproductive, immune, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 74 as residues: Ile-25 to Trp-30. Polynucleotides encoding said polypeptides are also provided.

The tissue distribution breast lymph nodes, combined with the homology to 'AP2 tumor-specific DNA sequence' indicates that the protein product or the DNA sequnce of this gene is useful for detecting insertions or deletions in DNA sequences in tumor cells. Such mutations are markers of cancer and can be used in the diagnosis of cancer, esp. colorectal, stomach and pancreatic tumours. Representative uses are described in the "Hyperproliferative Disorders" and "Regeneration" sections below and elsewhere herein. Expression within cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases, particularly those of the immune and/or hemaopoietic systems. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 798 of SEQ ID NO:37, b is an integer of 15 to 812, where both a and b correspond to the positions of nucleotide residues shown in SEQ ID NO:37, and where b is greater than or equal to a +14.

FEATURES OF PROTEIN ENCODED BY GENE NO: 28

The translation product of this gene was shown to have homology to a conserved reverse transcriptase homolog which may implicate this protein as playing a role in various DNA processing and modulatory activities (See Genbank Accession No.bbs|80120).

Preferred polypeptides of the invention comprise the following amino acid sequence: ESNFFYPYDSQLALLSS-VTCSAS (SEQ ID NO: 150), KLKIMFAFYVQVLN-QSKSIFVYSRNLIFFIHMIVSWPSFLQL-PAVHQCHQSSVHI CGVSGLFPSSNYQCL SLCQNHTVLIITTL (SEQ ID NO: 151), SILNVIPNL-SKQSFEEFDRLILKYMQKSKSKRIA KILLSNKK-TCPTKY (SEQ ID NO: 152), LPQWLRWLKYHQS-VWGKQTPVTLHYLTLDLIQEFTP (SEQ ID NO: 153), and/or IFVYSRNLIFFIHMIVSWPSFLQLPAVHQCHQS (SEQ ID NO: 154). Polynucleotides encoding these polypeptides are also provided.

This gene is expressed primarily in B-cell lymphoma.

Therefore, polynucleotides and polypeptides of the invention are useful as reagents for differential identification of the tissue(s) or cell type(s) present in a biological sample and for diagnosis of diseases and conditions, which include, but are not limited to, immune or hematopoietic disorders and condtions, particularly B-cell lymphoma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, developmental, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in B-cell lymphoma tissue indicates that the protein product of this gene is useful for diagnosis and treatment of immune or hematopoietic disorders. . Representative uses are described in the "Immune Activity" and "infectious disease" sections below, in Example 11, 13, 14, 16, 18, 19, 20, and 27, and elsewhere herein. Moreover, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses).

Since the gene is expressed in cells of lymphoid origin, the natural gene product is involved in immune functions.

Therefore it is also used as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, scleroderma and tissues. Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. In addition, the homology to a reverse transcriptase protein indicates the protein may play a vital role in DNA metabolism, processing, and/or regulatory roles which would have utility in treating or detecting developmental and proliferative disorders and conditions. The protein is useful in, but not limited to, the inhibition or enhancement of apoptosis, transcription, translation, trafficing, and other cellular functions. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1135 of SEQ ID NO:38, b is an integer of 15 to 1149, where both a and b correspond to the positions of nucleotide residues shown in SEQ ID NO:38, and where b is greater than or equal to a +14.

FEATURES OF PROTEIN ENCODED BY GENE NO: 29

Preferred polypeptides of the invention comprise the following amino acid sequence: PTGNDLVYVFPCLLSVF-SRMEEPSVFCLFFPLSILISSASRTFPGTQQVFSIVHG VTDVSAKKVQSQGRM TSTGLDFNLLPAWF-PSPTSLQPTEDLFQTGSLSRSFFCSKAF-SSSPLSPGGSPNA LTSVKEHL VSPAFLA SHSCTAESF-PRVDVIHAVPIAWIPAPLHPIQLINSWFFFFFFFF (SEQ ID NO: 155), DLVYVFPCLLSVFSRMEEPSVFCL (SEQ ID NO: 156), ISSASRTFPGTQQVFSIVHGVTDV (SEQ ID NO: 157), FNLLPAWFPSPTSLQPTEDL (SEQ ID NO: 158), FCSKAFSSSPLSPGGSPNALTSVKE (SEQ ID NO: 159), and/or TAESFPRVDVIHAVPIAWIPAPL (SEQ ID NO: 160). Polynucleotides encoding these polypeptides are also provided.

This gene is expressed primarily in B-cell lymphoma.

Therefore, polynucleotides and polypeptides of the invention are useful as reagents for differential identification of the tissue(s) or cell type(s) present in a biological sample and for diagnosis of diseases and conditions, which include, but are not limited to, immune or hematopoietic disorders, particularly B-cell lymphoma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 76 as residues: Glu-16 to Arg-21. Polynucleotides encoding said polypeptides are also provided.

The tissue distribution in B-cell lymphoma tissue indicates that the protein product of this gene is useful for diagnosis and treatment of immune or hematopoietic disorders and conditions. Representative uses are described in the "Immune Activity" and "infectious disease" sections below, in Example 11, 13, 14, 16, 18, 19, 20, and 27, and elsewhere herein. Moreover, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses).

Since the gene is expressed in cells of lymphoid origin, the natural gene product is involved in immune functions. Therefore it is also used as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, scleroderma and tissues. Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1073 of SEQ ID NO:39, b is an integer of 15 to 1087, where both a and b correspond to the positions of nucleotide residues shown in SEQ ID NO:39, and where b is greater than or equal to a +14.

FEATURES OF PROTEIN ENCODED BY GENE NO: 30

The translation product of this gene was shown to have homology to histone family of proteins. Based on the sequence similarity, the translation product of this gene is expected to share biological activities with histone proteins, in addition to other proteins having DNA binding activity. Such activities are known in the art and described elsewhere herein.

Preferred polypeptides of the invention comprise the following amino acid sequence: FSFLKPLCAPRAPWL-WLPPSSKSRVHVGPGDFRS (SEQ ID NO: 161), VCGTGGLEPNLAWVRVDNGSFPSSSPS-VPLEHPGCGCLLHPRAESMLGQETS DPCPGAASG-FVFPQWAG LGLLVHLYPSLSYAALACCVSGLYS-LPFFQALGNQPSFXQERQRRSMPLLWAS (SEQ ID NO: 162), HAGRKTVK (SEQ ID NO: 163), SFYAKMP-MERKALEMVEKCLDKYFQHLCDDLEV-FAAHAGRKTVKPEDLELL MRRQGLVTDQ (SEQ ID NO: 164), PMERKALEMVEKCLDKYFQ (SEQ ID NO: 165), EVFAAHAGRKTVKPEDLELLMR (SEQ ID NO: 166), SFPSSSPSVPLEHPGCGCLLHPRAESMLGQE (SEQ ID NO: 167), and/or YPSLSYAALACCVSGLYS-LPFTQALGN (SEQ ID NO: 168). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: FSFLKPLCA-PRAPWLWLPPSSKSRVHVGPGDFRSM-SWCCLWLCLSSVGR TGSAGPSLPFSELCSLGLLRLRPVFS-PLHSGPGKPAQFLAGEAEEVNAFALGFL STSSGVS-GEDEVEPLH DGVEEAEKKMEEEGVSVSEMEAT-GAQGPSRVEEAEGHTEVTEAEGSQGTAE ADGPGASSGDEDASGRAAS PESASSTPESLQAR-RHHQFLEPAPAPGAAVLSSEPA-EPLLVRHPPRPRTFGPRP RQDPHKAGLSHYVKLF SFYAKMPMERKALEMVEKCLDKYFQHL-CDDLEVFAAHAGRKTVKPEDLELL MRRQGLVT-DQVSLHVLVER HLPLEYRQLLIPCAYSGNSVFPAQ (SEQ ID NO: 169). Polynucleotides encoding these polypeptides are also provided.

The gene encoding the disclosed cDNA is believed to reside on chromosome 16. Accordingly, polynucleotides related to this invention are useful as a marker in linkage analysis for chromosome 16.

This gene is expressed primarily in epididymus and, to a lesser extent, in placenta and fetal liver/spleen.

Therefore, polynucleotides and polypeptides of the invention are useful as reagents for differential identification of the tissue(s) or cell type(s) present in a biological sample and for diagnosis of diseases and conditions, which include, but are not limited to, reproductive, hematopoietic, and/or immune disorders and conditions, particularly male infertility. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels is routinely detected in certain tissues or cell types (e.g., reproductive, hematopoietic, inmmune, and cancerous and wounded tissues) or bodily fluids (e.g., lymph, serum, plasma, urine, seminal fluid, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 77 as residues: His-44 to Pro-50, Glu-90 to Glu-96, Gln-111 to Glu-117, Ser-143 to Gly-151, Ala-154 to Leu-166, Pro-199 to Ala-216, Gly-264 to Asp-272. Polynucleotides encoding said polypeptides are also provided.

The tissue distribution in epididimus and placental tissue indicates that the protein product of this gene is useful for diagnosis and treatment of various reproductive disorders and conditions which include, but are not limited to infertility. Representative uses are described in the "Hyperproliferative Disorders" and "Regeneration" sections below and elsewhere herein. Moreover, the protein is useful for the treatment and diagnosis of conditions concerning proper testicular function (e.g. endocrine function, sperm maturation), as well as cancer. Therefore, this gene product is useful in the treatment of impotence, and could be useful as a contraceptive, either directly or indirectly. Considering the homology to histone proteins, this gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product is expressed in other specific tissues or organs where it may play related functional roles in other processes, such as hematopoiesis, inflammation, bone formation, and kidney function, to name a few possible target indications. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1262 of SEQ ID NO:40, b is an integer of 15 to 1276, where both a and b correspond to the positions of nucleotide residues shown in SEQ ID NO:40, and where b is greater than or equal to a +14.

FEATURES OF PROTEIN ENCODED BY GENE NO: 31

The translation product of this gene was shown to have homology to serine/threonine phosphatase proteins. Based on the sequence similarity, the translation product of this gene is expected to share biological activities with proteins involved in signal transduction and/or the cell cycle. Such activities are known in the art and described elsewhere herein.

Preferred polypeptides of the invention comprise the following amino acid sequence: APGGVNSEGRGQHLPP-PXL AVCLKLHL (SEQ ID NO: 170). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: APGGVNSEG-RGQHLPPPXL AVCLKLHLMSLPIPWLSLP-PCPILGQPAGLLLWLFRPFSQCCQCPWEGRASLR HPNGPSGCREAEAWPQR SLLRQQLQQAHPLPTLPT-PERLPEQMLFPSSSSKPFSLLSLTIWARLVGRLTNRI CPVPPGSVASSMSLQ AGRCGNPVVLPQPMPPGLLC-MNECSLVPGLGRGQVNSRV (SEQ ID NO: 171). Polynucleotides encoding these polypeptides are also provided.

The gene encoding the disclosed cDNA is believed to reside on chromosome 9. Accordingly, polynucleotides related to this invention are useful as a marker in linkage analysis for chromosome 9.

This gene is expressed primarily in breast and infant brain and, to a lesser extent, in neutrophils, fetal spleen, and activated monocytes.

Therefore, polynucleotides and polypeptides of the invention are useful as reagents for differential identification of the tissue(s) or cell type(s) present in a biological sample and for diagnosis of diseases and conditions, which include, but are not limited to, reproductive, developmental, immune, and/or hematopoletic disorders, particularly breast cancer. Similarly, polypeptides and antibodies directed to these polypeptides are useful in providing immunological probes for differential identification of the tissue(s) or cell type(s). For a number of disorders of the above tissues or cells, particularly of the immune and metabolic systems, expression of this gene at significantly higher or lower levels is routinely detected in certain tissues or cell types (e.g., reproductive, developmental, immune, hematopoietic, and cancerous and wounded tissues) or bodily fluids (e.g., lymph, serum, plasma, urine, amniotic fluid, breast milk, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 78 as residues: Pro-37 to Ala-42, Leu-44 to Cys-53, Glu-57 to Leu-65, Pro-79 to Pro-85. Polynucleotides encoding said polypeptides are also provided.

The tissue distribution in breast tissue and neutrophils indicates that the protein product of this gene is useful for diagnosis and treatment of certain cancers including those of reproductive and immune cell origin. Representative uses are described in the "Immune Activity" and "infectious disease" sections below, in Example 11, 13, 14, 16, 18, 19, 20, and 27, and elsewhere herein. Similarly, polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Moreover, the expression within various fetal and infant tissues indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2069 of SEQ ID NO:41, b is an integer of 15 to 2083, where both a and b correspond to the positions of nucleotide residues shown in SEQ ID NO:41, and where b is greater than or equal to a +14.

FEATURES OF PROTEIN ENCODED BY GENE NO: 32

Preferred polypeptides of the invention comprise the following amino acid sequence: NSAEPAWVPVCARGG-GAGCGRRRGRRFCAAGAVPAAERGGENGS (SEQ ID NO: 172), SLVPALK EVVVLWRRQMV-LYLVWAFIPESWLNSLGLTYWPQKY-WAVALPVYLLIAIVI GYVLLFGINMMSTSPLDSI HTITDNYAKNQQQKKYQEEAIPALRDI- SISEVNQMFFLAAKELYTKN (SEQ ID NO: 173), MVLYLVWAFIPESWLNSLGLTYWPQKYW (SEQ ID NO: 174), YWAVALPVYLLIAIVIGYVLLFGIN (SEQ ID NO: 175), and/or QQQKKYQEEAIPALRDISISEV (SEQ ID NO: 176). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: NSAEPAWVPV-CARGGGAGCGRRRGRRFCAAGAV-PAAERGGENGSMVSRST SLTLIVFLFHRLSKAPGKMV ENSPSPLPERAIYGFV-LFLSSQFGFKNLKGSRVC (SEQ ID NO: 177). Polynucleotides encoding these polypeptides are also provided.

This gene is expressed primarily in fetal liver/spleen.

Therefore, polynucleotides and polypeptides of the invention are useful as reagents for differential identification of the tissue(s) or cell type(s) present in a biological sample and for diagnosis of diseases and conditions, which include, but are not limited to, immune, hematopoietic, and/or developmental disorders and conditions, particularly haemopoiesis, leukemias, and lymphomas. Similarly, polypeptides and antibodies directed to these polypeptides are useful in providing immunological probes for differential identification of the tissue(s) or cell type(s). For a number of disorders of the above tissues or cells, particularly of the haemopoietic system, expression of this gene at significantly higher or lower levels is routinely detected in certain tissues or cell types (e.g., immune, hematopoietic, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid,from an individual not having the disorder.

Preferred polypeptides of the present invention comprise immunogenic epitopes shown in SEQ ID NO: 79 as residues: Asn-28 to Pro-34. Polynucleotides encoding said polypeptides are also provided.

The tissue distribution in fetal liver/spleen indicates that the protein product of this gene is useful for diagnosis and treatment of disorders involving haemopoiesis. Representative uses are described in the "Immune Activity" and "infectious disease" sections below, in Example 11, 13, 14, 16, 18, 19, 20, and 27, and elsewhere herein. Moreover, polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell xevivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Expression within fetal tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1002 of SEQ ID NO:42, b is an integer of 15 to 1016, where both a and b correspond to the positions of nucleotide residues shown in SEQ ID NO:42, and where b is greater than or equal to a +14.

FEATURES OF PROTEIN ENCODED BY GENE NO: 33

Preferred polypeptides of the invention comprise the following amino acid sequence: LSPRLFDAGILLWGAS-VNVTIWEVRXAQSSAS (SEQ ID NO: 178). Polynucleotides encoding these polypeptides are also provided. n another embodiment, polypeptides comprising the amino acid sequence of the open reading frame upstream of the predicted signal peptide are contemplated by the present invention. Specifically, polypeptides of the invention comprise the following amino acid sequence: LSPRLFDAGILL-WGASVNVTIWEVRXAQSSASMLPSAWG-PLQVASFFLLSFXF CFLSSSPHLGRQETHXVVLEDDEGAPC-PAEDELALQDNGFLSKNEVLRTRCL GSRSGSASAT-PPTTSGTARAARPPSQC (SEQ ID NO: 179). Polynucleotides encoding these polypeptides are also provided.

The gene encoding the disclosed cDNA is believed to reside on chromosome 10. Accordingly, polynucleotides related to this invention are useful as a marker in linkage analysis for chromosome 10.

This gene is expressed primarily in Jurkat T-cell G1 phase and to a lesser extent in 12 Week Old Early Stage Human.

Therefore, polynucleotides and polypeptides of the invention are useful as reagents for differential identification of the tissue(s) or cell type(s) present in a biological sample and for diagnosis of diseases and conditions, which include, but are not limited to, immune, hematopoietic, and/or developmental diseases and conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g., immune, hematopoietic, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in Jurkat cells indicates that the protein product of this gene is useful for diagnosis and treatment of certain immune disorders, especially involving Jurkat cells. Representative uses are described in the "Immune Activity" and "infectious disease" sections below, in Example 11, 13, 14, 16, 18, 19, 20, and 27, and elsewhere herein. Moreover, this gene product is involved in the regulation of cytokine production, antigen presentation, or other processes suggesting a usefulness in the treatment of cancer (e.g. by boosting immune responses).

Since the gene is expressed in cells of lymphoid origin, the natural gene product is involved in immune functions. Therefore it is also used as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, scieroderma and tissues. Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Expression within embryonic tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2183 of SEQ ID NO:43, b is an integer of 15 to 2197, where both a and b correspond to the positions of nucleotide residues shown in SEQ ID NO:43, and where b is greater than or equal to a +14.

FEATURES OF PROTEIN ENCODED BY GENE NO: 34

Preferred polypeptides of the invention comprise the following amino acid sequence: NLTSDPRPLALPPPCGD-FIKVTSFSPGLETHT (SEQ ID NO: 180), EQQRLR-DRETQTGXDSRAKTQRGEDGESERGRWR-LREGEDGDSEREEDGDS ERWRLRSMESQRGEDGHSGGWRVR-RMETHRKGRMESQERLETGEGWFQ RGEDGDSEG-GRWRLKEDGNPGERRTEMRQRLGEAG (SEQ ID NO: 181), GHGVAGXCLPQPLLPPSPPDYDERSHLH-DTFTQMTHALQELAAAQGSFEVAF PDAAEK-MKKVFTQLKEAQACIPPCEGLQEFAR-RFLCSGCYSRVCDLPLDCPV QDVTVTRGDQAMFSCIVNFQLPKEE-ITYSWKFAGGGLRTQDLSYFRDMPRAE GYLARIR-PAQLTHRGTFSCVIKQDQRPLARLYF-FLNVTGRPRGRRQSCRPRSG KCCAGRRGMPS (SEQ ID NO: 182), and/or GDHPHFISVLGKVQREGRRG-PEGQAEGQTERNSQRRKAQRP (SEQ ID NO: 183). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: NLTSDPRPLA-LPPPCGDFIKVTSFSPGLETHTMALLA LASAVPSAL-LALAVFRVPAWACLLCFTTYSERLRICQMFVGM RSPSLKSVRR PSRPPSRASLTPKSVRRP STLHQCPGE-GAEGGQERPRGSG (SEQ ID NO: 184). Polynucleotides encoding these polypeptides are also provided.

This gene is expressed primarily in uterine cancer and, to a lesser extent, in macrophage and adult testis.

Therefore, polynucleotides and polypeptides of the invention are useful as reagents for differential identification of the tissue(s) or cell type(s) present in a biological sample and for diagnosis of diseases and conditions, which include, but are not limited to, reproductive diseases and conditions, particularly uterine and testicular cancer. Similarly, polypeptides and antibodies directed to these polypeptides are useful in providing immunological probes for differential identification of the tissue(s) or cell type(s). For a number of disorders of the above tissues or cells, particularly of the reproductive and immune systems, expression of this gene at significantly higher or lower levels is routinely detected in certain tissues or cell types (e.g., reproductive, and cancerous and wounded tissues) or bodily fluids (e.g., lymph, serum, plasma, urine, seminal fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 81 as residues: Ser-54 to Arg-64, Lys-70 to Thr-77, Gly-88 to Ser-96. Polynucleotides encoding said polypeptides are also provided.

The tissue distribution in uterine and testis tissue indicates that the protein product of this gene is useful for diagnosis and treatment of certain cancers, including uterine cancer. Representative uses are described in the "Hyperproliferative Disorders" and "Regeneration" sections below and elsewhere herein. Moreover, the tissue distribution in testis tissue indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product is expressed in other specific tissues or organs where it may play related functional roles in other processes, such as hematopoiesis, inflammation, bone formation, and kidney function, to name a few possible target indications. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1985 of SEQ ID NO:44, b is an integer of 15 to 1999, where both a and b correspond to the positions of nucleotide residues shown in SEQ ID NO:44, and where b is greater than or equal to a +14.

FEATURES OF PROTEIN ENCODED BY GENE NO: 35

Preferred polypeptides of the invention comprise the following amino acid sequence: MLVYQNQAQFSSN (SEQ ID NO: 185). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: MLVYQNQAQF-SSNMWLNFSDVHTYLSSIALLC FCLSGVLCCICNNS-VFHIQQYILIFTPLVVI (SEQ ID NO: 186). Polynucleotides encoding these polypeptides are also provided.

This gene is expressed primarily in the cerebellum.

Therefore, polynucleotides and polypeptides of the invention are useful as reagents for differential identification of the tissue(s) or cell type(s) present in a biological sample and for diagnosis of diseases and conditions, which include, but are not limited to, neurodegenerative disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels is routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in cerebellum indicates that the protein product of this gene is useful for the diagnosis and treatment of neurodegenerative disorders. Moreover, polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function.

Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1505 of SEQ ID NO:45, b is an integer of 15 to 1519, where both a and b correspond to the positions of nucleotide residues shown in SEQ ID NO:45, and where b is greater than or equal to a +14.

FEATURES OF PROTEIN ENCODED BY GENE NO: 36

This gene is expressed primarily in cerebellum and whole brain and to a lesser extent in pineal gland, fetal liver/spleen, and ovary.

Therefore, polynucleotides and polypeptides of the invention are useful as reagents for differential identification of the tissue(s) or cell type(s) present in a biological sample and for diagnosis of diseases and conditions, which include, but are not limited to, neurodegenerative diseases and/or disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels is routinely detected in certain tissues or cell types (e.g., neural, endocrine, developmental, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO: 83 as residues: His-3 to Phe-11, Pro-35 to Arg-40. Polynucleotides encoding said polypeptides are also provided.

The tissue distribution in cerebellum and whole brain indicates that the protein product of this gene is useful for the diagnosis and treatment of neurodegenerative disorders involving the cerebellum or other brain regions. Moreover, polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function.

Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1175 of SEQ ID NO:46, b is an integer of 15 to 1189, where both a and b correspond to the positions of nucleotide residues shown in SEQ ID NO:46, and where b is greater than or equal to a +14.

| Gene No. | cDNA Clone ID | ATCC Deposit Nr and Date | Vector | NT SEQ ID NO: X | Total NT Seq. | 5' NT of Clone Seq. | 3' NT of Clone Seq. |
|---|---|---|---|---|---|---|---|
| 1 | HCE1Q30 | 209626 02/12/98 | Uni-ZAP XR | 11 | 1441 | 1 | 1441 |
| 2 | HAGBP70 | 209626 02/12/98 | Uni-ZAP XR | 12 | 2160 | 163 | 2142 |
| 3 | HBCAY27 | 209626 02/12/98 | Uni-ZAP XR | 13 | 1202 | 447 | 1202 |
| 4 | HCACU58 | 209626 02/12/98 | Uni-ZAP XR | 14 | 1554 | 1 | 1554 |
| 5 | HCWLD74 | 209626 02/12/98 | ZAP Express | 15 | 1540 | 1 | 1540 |
| 6 | HDPFP29 | 209626 02/12/98 | pCMVSport 3.0 | 16 | 1057 | 1 | 1057 |
| 7 | HDPPH47 | 209626 02/12/98 | pCMVSport 3.0 | 17 | 2080 | 105 | 2080 |
| 8 | HFEAN33 | 209626 02/12/98 | Uni-ZAP XR | 18 | 602 | 1 | 602 |

-continued

| | | | | | | | |
|---|---|---|---|---|---|---|---|
| 9 | HFEAT91 | 209626 02/12/98 | Uni-ZAP XR | 19 | 629 | 1 | 629 |
| 10 | HFPAO71 | 209626 02/12/98 | Uni-ZAP XR | 20 | 2067 | 364 | 2067 |
| 11 | HLWAA17 | 209626 02/12/98 | pCMVSport 3.0 | 21 | 997 | 246 | 997 |
| 12 | HLYCQ18 | 209626 02/12/98 | pSport1 | 22 | 1383 | 1 | 1383 |
| 13 | HOSFG70 | 209626 02/12/98 | Uni-ZAP XR | 23 | 1513 | 203 | 1513 |
| 14 | HSSAJ29 | 209626 02/12/98 | Uni-ZAP XR | 24 | 1044 | 1 | 1044 |
| 15 | HUSIF44 | 209626 02/12/98 | pSport1 | 25 | 2575 | 1 | 2575 |
| 15 | HUSIF44 | 209626 02/12/98 | pSport1 | 47 | 2584 | 1 | 2584 |
| 16 | H6EDX46 | 209626 02/12/98 | Uni-ZAP XR | 26 | 718 | 1 | 718 |
| 17 | HABAG37 | 209626 02/12/98 | pSport1 | 27 | 654 | 1 | 639 |
| 18 | HACBD91 | 209626 02/12/98 | Uni-ZAP XR | 28 | 1445 | 1 | 1445 |
| 19 | HADEH21 | 209626 02/12/98 | pSport1 | 29 | 2020 | 1 | 2020 |
| 20 | HAGHD57 | 209626 02/12/98 | Uni-ZAP XR | 30 | 1083 | 97 | 1083 |
| 21 | HAGHR69 | 209626 02/12/98 | Uni-ZAP XR | 31 | 1580 | 1 | 1450 |
| 22 | HAHDB16 | 209626 02/12/98 | Uni-ZAP XR | 32 | 796 | 1 | 796 |
| 23 | HAHDR32 | 209626 02/12/98 | Uni-ZAP XR | 33 | 1256 | 365 | 1256 |
| 24 | HAJAW93 | 209626 02/12/98 | pCMVSport 3.0 | 34 | 1064 | 45 | 1064 |
| 25 | HAJBR69 | 209626 02/12/98 | pCMVSport 3.0 | 35 | 755 | 1 | 755 |
| 26 | HAMGO32 | 209626 02/12/98 | pCMVSport 3.0 | 36 | 604 | 1 | 604 |
| 27 | HATBR65 | 209626 02/12/98 | Uni-ZAP XR | 37 | 812 | 1 | 812 |
| 28 | HBJLD29 | 209626 02/12/98 | Uni-ZAP XR | 38 | 1149 | 1 | 1149 |
| 29 | HBJNB13 | 209626 02/12/98 | Uni-ZAP XR | 39 | 1087 | 1 | 1087 |
| 30 | HCE2F54 | 209626 02/12/98 | Uni-ZAP XR | 40 | 1276 | 19 | 1256 |
| 31 | HCE3C52 | 209626 02/12/98 | Uni-ZAP XR | 41 | 2083 | 119 | 2074 |
| 32 | HCEEA88 | 209626 02/12/98 | Uni-ZAP XR | 42 | 1016 | 1 | 1016 |
| 33 | HCEFE96 | 209626 02/12/98 | Uni-ZAP XR | 43 | 2197 | 1 | 2197 |
| 34 | HCEIF12 | 209626 02/12/98 | Uni-ZAP XR | 44 | 1999 | 1 | 1999 |
| 35 | HCEOR67 | 209626 02/12/98 | Uni-ZAP XR | 45 | 1519 | 1 | 1519 |
| 36 | HCEVB76 | 209626 02/12/98 | Uni-ZAP XR | 46 | 1189 | 1 | 1189 |

| Gene No. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|
| 1 | 137 | 137 | 48 | 1 | 30 | 31 | 55 |
| 2 | 360 | 360 | 49 | 1 | 34 | 35 | 40 |
| 3 | 580 | 580 | 50 | 1 | 18 | 19 | 93 |
| 4 | 137 | 137 | 51 | 1 | 30 | 31 | 83 |
| 5 | 138 | 138 | 52 | 1 | 21 | 22 | 65 |
| 6 | 293 | 293 | 53 | 1 | 30 | 31 | 52 |
| 7 | 116 | 116 | 54 | 1 | 35 | 36 | 540 |
| 8 | 25 | 25 | 55 | 1 | 26 | 27 | 177 |
| 9 | 21 | 21 | 56 | 1 | 32 | 33 | 83 |
| 10 | 414 | 414 | 57 | 1 | 33 | 34 | 131 |
| 11 | 436 | 436 | 58 | 1 | 15 | 16 | 187 |
| 12 | 126 | 126 | 59 | 1 | 34 | 35 | 40 |
| 13 | 257 | 257 | 60 | 1 | 23 | 24 | 338 |
| 14 | 103 | 103 | 61 | 1 | 25 | 26 | 47 |
| 15 | 27 | 27 | 62 | 1 | 25 | 26 | 336 |
| 15 | 29 | 29 | 84 | 1 | 28 | 29 | 132 |

-continued

| | | | | | | | |
|---|---|---|---|---|---|---|---|
| 16 | 128 | 128 | 63 | 1 | 20 | 21 | 84 |
| 17 | 97 | 97 | 64 | 1 | 31 | 32 | 62 |
| 18 | 117 | 117 | 65 | 1 | 42 | 43 | 49 |
| 19 | 61 | 61 | 66 | 1 | 25 | 26 | 401 |
| 20 | 402 | 402 | 67 | 1 | 24 | 25 | 57 |
| 21 | 11 | 11 | 68 | 1 | 21 | 22 | 72 |
| 22 | 93 | 93 | 69 | 1 | 20 | 21 | 50 |
| 23 | 435 | 435 | 70 | 1 | 25 | 26 | 181 |
| 24 | 218 | 218 | 71 | 1 | 30 | 31 | 48 |
| 25 | 262 | 262 | 72 | 1 | 19 | 20 | 53 |
| 26 | 119 | 119 | 73 | 1 | 22 | 23 | 74 |
| 27 | 252 | 252 | 74 | 1 | 16 | 17 | 64 |
| 28 | 142 | 142 | 75 | 1 | 29 | 30 | 43 |
| 29 | 12 | 12 | 76 | 1 | 17 | 18 | 52 |
| 30 | 166 | 166 | 77 | 1 | 19 | 20 | 319 |
| 31 | 236 | 236 | 78 | 1 | 33 | 34 | 171 |
| 32 | 134 | 134 | 79 | 1 | 23 | 24 | 60 |
| 33 | 121 | 121 | 80 | 1 | 26 | 27 | 100 |
| 34 | 198 | 198 | 81 | 1 | 15 | 16 | 97 |
| 35 | 155 | 155 | 82 | 1 | 27 | 28 | 52 |
| 36 | 105 | 105 | 83 | 1 | 37 | 38 | 40 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID. "Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, or a deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using techniques described herein or otherwise known in the art, such as, for example, antibodies of the invention raised against the secreted protein.

The present invention provides a polynucleotide comprising, or alternatively consisting of, the nucleic acid sequence of SEQ ID NO:X, and/or a cDNA contained in ATCC deposit Z. The present invention also provides a polypeptide comprising, or alternatively, consisting of, the polypeptide sequence of SEQ ID NO:Y and/or a polypeptide encoded by the cDNA contained in ATCC deposit Z. Polynucleotides encoding a polypeptide comprising, or alternatively consisting of the polypeptide sequence of SEQ ID NO:Y and/or a polypeptide sequence encoded by the cDNA contained in ATCC deposit Z are also encompassed by the invention.

Signal Sequences

The present invention also encompasses mature forms of the polypeptide having the polypeptide sequence of SEQ ID NO:Y and/or the polypeptide sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. According to th4e signal hypothesis, proteins secreted by mammalian cells have a signal or secretary leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as desribed below). These polypeptides, and the polynucleotides encoding such polypeptides, are contemplated by the present invention.

Polynucleotide and Polypeptide Variants

The present invention is directed to variants of the polynucleotide sequence disclosed in SEQ ID NO:X, the complementary strand thereto, and/or the cDNA sequence contained in the deposited clone.

The present invention also encompasses variants of the polypeptide sequence disclosed in SEQ ID NO:Y and/or encoded by the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:X or the complementary strand thereto, the nuclotide coding sequence contained in a deposited cDNA clone or the complementary strand thereto, a nucleotide sequence encoding the polypeptide of SEQ ID NO:Y, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:Y, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequnce are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, an amino acid sequences shown in Table 1 (SEQ ID NO:Y) or to the amino acid sequence encoded by cDNA contained in a deposited clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N-or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N-and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N-and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as $E.\ coli$).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268:2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is also directed to polynucleotide fragments of the polynucleotides of the invention.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portioon of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Epitopes & Antibodies

The present invention is also directed to polypeptide fragments comprising, or alternatively consisting of, an epitope of the polypeptide sequence shown in SEQ ID NO:Y, or the polypeptide sequence encoded by the cDNA contained in a deposited clone. Polynucleotides encoding these epitopes (such as, for example, the sequence disclosed in SEQ ID NO:X) are also encompassed by the invention, is the nucleotide sequences of the complementary strand of the polynucleotides encoding these epitopes. And polynucleotides which hybridize to the complementary strand under stringent hybridization conditions or lower stringency conditions.

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Nati. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.) In the present invention, antigenic epitopes preferably contain a sequence of at least 4, at least 5, at least 6, at least 7, more preferably at least 8, at least 9, at least 10, at least 15, at least 20, at least 25, and most preferably between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. (See, for instance, Wilson et al., Cell 37:767–778 (1984); Sutcliffe et al., Science 219:660–666 (1983).)

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.) Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al., Nature, 331:84–86 (1988). Fusion proteins that have a disulfide-linked dimeric structure due to the IgG portion can also be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides corresponding to SEQ ED NO:Y thereby effectively generating agonists and antagonists of the polypeptides. See, generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S., Trends Biotechnol. 16(2):76–82 (1998); Hansson, L. O., et al., J. Mol. Biol. 287:265–76 (1999); and Lorenzo, M. M. and Blasco, R., Biotechniques 24(2):308–13 (1998) (each of these patents and publications are hereby incorporated by reference). In one embodiment, alteration of polynucleotides corresponding to SEQ ID NO:X and corresponding polypeptides may be achieved by DNA shuffling. DNA shuffling involves the assembly of two or more DNA segments into a desired molecule corresponding to SEQ ID NO:X polynucleotides of the invention by homologous, or site-specific, recombination. In another embodiment, polynucleotides corresponding to SEQ ID NO:X and corresponding polypeptides may be altered by being subjected to random mutagenesis by error-prone PCR, random nucleotide insertion or other methods prior to recombination. In another embodiment, one or more components, motifs, sections, parts, domains, fragments, etc., of coding polynucleotide corresponding to SEQ ID NO:X, or the polypeptide encoded thereby may be recombined with one or more components, motifs, sections, parts, domains, fragments, etc. of one or more heterologous molecules.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and human polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, et al., J. Immunol. 147:60–69 (1991); U.S. Pat. Nos. 5,573,920, 4,474,893, 5,601,819, 4,714,681, 4,925,648; Kostelny et al., J. Immunol. 148:1547–1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not a limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al.; Eur. J. Immunol. 24:952–958 (1994); Persic et al., Gene 187 9–18 (1997); Burton et al., Advances in Immunology 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu, L. et al.,.PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; and U.S. Pat. No. 5,807,715. Antibodies can be humanized using a variety of techniques including CDR-grafting (EP 0 239 400; WO 91/09967; U.S. Pat. No. 5,530,101; and 5,585,089), veneering or resurfacing (EP 0 592 106; EP 0 519 596; Padlan E. A., Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452 (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi et al., PNAS 88:10535–10539 (1991); Zheng et al., J. Immunol. 154:5590–5600 (1995); and Vil et al., PNAS 89:11337–11341 (1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng et al., Blood 92(6) :1981–1988 (1998); Chen, et al., Cancer Res. 58(16) :3668–3678 (1998); Harrop et al., J. Immunol. 161(4) :1786–1794 (1998); Zhu et al., Cancer Res. 58(15) :3209–3214 (1998); Yoon, et al., J. Immunol. 160(7) :3170–3179 (1998); Prat et al., J. Cell. Sci. 111 (Pt2) :237–247 (1998); Pitard et al., J. Immunol. Methods 205(2) :177–190 (1997); Liautard et al., Cytokinde 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (said references incorporated by reference in their entireties).

As discussed above, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to ligand can be used to generate anti-idiotypes that "mimic" the polypeptide mutimerization and/ or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of irmunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394, 827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci.

USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors. Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293, and *Bowes melanoma* cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4- diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodarine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Fer-rantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1–2,3-dioleyloxy)propyl]-N,N,N-triethylamnmonium (DOTMA) liposomes are particularly useful and are available under the trademark Lipofectin, from GIBCO BRL, Grand Island, N.Y. (See, also, Felgner et al., Proc. Natl.

Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijistra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5'and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding other angiongenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281(1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly Biological Activities The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating or detecting deficiencies or disorders of hematopoietic cells. A polynucleotides or polypeptides, or agonists or antagonists of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. These molecules could be important in the treatment of heart attacks (infarction), strokes, or scarring.

A polynucleotides or polypeptides, or agonists or antagonists of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat and/or prevent organ rejection or graft-versus-host disease (GVHD). Organ rejection occurs by host inmmune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat or detect hyperproliferative disorders, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotides or polypeptides, or agonists or antagonists of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotides or polypeptides, or agonists or antagonists of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Cardiovascular Disorders

Polynucleotides or polypeptides, or agonists or antagonists of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease. As shown in the Examples, administration of polynucleotides and polypeptides of the invention to an experimentally induced ischemia rabbit hindlimb may restore blood pressure ratio, blood flow, angiographic score, and capillary density.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a pharmaceutical composition, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.*, 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442447 (1987).

The present invention provides for treatment of diseases or disorders associated with neovascularization by administration of the polynucleotides or polypeptides, or agonists or antagonists of the invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).

Ocular disorders associated with neovascularization which can be treated with the polynucleotides or polypeptides or agonists or antagonists of the invention include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978). Additionally, disorders which can be treated with the polynucleotides and polypeptides of the present invention (including agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with polynucleotides or polypeptides or agonists or antagonists of the present invention, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

Diseases at the Cellular Level

Diseases associated with increased cell survival or the inhibition of apoptosis that could be treated or detected by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metasis of cancers, in particular those listed above.

Additional diseases or conditions associated with increased cell survival that could be treated or detected by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by the polynucleotides or polypeptides, and/or agonists or antagonists of the invention, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischernic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intesting, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/ or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Infectious Disease

A polypeptide or polynucleotide and/or agonist or antagonist of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated or detected by a polynucleotide or polypeptide and/or agonist or antagonist of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide, and/or agonist or antagonist of the present invention can be used to treat or detect any of these symptoms or diseases.

Similarly, bacterial or fungal agents that can cause disease or symptoms and that can be treated or detected by a polynucleotide or polypeptide and/or agonist or antagonist of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide and/or agonist or antagonist of the present invention can be used to treat or detect any of these symptoms or diseases.

Moreover, parasitic agents causing disease or symptoms that can be treated or detected by a polynucleotide or polypeptide and/or agonist or antagonist of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide and/or agonist or antagonist of the present invention can be used to treat or detect any of these symptoms or diseases.

Preferably, treatment using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide and/or agonist or antagonist of the present invention.

Chemotaxis

A polynucleotide or polypeptide and/or agonist or antagonist of the present invention may have chemotaxis activity.

A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide and/or agonist or antagonist of the present invention may inhibit chemotactic activity. These molecules could also be used to treat disorders. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-lradiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense And Ribozyme (Antagonists)

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense riucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:3942 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3'Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3'Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5'Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ D NO:Y beginning with the residue at the position of the First Amino Acid of the Secreted Portion of SEQ D NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library Plasmid | Corresponding Deposited |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128, 256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, N.Y.) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 3040 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 μg of the above cDNA template. A convenient reaction mixture is 1.5–5 mM MgCl$_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with p32 using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5'end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHi and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp'), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacd repressor, clearing the P/O leading to increased gene expression.

Cells are grown for an extra 3 to 4 hours. Cells are then harvested by centrifugation (20 mins at 6000Xg). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6 x His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000 xg for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 24 hours. After 7000 xg centrifugation for 15 min., the pellet is discarded and the polypeptide containing supernatant is incubated at 4° C. overnight to allow further GuHCl extraction.

Following high speed centrifugation (30,000 xg) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A2. monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 μg/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the Autographa californica nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. $E.$ $coli$ HB 101 or other suitable $E.$ $coli$ hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five $\mu$g of a plasmid containing the polynucleotide is co-transfected with 1.0 $\mu$g of a commercially available linearized baculovirus DNA ("BaculoGold™ baculovirus DNA", Pharmingen, San Diego, Calif.), using the lipofection method described by Feigner et al., Proc. Natl. Acad. Sci. USA 84:7413–7417 (1987). One $\mu$g of BaculoGold™ virus DNA and 5 $\mu$g of the plasmid are mixed in a sterile well of a microtiter plate containing 50 gl of serum-free Grace's medium (Life Technologies Inc., Gaithersburg, Md.). Afterwards, 10 $\mu$l Lipofectin plus 90 $\mu$l Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 $\mu$l of Grace's medium and the suspension containing the recombinant baculovirus is used to infect Sf9 cells seeded in 35 mm dishes. Four days later the supernatants of these culture dishes are harvested and then they are stored at 40° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 $\mu$Ci of $^{35}$S-methionine and 5 $\mu$Ci $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QCI–3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991) .) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB 101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 a pC4 is cotransfected with 0.5 μg of the plasmid pSVneo using lipofectin (Feigner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 μg/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with Bam HI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:
GGGATCCGGAGCCCAAATCTTCTGA-
CAAAACTCACACATGCCCACCGTGC CCAG-
CACCTGAATTCGAGGGTGCACCGT-
CAGTCTrCCTCTTCCCCCCAAAA
CCCAAGGACACCCrCATGATCTCCCG-
GACTCCTGAGGTCACATGCGTGGT GGTG-
GACGTAAGCCACGAAGACCCTGAGGT-
CAAGTTCAACTGGTACGTGG
ACGGCGTGGAGGTGCATAATGCCAAGA-
CAAAGCCGCGGGAGGAGCAGTA CAACAG-
CACGTACCGTGTGGTCAGCGTCCTCAC-
CGTCCTGCACCAGGACT
GGCTGAATGGCAAGGAGTACAAGTG-
CAAGGTCTCCAACAAAGCCCTCCCA
ACCCCCATCGAGAAAACCATCTC-
CAAAGCCAAAGGGCAGCCCCGAGAAC
CACAGGTGTACACCCTGCCCCCATC-
CCGGGATGAGCTGACCAAGAACCAG GTCAGC-
CTGACCTGCCTGGTCAAAGGCTTCTATC-
CAAGCGACATCGCCGT
GGAGTGGGAGAGCAATGGGCAGCCG-
GAGAACAACTACAAGACCACGCCT CCCGT-
GCTGGACTCCGACGGCTCCTTCTTCCTC-
TACAGCAAGCTCACCGTG
GACAAGAGCAGGTGGCAGCAGGG-
GAACGTCTTCTCATGCTCCGTGATGCA TGAG-
GCTCTGCACAACCACTACACGCAGAA-
GAGCCTCTCCCTGTCTCCGG
GTAAATGAGTGCGACGGCCGCGACTCTA-
GAGGAT (SEQ ID NO:1)

Example 10

Production of an Antibody from a Polypeptide

The antibodies of the present invention can be prepared by a variety of methods. (See, Current Protocols, Chapter 2.) As one example of such methods, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production Of Secreted Protein For High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 μg/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 GAL glucose. and L-glutamine (12–604F Biowhittaker))/10% heat inactivated FBS(14–503F Biowhittaker)/1x Penstrep(17–602E Biowhittaker). Let the cells grow overnight.

The next day, mix together in a sterile solution basin: 300 ul Lipofectamine (18324-012 Gibco/BRL) and 5 ml Optimem 1 (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/ Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/ Optimem I complex to the odd wells first, then to the even wells, to each row on the 24-well plates. Incubate at 37 degrees C for 6 hours.

While cells are incubating, prepare appropriate media, either 1%BSA in DMEM with 1x penstrep, or CHO-5 media (116.6 mg/L of $CaCl2$ (anhyd); 0.00130 mg/L $CuSO_4$-$5H_2O$; 0.050 mg/L of $Fe(NO_3)_3$–$9H_2O$; 0.417 mg/L of $FeSO_4$–$7H_2O$ 311.80 mg/L of Kcl; 28.64 mg/L of $MgCl_2$; 48.84 mg/L of $MgSO_4$; 6995.50 mg/L of NaCl; 2400.0 mg/L of NaHCO$_3$; 62.50 mg/L of NaH$_2$PO$_4$-H$_2$O; 71.02 mg/L of Na$_2$HPO4; 0.4320 mg/L of ZnSO$_4$-7H$_2$O; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-H$_2$O; 6.65 mg/ml of L-Aspartic Acid; 29.56 mg/ml of L-Cystine-2HCL-H$_2$O; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-H$_2$O; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H$_2$O; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin B$_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 2 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1x penstrep. (BSA (81-068-3 Bayer). 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degrees C for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs tyk2 | Jak1 | Jak2 | Jak3 | STATS | GAS (elements) or ISRE |
|---|---|---|---|---|---|---|
| IFN family | | | | | | |
| IFN-a/B | + | + | − | − | 1,2,3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotrophic) | + | + | + | ? | 1,3 | GAS (IRF1 > Lys6 > IFP) |
| Il-11(Pleiotrophic) | ? | + | ? | ? | 1,3 | |
| OnM(Pleiotrophic) | ? | + | + | ? | 1,3 | |
| LIF(Pleiotrophic) | ? | + | + | ? | 1,3 | |
| CNTF(Pleiotrophic) | −/+ | + | + | ? | 1,3 | |
| G-CSF(Pleiotrophic) | ? | + | ? | ? | 1,3 | |
| IL-12(Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5'primer is:

5':GCGCCTCGAGATTMCCCCGAAATCTA-GATTTCCCCGAAATGATMTCCCC GAAATGAM-CCCCGAAATATCTGCCATCTCAATTAG:3' (SEQ ID NO:3)

The downstream primer is complementary to the SV40 promoter and is flanked with a Hind Im site:
5':GCGGCAAGCTITITGCAAAGCCTAGGC:3'(SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

5':CTCGAGATTTCCCCGAAATCTAGATITC-CCCGAAATGATTTCCCCGAAA TGATTTC-CCCGAAATATCTGCCATCTCAATTAGT-CAGCAACCATAGTCCCG CCCCTAACTCCGCCCATCCCGC-CCCTAACTCCGCCCAGTTCCGCCCATTCT CCGCCCCATGGCTGACTAATTTTTT-TATTTRATGCAGAGGCCGAGGCCGCC TCGGC-CTCTGAGCTATTCCAGAAGTAGTGAG-GAGGCTTTTGGAGGCCT AGGCTTTTGCAAAAGCTT:3' (SEQ ID NO:5)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-I (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GASINF-KB/EGR, GAS/NF-KB, I1-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, determining whether supernate containing a polypeptide of the invention proliferates and/or differentiates T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt4 cells (ATCC Accession No. CRL-1582) cells can also be used.

Jurkat T-cells are lymphoblastic CD4+Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells (107 per transfection), and resuspend in OPTI-MEM to a final concentration of 107 cells/ml. Then add 1 ml of 1×$10^7$ cells in OPTI-MEM to T25 flask and incubate at 37 degrees C for 6 hrs. After the incubation, add 10 ml of RPMI +15% serum.

The Jurkat:GAS-SEAP stable reporter lines are maintained in RPMI+10% serum, 1 mg/ml Genticin, and 1% Pen-Strep. These cells are treated with supernatants containing polypeptides of the invention and/or induced polypeptides of the invention as produced by the protocol described in Example 11.

On the day of treatment with the supernatant, the cells should be washed and resuspended in fresh RPMI +10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degrees C until SEAP assays are performed according to Example 17. The plates containing the remaining treated cells are placed at 4 degrees C and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by determining whether polypeptides of the invention proliferates and/or differentiates myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest 2×$10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degrees C for 45 min.

Wash the cells with RPMI 1640 medium containing 10% FBS and then resuspend in 10 ml complete medium and incubate at 37 degrees C for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting 1×10$^8$ cells (this is enough for ten 96-well plates assay) and wash with PBS. Suspend the cells in 200 ml above described growth medium, with a final density of 5×10$^5$ cells/ml. Plate 200 ul cells per well in the 96-well plate (or 1×15$^5$ cells/well).

Add 50 ul of the supernatant prepared by the protocol described in Example 11. Incubate at 37 degrees C for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity.

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

5'
GCGCTCGAGGGATGACAGCGATAGAACCCCGG-3' (SEQ ID NO:6)

5' GCGAAGCTTCGCGACTCCCCGGATCCGCCTC-3' (SEQ ID NO:7)

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC 12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as 5×10$^5$ cells/ml.

Add 200 ul of the cell suspension to each well of 96-well plate (equivalent to 1×10$^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from stress responses.

In non-stimulated conditions, NF-κB is retained in the cytoplasm with I-κB (Inhibitor κB). However, upon stimulation, I-κB is phosphorylated and degraded, causing NF-κB to by NF-KB include IL-2, IL-6, GM-CSF, ICAM-1 and class 1 MHC. by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-KB would be useful in treating diseases. For example, inhibitors of NF-κB could be used to treat those diseases related to the acute or chronic activation of NF-KB, such as rheumatoid arthritis.

To construct a vector containing the NF-κB promoter element, a PCR based strategy is employed. The upstream primer contains four tandem copies of the NF-κB binding site (GGGGACTTTCCC)(SEQ ID NO:8), 18 bp of sequence complemtentary to the 5' end of the SV40 early promoter sequence, and is flanked with an XhoI site:

5 ':GCGGCCTCGAGGGGACTTTCCCGGG-GACTTTCCGGGGACMTTCCGGGACTTTCC ATCCTGCCATCTCAATTAG:3'(SEQ ID NO:9)

The downstream primer is complementary to the 3' end of the SV40 promoter and is flanked with a Hind III site:

5':GCGGCAAGCTITITGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5 ':CTCGAGGGGACTTTCCCGGGGACTTTC-CGGGGACTTTCCGGGACTTTCC ATCTGC-CAT CT C A AT TAG T C AG C A AC C AT AG TC-

CCGCCCCTAACTCCGCCC
ATCCCGCCCCTAACTCCGCCCAGTTC-
CGCCCATTCTCCGCCCCATGGCTGA
CTAATTTTTTTATTTATGCAGAGGC-
CGAGGCCGCCTCGGCCTCTGAGCTA TTCCA-
GAAGTAGTGAGGAGGCTTTTTGGAGGC-
CTAGGCTGCAAAAA GCTT:3' (SEQ ID NO: 10)

Next, replace the SV40 minimal promoter element present in the pSEAP2-promoter plasmid (Clontech) with this NF-κB/SV40 fragment using XhoI and HindIII. However, this mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP with SalI and NotI.

Once NF-κB/SV40/SEAP/Neo vector is created, stable Jurkat T-cells are created and assaying supernatants with these stable Jurkat T-cells is also described in Example 13. As a positive control, exogenous TNF alpha (0.1,1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5x Dilution Buffer and dispense 15 μl of 2.5x dilution buffer into Optiplates containing 35 μl of a supernatant. Seal the plates with a plastic sealer and incubate at 65 degrees C for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.
Reaction Buffer Formulation:

| # of plates | Rxn buffer diluent (ml) | CSPD (ml) |
| --- | --- | --- |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |

-continued

| # of plates | Rxn buffer diluent (ml) | CSPD (ml) |
| --- | --- | --- |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo4 is made in 10% pluronic acid DMSO. To load the cells with fluo4 , 50 ul of 12 ug/ml fluo-4 is added to each well. The plate is incubated at 37 degrees C in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo4 solution in 10% pluronic acid DMSO is added to each ml of cell suspension. The tube is then placed in a 37 degrees C water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular Ca++ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200ml/well) and cultured overnight in complete medium. Cells are quiesced by incubation in serum-free basal medium for 24 hr. After 5–20 minutes treatment with EGF (60ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P207 and a cocktail of protease inhibitors (#1836170) obtained from Boeheringer Mannheim (Indianapolis, Ind.) is added to each well and the plate is shaken on a rotating shaker for 5 minutes at 4 degrees C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degrees C at 16,000 x g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSKI (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$(5 mM ATP/50 mM MgCl$_2$), then 10 ul of 5x Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30 degrees C for 2 min. Initial the reaction by adding 10ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degrees C for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37 degrees C for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation-of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (10 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degrees C until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95 degrees C for 30 seconds; 60–120 seconds at 52–58 degrees C; and 60–120 seconds at 70 degrees C, using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diarnino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Compositions of the invention are also suitably administered by sustained-release systems. Suitable examples of sustained-release compositions include suitable polymeric materials (such as, for example, semi-permeable polymer matrices in the form of shaped articles, e.g., films, or m hydrophobic materials (for example as an emulsion in an acceptable oil) of ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277) (1981), and Langer, Chem. Tech. 12:98–105 (1982)), ethylene vinyl acetate (Langer et al., Id.) or poly-D-(-)-3-hydroxybutyric acid (EP 133,988).

Sustained-release compositions also include liposomally entrapped compositions of the invention (see generally, Langer, Science 249:1527–1533 (1999); Treat et al., in Liposomes in the Therapy of Infectious Disease and Cancer, Lopez-Berstein and Fidler (eds.), Liss, N.Y., pp. 317–327 and 353–365 (1989)). Liposomes containing XXX polypeptide my be prepared by methods known per se: DE 3,218, 121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal XXX polypeptide therapy.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or fined divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts;antioxidants such as ascorbic acid; low molecular weight (less than about tenresidues) polypeptides, e.g., polyarginine or tripeptides; proteins, such as serumalbumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including celluloseor its derivatives, glucose, manose, or dextrins; chelating agents such as EDTA; sugaralcohols such as mannitol or sorbitol; counterions such as sodium; and/or nonionicsurfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes(e.g., 0.2 micron membranes). Therapeutic polypeptide compositions generally are placed into a container having a sterile access port, for example, an intravenoussolution bag or vial having a stopper pierceable by a hypodermic injection needle.

Polypeptides ordinarily will be stored in unit or multi-dose containers, for example, sealed ampoules or vials, as an aqueous solution or as a lyophilizedformulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared byreconstituting the lyophilized polypeptide using bacteriostatic Water-for-Injection.

The invention also provides a pharmaceutical pack or kit comprising one or more containers filled with one or more of the ingredients of the pharmaceuticalcompositions of the invention. Associated with such container(s) can be a notice in the form prescribed by a governmental agency regulating the manufacture, use or saleof pharmaceuticals or biological products, which notice reflects approval by theagency of manufacture, use or sale for human administration. In addition, thepolypeptides of the present invention may be employed in conjunction with othertherapeutic compounds.

The compositions of the invention may be administered alone or in combination with other therapeutic agents. Therapeutic agents that may beadministered in combination with the compositions of the invention, include but notlimited to, other members of the TNF family, chemotherapeutic agents, antibiotics,steroidal and non-steroidal anti-inflammatories, conventional immunotherapeuticagents, cytokines and/or growth factors. Combinations may be administered eitherconcomitantly, e.g., as an admixture, separately but simultaneously or concurrently;or sequentially. This includes presentations in which the combined agents areadministered together as a therapeutic mixture, and also procedures in which thecombined agents are administered separately but simultaneously, e.g., as through-separate intravenous lines into the same individual. Administration "in combination" further includes the separate administration of one of the compounds or agents givenfirst, followed by the second.

In one embodiment, the compositions of the invention are administered in combination with members of the TNF family. TNF, TNF-related or TNF-likemolecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD 154, CD70, and CD153.

Conventional nonspecific immunosuppressive agents, that may be administered in combination with the compositions of the invention include, but arenot limited to, steroids, cyclosporine, cyclosporine analogs, cyclophosphamidemethylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administeredwith the compositions of the invention include, but are not limited to, tetracycline,metronidazole, amoxicillin, beta-lactamases, aminoglycosides, macrolides,quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone,guaiazulene, nabumetone, nimesulide, orgotein, oxaceprol, paranyline, perisoxal,pifoxime, proquazone, proxazole, and tenidap.

In another embodiment, compostions of the invention are administered in combination with a chemotherapeutic agent. Chemotherapeutic agents that may beadministered with the compositions of the invention include, but are not limited to,antibiotic derivatives (e.g., doxorubicin, bleomycin, daunorubicin, anddactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate);hormones (e.g., medroxyprogesterone, estramustine phosphate sodium, ethinylestradiol, estradiol, megestrol acetate, methyltestosterone, diethylstilbestroldiphosphate, chlorotrianisene, and testolactone); nitrogen mustard derivatives (e.g.,mephalen, chorambucil, mechlorethamine (nitrogen mustard) and thiotepa); steroidsand combinations (e.g., bethamethasone sodium phosphate); and others (e.g., dicarbazine, asparaginase, mitotane, vincristine sulfate, vinblastine sulfate, andetoposide).

In an additional embodiment, the compositions of the invention are administered in combination with cytokines. Cytokines that may be administeredwith the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that maybe administered with the compositions of the invention include, but are not limited to,Glioma Derived Growth Factor (GDGF), as disclosed in European Patent NumberEP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International PublicationNumber WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in InternationalPublication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast GrowthFactors that may be administered with the compositions of the invention include, butare not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15. In additional embodiments, the compositions of the invention are administered incombination with other therapeutic or prophylactic regimens, such as, for example,radiation therapy.

Example 24

Method of Treating Decreased Levels of the Polypeptide

The present invention relates to a method for treating an individual in need of an increased level of a polypeptide of the invention in the body comprisingadministering to such an individual a composition comprising a therapeutically-effective amount of an agonist of the invention (including polypeptides of theinvention). Moreover, it will be appreciated that conditions caused by a decrease inthe standard or normal expression level of a secreted protein in an individual can be treated by administering the polypeptide of the present invention, preferably in thesecreted form. Thus, the invention also provides a method of treatment of anindividual in need of an increased level of the polypeptide comprising administeringto such an individual a pharmaceutical composition comprising an amount of thepolypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based onadministration and formulation, are provided in Example 23.

Example 25

Method of Treating Increased Levels of the Polypeptide

The present invention also relates to a method of treating an individual in need of a decreased level of a polypeptide of the invention in the body comprisingadministering to such an individual a composition comprising a therapeutically effective amount of an antagonist of the invention (including polypeptides andantibodies of the invention).

In one example, antisense technology is used to inhibit production of a polypeptide of the present invention. This technology is one example of a method ofdecreasing levels of a polypeptide, preferably a secreted form, due to a variety ofetiologies, such as cancer. For example, a patient diagnosed with abnormallyincreased levels of a polypeptide is administered intravenously antisensepolynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy-Ex Vivo

One method of gene therapy transplants fibroblasts, which are capable of expressing a polypeptide, onto a patient. Generally, fibroblasts are obtained from asubject by skin biopsy. The resulting tissue is placed in tissue-culture medium andseparated into small pieces. Small chunks of the tissue are placed on a wet surface ofa tissue culture flask, approximately ten pieces are placed in each flask. The flask is turned upside down, closed tight and left at room temperature over night. After 24 hours at room temperature, the flask is inverted and the chunks of tissue remain fixedto the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge.The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI andHindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. Theligation mixture is then used to transform bacteria HB101, which are then plated onto agar containing kanamycin for the purpose of confirming that the vector has the geneof interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector.The packaging cells now produce infectious viral particles containing the gene (thepackaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to removedetached producer cells and this media is then used to infect fibroblast cells. Media isremoved from a sub-confluent plate of fibroblasts and quickly replaced with themedia from the producer cells. This media is removed and replaced with fresh media.If the titer of virus is high, then virtually all fibroblasts will be infected and noselection is required. If the titer is very low, then it is necessary to use a retroviralvector that has a selectable marker, such as neo or his. Once the fibroblasts have beenefficiently infected, the fibroblasts are analyzed to determine whether protein isproduced.

The engineered fibroblasts are then transplanted onto the host, either alone or after having been grown to confluence on cytodex 3 microcarrier beads.

Example 27

Gene Therapy Using Endogenous Genes Corresponding To Polynucleotides of the Invention Another method of gene therapy according to the present invention involves operably associating the endogenous polynucleotide sequence of the invention with apromoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435438 (1989). This method involves the activation of a gene which is present in the target cells, but which is not expressed inthe cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will besufficiently near the 5' end of the polynucleotide sequence so the promoter will be operably linked to the endogenous sequence upon homologous recombination. Thepromoter and the targeting sequences can be amplified using PCR. Preferably, theamplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinalphosphatase. The digested promoter and digested targeting sequences are addedtogether in the presence of T4 DNA ligase. The resulting mixture is maintained under conditions appropriate for ligation of the two fragments. The construct is sizefractionated on an agarose gel then purified by phenol extraction and ethanolprecipitation.

In this Example, the polynucleotide constructs are administered as naked polynucleotides via electroporation. However, the polynucleotide constructs may alsobe administered with transfection-facilitating agents, such as liposomes, viralsequences, viral particles, precipitating agents, etc. Such methods of delivery areknown in the art.

Once the cells are transfected, homologous recombination will take place which results in the promoter being operably linked to the endogenous polynucleotidesequence. This results in the expression of polynucleotide corresponding to thepolynucleotide in the cell. Expression may be detected by immunological staining, orany other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrientmedium. An aliquot of the cell suspension is removed for counting, and the remainingcells are subjected to centrifugation. The supernatant is aspirated and the pellet isresuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension containsapproximately $3 \times 10^6$ cells/ml. Electroporation should be performed immediately following resuspension.

Plasmid DNA is prepared according to standard techniques. For example, to construct a plasmid for targeting to the locus corresponding to the polynucleotide ofthe invention, plasmid pUC 18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter-XbaI and BamHI; fragment 1-XbaI; fragment 2-BamHI) and ligated together. The resulting ligation product is digested with HindIII, and ligated with the HindIII digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation isperformed with a Gene-Pulser apparatus (Bio-Rad). Capacitance and voltage are set at960 μF and 250–300 V, respectively. As voltage increases, cell survival decreases, but the percentage of surviving cells that stably incorporate the introduced DNAinto theirgenome increases dramatically. Given these parameters, a pulse time ofapproximately 14–20 mSec should be observed.

Electroporated cells are maintained at room temperature for approximately 5 min, and the contents of the cuvette are then gently removed with a sterile transferpipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into apatient as described above.

Example 28

Method of Treatment Using Gene Therapy—In Vivo

Another aspect of the present invention is using in vivo gene therapy methods to treat disorders, diseases and conditions. The gene therapy method relates to theintroduction of naked nucleic acid (DNA, RNA, and antisense DNA or RNA)sequences into an animal to increase or decrease the expression of the polypeptide.The polynucleotide of the present invention may be operatively linked to a promoteror any other genetic elements necessary for the expression of the polypeptide by thetarget tissue. Such gene therapy and delivery techniques and methods are known inthe art, see, for example, WO90/11092, WO98/11779; U.S. Pat. Nos. 5,693,622, 5,705,151, 5,580,859; Tabata et al., Cardiovasc. Res. 35(3):470479 (1997); Chao et al., Pharmacol. Res. 35(6):517–522 (1997); Wolff, Neuromuscul. Disord. 7(5):314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitialspace of tissues (heart, muscle, skin, lung, liver, intestine and the like). Thepolynucleotide constructs can be delivered in a pharmaceutically acceptable liquid oraqueous carrier.

The term "naked" polynucleotide, DNA or RNA, refers to sequences that are free from any delivery vehicle that acts to assist, promote, or facilitate entry into thecell, including viral sequences, viral particles, liposome formulations, lipofectin orprecipitating agents and the like. However, the polynucleotides of the presentinvention may also be delivered in liposome formulations (such as those taught inFelgner P. L. et al. (1995) Ann. N.Y. Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they containsequences that allow for replication. Any strong promoter known to those skilled inthe art can be used for driving the expression of DNA. Unlike other gene therapies techniques, one major advantage of introducing naked nucleic acid sequences intotarget cells is the transitory nature of the polynucleotide synthesis in the cells. Studieshave shown that non-replicating DNA sequences can be introduced into cells toprovide production of the desired polypeptide for periods of up to six months.

The polynucleotide construct can be delivered to the interstitial space of tissues within the an animal, including of muscle, skin, brain, lung, liver, spleen, bonemarrow, thymus, heart, lymph, blood, bone, cartilage, pancreas, kidney, gall bladder,stomach, intestine, testis, ovary, uterus, rectum, nervous system, eye, gland, andconnective tissue. Interstitial space of the tissues comprises the intercellular fluid,mucopolysaccharide matrix among the reticular fibers of organ tissues, elastic fibersin the walls of vessels or chambers, collagen fibers of fibrous tissues, or that samematrix within connective tissue ensheathing muscle cells or in the lacunae of bone. Itis similarly the space occupied by the plasma of the circulation and the lymph fluid ofthe lymphatic channels. Delivery to the interstitial space of muscle tissue is preferred for the reasons discussed below. They may be conveniently delivered by injectioninto the tissues comprising these cells. They are preferably delivered to andexpressed in persistent, non-dividing cells which are differentiated, although deliveryand expression may be achieved in non-differentiated or less completelydifferentiated cells, such as, for example, stem cells of blood or skin fibroblasts. Invivo muscle cells are particularly competent in their ability to take up and expresspolynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to thetissue site of injection. The appropriate and effective dosage of nucleic acid sequencecan readily be determined by those of ordinary skill in the art and may depend on thecondition being treated and the route of administration. The preferred route ofadministration is by the parenteral route of injection into the interstitial space oftissues. However, other parenteral routes may also be used, such as, inhalation of an aerosol formulation particularly for delivery to lungs or bronchial tissues, throat ormucous membranes of the nose. In addition, naked polynucleotide constructs can bedelivered to arteries during angioplasty by the catheter used in the procedure.

The dose response effects of injected polynucleotide in muscle in vivo is determined as follows. Suitable template DNA for production of mRNA coding forpolypeptide of the present invention is prepared in accordance with a standardrecombinant DNA methodology. The template DNA, which may be either circular orlinear, is either used as naked DNA or complexed with liposomes. The quadricepsmuscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The templateDNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. Atime course for protein expression may be done in a similar fashion except thatquadriceps from different mice are harvested at different times. Persistence of DNAin muscle following injection may be determined by Southern blot analysis afterpreparing total cellular DNA and HIRT supernatants from injected and control mice. The results of the above experimentation in mice can be use to extrapolate properdosages and other treatment parameters in humans and other animals using naked DNA.

Example 29

Transgenic Animals

The polypeptides of the invention can also be expressed in transgenic animals. Animals of any species, including, but not limited to, mice, rats, rabbits, hamsters,guinea pigs, pigs, micro-pigs, goats, sheep, cows and non-human primates, e.g., baboons, monkeys, and chimpanzees may be used to-generate transgenic animals. In a specific embodiment, techniques described herein or otherwise known in the art, areused to express polypeptides of the invention in humans, as part of a gene therapyprotocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11: 1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 30

Knock-Out Animals

Endogenous gene expression can also be reduced by inactivating or "knocking out" the gene and/or its promoter using targeted homologous recombination. (e.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro usingrecombinant DNA techniques to introduce the coding sequence of polypeptides of theinvention into the cells, or alternatively, to disrupt the coding sequence and/or endogenous regulatory sequence associated with the polypeptides of the invention,e.g., by transduction (using viral vectors, and preferably vectors that integrate the transgene into the cell genome) or transfection procedures, including, but not limitedto, the use of plasmids, cosmids, YACs, naked DNA, electroporation, liposomes, etc.The coding sequence of the polypeptides of the invention can be placed under thecontrol of a strong constitutive or inducible promoter or promoter/enhancer to achieveexpression, and preferably secretion, of the polypeptides of the invention. The engineered cells which express and preferably secrete the polypeptides of the invention can be introduced into the patient systemically, e.g., in the circulation, orintraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic orvascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques whichprevent the development of a host immune response against the introduced cells. Forexample, the cells may be introduced in an encapsulated form which, while allowingfor an exchange of components with the immediate extracellular environment, doesnot allow the introduced cells to be recognized by the host immune system.

Transgenic and "knock-out" animals of the invention have uses which include, but are not limited to, animal model systems useful in elaborating the biological function of polypeptides of the present invention, studying conditions and/or disordersassociated with aberrant expression, and in screening for compounds effective inameliorating such conditions and/or disorders.

Example 31

Isolation of Antibody Fragments Directed Against Polypeptides of the Invention From a Library of scFvs.

Naturally occurring V-genes isolated from human PBLs are constructed into a large library of antibody fragments which contain reactivities against apolypeptide having the amino acid sequence of SEQ ID NO:Y to which the donormay or may not have been exposed (see e.g., U.S. Pat. 5,885,793 incorporated herein in its entirety by reference).

Rescue of the library.

A library of scFvs is constructed from the RNA of human PBLs as described in WO92/01047. To rescue phage displaying antibody fragments, approximately $10^9$ E. coli harboring the phagemid are used to inoculate 50 ml of 2×TY containing 1% glucose and 100 micrograms/ml of ampicillin (2×TY-AMP-GLU) and grown to an O.D. of 0.8 with shaking. Five ml of this culture is used to inoculate 50 ml of 2×TY-AMP-GLU, $2×10^8$ TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of of 2×TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibodyfragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2×TY broth containing 100 micrograms ampicillin/ml and 25 micrograms kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in PBS with 4 ml of either 100 micrograms/ml or 10 micrograms/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 micrograms/ml ampicillin. The resulting bacterial library is then rescued with delta gene 3 helper phage as described above to prepare phage for a subsequent round of selection. This processis then repeated for a total of 4 rounds of affinity purification with tube-washing increased to 20 times with PBS, 0.1% Tween-20 and 20 times with PBS for rounds 3 and4.

Characterization of Binders.

Eluted phage from the third and fourth rounds of selection are used to infect E. coli HB2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

It will be clear that the invention may be practiced otherwise than as particularly described in the foregoing description and examples. Numerous modifications and variations of the present invention are possible in light of the aboveteachings and, therefore, are within the scope of the appended claims.

The entire disclosure of each document cited (including patents, patent applications, journal articles, abstracts, laboratory manuals, books, or otherdisclosures) in the Background of the Invention, Detailed Description, and Examplesis hereby incorporated herein by reference. Further, the hard copy of the sequencelisting submitted herewith and the corresponding computer readable form are bothincorporated herein by reference in their entireties.

What is claimed is:

1. An isolated protein comprising amino acid residues 23 to 74 of SEQ ID NO:73.

2. The isolated protein of claim 1 which comprises amino acid residues 2 to 74 of SEQ ID NO:73.

3. The isolated protein of claim 1 which comprises amino acid residues 1 to 74 of SEQ ID NO:73.

4. The protein of claim 1 which further comprises a polypeptide sequence heterologous to SEQ ID NO:73.

5. A composition comprising the protein of claim 1 and a carrier.

6. An isolated protein produced by the method comprising:
  (a) expressing the protein of claim 1 by a cell; and
  (b) recovering said protein.

7. An isolated protein comprising the amino acid sequence of the secreted portion of the polypeptide encoded by the HAMGO32 cDNA contained in ATCC Deposit No. 209626.

8. The isolated protein of claim 7 which comprises the amino acid sequence of the complete polypeptide encoded by the HAMGO32 cDNA contained in ATCC Deposit No. 209626, excepting the N-terminal methionine.

9. The isolated protein of claim 7 which comprises the amino acid sequence of the complete polypeptide encoded by the HAMGO32 cDNA contained in ATCC Deposit No. 209626.

10. The protein of claim 7 which further comprises a polypeptide sequence heterologous to the complete polypeptide encoded by the HAMGO32 cDNA contained in ATCC Deposit No. 209626.

11. A composition comprising the protein of claim 7 and a carrier.

12. An isolated protein produced by the method comprising:
  (a) expressing the protein of claim 7 by a cell; and
  (b) recovering said protein.

13. An isolated first polypeptide at least 90% identical to a second polypeptide consisting of amino acid residues 23 to 74 of SEQ ID NO:73.

14. The isolated polypeptide of claim 13, wherein said first polypeptide is at least 95% identical to said second polypeptide.

15. The protein of claim 13 which further comprises a polypeptide sequence heterologous to SEQ ID NO:73.

16. A composition comprising the protein of claim 13 and a carrier.

17. An isolated protein produced by the method comprising:
  (a) expressing the protein of claim 13 by a cell; and
  (b) recovering said protein.

18. An isolated first polypeptide at least 90% identical to a second polypeptide consisting of the secreted portion of the polypeptide encoded by the HAMGO32 cDNA contained in ATCC Deposit No. 209626.

19. The isolated polypeptide of claim 18, wherein said first polypeptide is at least 95% identical to said second polypeptide.

20. The protein of claim 18 which further comprises a polypeptide sequence heterologous to the secreted portion of the polypeptide encoded by the HAMGO32 cDNA contained in ATCC Deposit No. 209626.

21. A composition comprising the protein of claim 18 and a carrier.

22. An isolated protein produced by the method comprising:
(a) expressing the protein of claim 18 by a cell; and
(b) recovering said protein.

23. An isolated first polypeptide at least 90% identical to a second polypeptide consisting of amino acid residues 1 to 74 of SEQ ID NO:73.

24. The isolated polypeptide of claim 23, wherein said first polypeptide is at least 95% identical to said second polypeptide.

25. The protein of claim 23 which further comprises a polypeptide sequence heterologous to SEQ ID NO:73.

26. A composition comprising the protein of claim 23 and a carrier.

27. An isolated protein produced by the method comprising:
(a) expressing the protein of claim 23 by a cell; and
(b) recovering said protein.

28. An isolated first polypeptide at least 90% identical to a second polypeptide consisting of the complete polypeptide encoded by the HAMGO32 cDNA contained in ATCC Deposit No. 209626.

29. The isolated polypeptide of claim 28, wherein said first polypeptide is at least 95% identical to said second polypeptide.

30. The protein of claim 28 which further comprises a polypeptide sequence heterologous the complete polypeptide encoded by the HAMGO32 cDNA contained in ATCC Deposit No. 209626.

31. A composition comprising the protein of claim 28 and a carrier.

32. An isolated protein produced by the method comprising:
(a) expressing the protein of claim 28 by a cell; and
(b) recovering said protein.

33. An isolated protein consisting of at least 30 contiguous amino acid residues of amino acid residues 1 to 74 of SEQ ID NO:73.

34. The isolated protein of claim 33 which consists of at least 50 contiguous amino acid residues of amino acid residues 1 to 74 of SEQ ID NO:73.

35. The protein of claim 33 which further comprises a polypeptide sequence heterologous to SEQ ID NO:73.

36. A composition comprising the protein of claim 33 and a carrier.

37. An isolated protein produced by the method comprising:
(a) expressing the protein of claim 33 by a cell; and
(b) recovering said protein.

38. An isolated protein consisting of at least 30 contiguous amino acid residues of the complete polypeptide encoded by the HAMGO32 cDNA contained in ATCC Deposit No. 209626.

39. The isolated protein of claim 38 which consists of at least 50 contiguous amino acid residues of the complete polypeptide encoded by the HAMGO32 cDNA contained in ATCC Deposit No. 209626.

40. The protein of claim 38 which further comprises a polypeptide sequence heterologous to the complete polypeptide encoded by the HAMGO32 cDNA contained in ATCC Deposit No. 209626.

41. A composition comprising the protein of claim 38 and a carrier.

42. An isolated protein produced by the method comprising:
(a) expressing the protein of claim 38 by a cell; and
(b) recovering said protein.

* * * * *

UNITED STATES PATENT AND TRADEMARK OFFICE
CERTIFICATE OF CORRECTION

PATENT NO. : 6,632,920 B1
DATED : October 14, 2003
INVENTOR(S) : Olsen et al.

It is certified that error appears in the above-identified patent and that said Letters Patent is hereby corrected as shown below:

<u>Column 140,</u>
Line 24, please insert the following title:
-- Example 16
High-Throughput Screening Assay for T-cell Activity --

Signed and Sealed this

Eleventh Day of May, 2004

JON W. DUDAS
*Acting Director of the United States Patent and Trademark Office*